US007449551B2

(12) United States Patent
Goddard et al.

(10) Patent No.: US 7,449,551 B2
(45) Date of Patent: *Nov. 11, 2008

(54) PRO211 POLYPEPTIDES

(75) Inventors: Audrey Goddard, San Francisco, CA (US); Austin L. Gurney, Belmont, CA (US); Paul J. Godowski, Burlingame, CA (US); William I. Wood, Hillsborough, CA (US); Napoleone Ferrara, San Francisco, CA (US)

(73) Assignee: Genentech, Inc., California, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/355,441

(22) Filed: Feb. 15, 2006

(65) Prior Publication Data

US 2006/0149038 A1    Jul. 6, 2006

Related U.S. Application Data

(63) Continuation of application No. 09/905,075, filed on Jul. 13, 2001, now Pat. No. 7,169,906, which is a continuation of application No. 09/665,350, filed on Sep. 18, 2000, now abandoned, which is a continuation of application No. PCT/US00/04414, filed on Feb. 22, 2000, which is a continuation-in-part of application No. PCT/US99/23089, filed on Oct. 5, 1999, and a continuation-in-part of application No. PCT/US98/19330, filed on Sep. 16, 1998, which is a continuation-in-part of application No. PCT/US98/18824, filed on Sep. 10, 1998.

(60) Provisional application No. 60/104,080, filed on Oct. 13, 1998, provisional application No. 60/059,263, filed on Sep. 18, 1997.

(51) Int. Cl.
*C07K 14/00* (2006.01)
*C07K 7/00* (2006.01)
*A61K 39/00* (2006.01)

(52) U.S. Cl. .................. 530/350; 530/300; 530/387.3; 424/185.1; 424/192.1

(58) Field of Classification Search ........................ None
See application file for complete search history.

(56) References Cited

U.S. PATENT DOCUMENTS

| 5,561,053 | A |  | 10/1996 | Crowley |  |
|---|---|---|---|---|---|
| 5,635,177 | A |  | 6/1997 | Bennett et al. |  |
| 5,891,637 | A |  | 4/1999 | Ruppert |  |
| 6,030,831 | A |  | 2/2000 | Godowski et al. |  |
| 7,169,906 | B2 | * | 1/2007 | Ferrara et al. | ............... 530/399 |

FOREIGN PATENT DOCUMENTS

| EP | 0834563 | 4/1998 |
|---|---|---|
| WO | 94/01548 | 1/1994 |
| WO | 9707198 | 2/1997 |
| WO | 99/14241 | 3/1999 |
| WO | 99/14327 | 3/1999 |
| WO | 9914328 | 3/1999 |
| WO | WO 99/14327 | 3/1999 |
| WO | 99/58660 | 11/1999 |
| WO | WO 0104311 | 1/2000 |
| WO | 00/15666 | 3/2000 |
| WO | WO 00/15796 | 3/2000 |
| WO | WO 00/21996 | 4/2000 |
| WO | WO 00/53753 | 9/2000 |
| WO | WO 00/55319 | 9/2000 |
| WO | WO 01/05836 | 1/2001 |

OTHER PUBLICATIONS

Xian et al., 2004, Frontiers in Bioscience, 9. pp. 85-92.*
Chen, H. et al., "*Cricetulus griseus* HT protein mRNA, complete cds", Database EMBL-EMROD Online!, Entry CG48852, Acc. No. U48852, 1-2 (1996).
Hillier, L., et al., "zr65g02.sl Soares NhHMPu_S1 *Homo sapiens* cDNA clone 668306 3' similar to TR:G1216486 G1216486 HT Protein", Database EMBL-EMEST15 [Online], Entry Hsaa42749, Acc. No. AA242749, 1-2 (1997).
Klein, R., et al., "Selection for genes encoding secreted proteins and receptors", Proc. Natl. Acad. Sci. USA, 93: 7108-7113, (1996).
Revelle, B., et al., "Single amino acid residues in the E- and P-selectin Epiderrmal Growth Factor domains can determine carbohydrate binding specificity", The Journal of Biological Chemistry, 271:No. 27, 16160-16170, (1996).
Strausberg, R., "oo14fl2.x1 soars_NSF_F8_9W_OT_PA_P_S1 *Homo sapiens* cDNA clone IMAGE:1566191 3' similar to TR:Q60438 Q60438 HT Protein; mRNA sequence", Database EMBL-EMST6 'Online!, Entry/Acc No. A1066551, 1-2 (1998).
Yokoyama-Kobayashi, M. et al., "A signal detection system using secreted protease activity as an indicator", Gene, 163: 193-196 (1995).
Carpenter et al., Handbook of Experimental Pharmacology; Chapter 4, The Epidermal Growth Factor Family, pp. 69-171, (1990).
Database EMBL-Entry Cg48858, Mar. 18, 1996, Chen et al., *Cricetulus griseus* HT protein nRNA, complete cds.
Database EMBL-Entry Hsaa42749, Mar. 19, 1997, Hillier, L., et al., zr65g02.s1 Soares NhHmPu S1 *Homo sapiens* cDNA clone 668306.3 similar to TR:G1216486 G1216486GT protein.
De Boer, Willem I., "Expression and Functions of EGF, FGF and TGFβ-Growth Factor Family Members and Their Receptors in Invasive Human Transitional-Cell-Carcinoma Cells," *Int. J. Cancer*, 71: 284-291 (1997).

(Continued)

*Primary Examiner*—Olga N Chernyshev
(74) *Attorney, Agent, or Firm*—Elizabeth M. Barnes; Christopher De Vry; Ginger R. Dreger

(57) ABSTRACT

The present invention is directed to novel polypeptides and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

4 Claims, 4 Drawing Sheets

OTHER PUBLICATIONS

Lusson, Vieau D., "cDNA Structure of the Mouse and Rat Subtilisin/Kexin-like PC5: A Candidate Proprotein Convertase Expressed in Endocrine and Nonendocrine Cells," *Proc. Natl. Acad. Sci.*, 90: 6691-6695 (1993).

Roebroek, Anton J.M., "Cloning and Functional Expression of Dfurin2, a Subtilisin-like Proprotein Processing Enzyme of *Drosophila melanogaster* with Multiple Repeats of a Cysteine Motif," *The Journal of Biological Chemistry*, 267:(24) 17208-17215 (1992).

EMBL U48852. Chen, et al., HT protein, cricetulus, Nov. 1, 1996.

Dayhoff, P_AAB53075, WO200053753-A2, (Sep. 14, 2000), Ashkenazi A.J., et al.

Dayhoff, P_AAB61231, WO200100638-A2, (Jan. 4, 2001), Kirst S.J., et al.

Dayhoff, P_AAB80212, WO200104311-A1, (Jan. 18, 200), Ashkenazi A.J., et al.

Dayhoff, P_AAB68596, WO200105836-A1, (Jan. 25, 2001), Botstein D., et al.

Dayhoff, P_AAY83224, WO200021996-A2, (Apr. 20, 2000), Ashkenazi A.J., et al.

Dayhoff, P_AAB00169, WO200055319-A1, (Sep. 21, 2000), Ashkenazi A.J., et al.

Dayhoff, P_AAY05283, WO9914327-A2, (Mar. 25, 1999), Botstein D., et al.

Dayhoff, P_AAY13344, WO9914328-A2, (Mar. 25, 1999), Wood W.I., et al.

Dayhoff, P_AAY08064, WO9914241-A2, (Mar. 25, 1999), Fong S., et al.

Dayhoff, P_AAY88571, WO200015666-A2, (Mar. 23, 2000), Goddard A., et al.

Dayhoff, P_AAB61233, WO200100638-A2, (Jan. 4, 2001), Kirst S.J., et al.

Dayhoff, P_AAH02894.114, PNAS (2002), Strausberg, R.L., et al.

Dayhoff, P_AAB42711, WO200058473-A2, (Oct. 5, 200), Shimkets R.A., et al.

Dayhoff, P_AAY91870, WO200017236-A2, (Mar. 30, 200), Khodadoust, M.M.

GenBank, P_AAC97409, WO200053753-A2, (Jan. 5, 2000), Ashkenazi, A.J., et al.

GenBank, P_AAF72371, WO200104311-A1, (Feb. 22, 2000), Ashkenazi, A.J., et al.

GenBank, P_AAF60360, WO200105836-A1, (Dec. 20, 1999), Botstein, D., et al.

GenBank, P_AAZ93700, WO200021996-A2, (Oct. 5, 199), Ashkenazi, A.J., et al.

GenBank,, P_AAA30040, WO200015666-A2, (Sep. 8, 1999), Goddard, A., et al.

GenBank, P_AAA54089, WO200055319-A1, (Dec. 2, 1999), Ashkenazi, A.J., et al.

GenBank,, P_AAX28433, WO9914327-A2, (Sep. 10, 1998), Botstein, D., et al.

GenBank,, P_AAX52213, WO9914328-A2, (Sep. 16, 199), Wood, W.I., et al.

GenBank, P_AAX37671, WO9914241-A2, (Sep. 17, 1998), Fong, S., et al.

GenBank, AX076909, WO 0105836-A 21, (Jan. 25, 2001), Botstein, D., et al.

GenBank, P_AAF29457, WO200100638-A2, (Jun. 16, 2000), Kirst, S.J., et al.

GenBank, P_AAA08503, WO200017236-A2, (Sep. 24, 1999), Khodadoust, M.M.

GenBank, P_AAC76920, WO200058473-A2, (Mar. 31, 200), Shimkets, R.A., et al.

Hyman, E., et al., "Impact of DNA amplification on gene expression patterns in breast cancer [1,2]" Cancer Research 62 6240-6245, Nov. 2002.

Orntoft, Torben F., et al., "Genome-wide study of gene copy numbers, transcript, and protein levels in Paris of non-invasive and invasive human transitional cell carcinomas", Molecular & Cellular Proteomics, 1:37-45. (2002).

Pollack, J., et al., "Microarray analysis reveals a major direct role of DNA copy number alteration in the transcriptional program of human breast tumors", PNAS vol. 99, 20:12963-12968, Oct. 2002.

Pennica et al., 1998, PNAS, vol. 95, pp. 14717-14722.

Konopka et al., 1986, PNAS, vol. 86, pp. 4049-4052.

Hu et al., journal of Proteome Research, 2 pp. 405-412.

GenBank Accession No. AA177029; National Cancer Institute, Cancer Genome Anatomy Project, Tumor Gene Index; Unpublished (1997); NCI-CGAP.

GenBank Accession No. AA177023; National Cancer Institute, Cancer Genome Anatomy Project, Tumor Gene Index; Unpublished (1997); NCI-CGAP.

GenBank Accession No. AA176975; National Cancer Institute, Cancer Genome Anatomy Project, Tumor Gene Index; Unpublished (1997); NCI-CGAP.

GenBank Accession No. AA220214; Identification of sequence-tagged transcripts differentially expressed within the human hematopoietic hierarchy, Genomics 50(1):44-52 (1998); Claudio, J.O., et al.

GenBank Accession No. AA214585; WashU-NCI human EST Project; Unpublished (1997); Hillier, L., et al.

GenBank Accession No. AA194498; WashU-NCI human EST Project; Unpublished (1997); Hillier, L., et al.

GenBank Accession No. AA161431; WashU-NCI human EST Project; Unpublished (1997); Hillier, L., et al.

GenBank Accession No. AA232350; WashU-NCI human EST Project; Unpublished (1997); Hillier, L., et al.

GenBank Accession No. AA164446; WashU-NCI human EST Project; Unpublished (1997); Hillier, L., et al.

GenBank Accession No. AA516500; National Cancer Institute, Cancer Genome Anatomy Project, Tumor Gene Index; Unpublished (1997); NCI-CGAP.

GenBank Accession No. AA516492; National Cancer Institute, Cancer Genome Anatomy Project, Tumor Gene Index; Unpublished (1997); NCI-CGAP.

GenBank Accession No. AA084788; Generation and analysis of 280,000 human expressed sequence tags; Genome Res. 6 (9), 807-828 (1996); Hillier,L., et al.

GenBank Accession No. AA084416; Generation and analysis of 280,000 human expressed sequence tags; Genome Res. 6 (9), 807-828 (1996); Hillier,L., et al.

GenBank Accession No. AA079482; Generation and analysis of 280,000 human expressed sequence tags; Genome Res. 6 (9), 807-828 (1996); Hillier,L., et al.

GenBank Accession No. AA075763; Generation and analysis of 280,000 human expressed sequence tags; Genome Res. 6 (9), 807-828 (1996); Hillier,L., et al.

GenBank Accession No. AA075497; Generation and analysis of 280,000 human expressed sequence tags; Genome Res. 6 (9), 807-828 (1996); Hillier,L., et al.

GenBank Accession No. AA074670; Generation and analysis of 280,000 human expressed sequence tags; Genome Res. 6 (9), 807-828 (1996); Hillier,L., et al.

GenBank Accession No. AA074069; Generation and analysis of 280,000 human expressed sequence tags; Genome Res. 6 (9), 807-828 (1996); Hillier,L., et al.

GenBank Accession No. AA064897; Generation and analysis of 280,000 human expressed sequence tags; Genome Res. 6 (9), 807-828 (1996); Hillier,L., et al.

GenBank Accession No. AA548400; National Cancer Institute, Cancer Genome Anatomy Project, Tumor Gene Index; Unpublished (1997); NCI-CGAP.

GenBank Accession No. AA146624; WashU-NCI human EST Project; Unpublished (1997); Hillier, L., et al.

GenBank Accession No. AA143555; WashU-NCI human EST Project; Unpublished (1997); Hillier, L., et al.

GenBank Accession No. AA428515; WashU-Merck EST Project 1997; Unpublished 1997; Hillier,L., et al.

GenBank Accession No. AA428367; WashU-Merck EST Project 1997; Unpublished 1997; Hillier,L., et al.

GenBank Accession No. AA424847; WashU-Merck EST Project 1997; Unpublished 1997; Hillier,L., et al.

GenBank Accession No. AA426627; WashU-Merck EST Project 1997; Unpublished 1997; Hillier,L., et al.
GenBank Accession No. AA425667; WashU-Merck EST Project 1997; Unpublished 1997; Hillier,L., et al.
GenBank Accession No. AA425394; WashU-Merck EST Project 1997; Unpublished 1997; Hillier,L., et al.
GenBank Accession No. AA425242; WashU-Merck EST Project 1997; Unpublished 1997; Hillier,L., et al.
GenBank Accession No. AA424647; WashU-Merck EST Project 1997; Unpublished 1997; Hillier,L., et al.
GenBank Accession No. AA424594; WashU-Merck EST Project 1997; Unpublished 1997; Hillier,L., et al.
GenBank Accession No. AA424593; WashU-Merck EST Project 1997; Unpublished 1997; Hillier,L., et al.
GenBank Accession No. AA424244; WashU-Merck EST Project 1997; Unpublished 1997; Hillier,L., et al.
GenBank Accession No. AA420826; National Cancer Institute, Cancer Genome Anatomy Project, Tumor Gene Index; Unpublished (1997); NCI-CGAP.
GenBank Accession No. AA420686; National Cancer Institute, Cancer Genome Anatomy Project, Tumor Gene Index; Unpublished (1997); NCI-CGAP.
GenBank Accession No. AA420697; National Cancer Institute, Cancer Genome Anatomy Project, Tumor Gene Index; Unpublished (1997); NCI-CGAP.
GenBank Accession No. AA420657; National Cancer Institute, Cancer Genome Anatomy Project, Tumor Gene Index; Unpublished (1997); NCI-CGAP.
GenBank Accession No. AA420633; National Cancer Institute, Cancer Genome Anatomy Project, Tumor Gene Index; Unpublished (1997); NCI-CGAP.
GenBank Accession No. AA420632; National Cancer Institute, Cancer Genome Anatomy Project, Tumor Gene Index; Unpublished (1997); NCI-CGAP.
GenBank Accession No. AA420631; National Cancer Institute, Cancer Genome Anatomy Project, Tumor Gene Index; Unpublished (1997); NCI-CGAP.
GenBank Accession No. AA588270; National Cancer Institute, Cancer Genome Anatomy Project, Tumor Gene Index; Unpublished (1997); NCI-CGAP.
GenBank Accession No. AA588853; National Cancer Institute, Cancer Genome Anatomy Project, Tumor Gene Index; Unpublished (1997); NCI-CGAP.
GenBank Accession No. AA588630; National Cancer Institute, Cancer Genome Anatomy Project, Tumor Gene Index; Unpublished (1997); NCI-CGAP.
GenBank Accession No. AA587824; National Cancer Institute, Cancer Genome Anatomy Project, Tumor Gene Index; Unpublished (1997); NCI-CGAP.
GenBank Accession No. AA523005; National Cancer Institute, Cancer Genome Anatomy Project, Tumor Gene Index; Unpublished (1997); NCI-CGAP.
GenBank Accession No. AA523594; National Cancer Institute, Cancer Genome Anatomy Project, Tumor Gene Index; Unpublished (1997); NCI-CGAP.
GenBank Accession No. AA579699; National Cancer Institute, Cancer Genome Anatomy Project, Tumor Gene Index; Unpublished (1997); NCI-CGAP.
GenBank Accession No. AA579351; National Cancer Institute, Cancer Genome Anatomy Project, Tumor Gene Index; Unpublished (1997); NCI-CGAP.
GenBank Accession No. AA579008; National Cancer Institute, Cancer Genome Anatomy Project, Tumor Gene Index; Unpublished (1997); NCI-CGAP.
GenBank Accession No. AA579004; National Cancer Institute, Cancer Genome Anatomy Project, Tumor Gene Index; Unpublished (1997); NCI-CGAP.
GenBank Accession No. AA578799; National Cancer Institute, Cancer Genome Anatomy Project, Tumor Gene Index; Unpublished (1997); NCI-CGAP.
GenBank Accession No. AA578701; National Cancer Institute, Cancer Genome Anatomy Project, Tumor Gene Index; Unpublished (1997); NCI-CGAP.
GenBank Accession No. AA578503; National Cancer Institute, Cancer Genome Anatomy Project, Tumor Gene Index; Unpublished (1997); NCI-CGAP.
GenBank Accession No. AA577416; National Cancer Institute, Cancer Genome Anatomy Project, Tumor Gene Index; Unpublished (1997); NCI-CGAP.
GenBank Accession No. AA574273; National Cancer Institute, Cancer Genome Anatomy Project, Tumor Gene Index; Unpublished (1997); NCI-CGAP.
GenBank Accession No. AA574212; National Cancer Institute, Cancer Genome Anatomy Project, Tumor Gene Index; Unpublished (1997); NCI-CGAP.
GenBank Accession No. AA574209; National Cancer Institute, Cancer Genome Anatomy Project, Tumor Gene Index; Unpublished (1997); NCI-CGAP.
GenBank Accession No. AA574208; National Cancer Institute, Cancer Genome Anatomy Project, Tumor Gene Index; Unpublished (1997); NCI-CGAP.
GenBank Accession No. AA573133; National Cancer Institute, Cancer Genome Anatomy Project, Tumor Gene Index; Unpublished (1997); NCI-CGAP.
GenBank Accession No. AA572857; National Cancer Institute, Cancer Genome Anatomy Project, Tumor Gene Index; Unpublished (1997); NCI-CGAP.
GenBank Accession No. AA558248; National Cancer Institute, Cancer Genome Anatomy Project, Tumor Gene Index; Unpublished (1997); NCI-CGAP.
GenBank Accession No. AA585436; Human HTCDL1 library cDNAs; Unpublished 1994; Sohn,U., et al.
GenBank Accession No. AA585429; Human HTCDL1 library cDNAs; Unpublished 1994; Sohn,U., et al.
GenBank Accession No. AA585354; Human HTCDL1 library cDNAs; Unpublished 1994; Sohn,U., et al.
GenBank Accession No. C75005; Large scale collection of expressed sequence tags (ESTs) from human pancreatic islet cDNA library; Unpublished (1997); Takeda,J.
GenBank Accession No. AA568630; National Cancer Institute, Cancer Genome Anatomy Project, Tumor Gene Index; Unpublished (1997); NCI-CGAP.
GenBank Accession No. AA558634; National Cancer Institute, Cancer Genome Anatomy Project, Tumor Gene Index; Unpublished (1997); NCI-CGAP.
GenBank Accession No. AA557804; National Cancer Institute, Cancer Genome Anatomy Project, Tumor Gene Index; Unpublished (1997); NCI-CGAP.
GenBank Accession No. AA557784; National Cancer Institute, Cancer Genome Anatomy Project, Tumor Gene Index; Unpublished (1997); NCI-CGAP.
GenBank Accession No. AA554999; National Cancer Institute, Cancer Genome Anatomy Project, Tumor Gene Index; Unpublished (1997); NCI-CGAP.
GenBank Accession No. AA554644; National Cancer Institute, Cancer Genome Anatomy Project, Tumor Gene Index; Unpublished (1997); NCI-CGAP.
GenBank Accession No. AA553970; National Cancer Institute, Cancer Genome Anatomy Project, Tumor Gene Index; Unpublished (1997); NCI-CGAP.
GenBank Accession No. AA565164; National Cancer Institute, Cancer Genome Anatomy Project, Tumor Gene Index; Unpublished (1997); NCI-CGAP.
GenBank Accession No. AA564108; National Cancer Institute, Cancer Genome Anatomy Project, Tumor Gene Index; Unpublished (1997); NCI-CGAP.
GenBank Accession No. AA552829; National Cancer Institute, Cancer Genome Anatomy Project, Tumor Gene Index; Unpublished (1997); NCI-CGAP.
GenBank Accession No. AA552827; National Cancer Institute, Cancer Genome Anatomy Project, Tumor Gene Index; Unpublished (1997); NCI-CGAP.
GenBank Accession No. AA570614; National Cancer Institute, Cancer Genome Anatomy Project, Tumor Gene Index; Unpublished (1997); NCI-CGAP.

GenBank Accession No. AA551842; National Cancer Institute, Cancer Genome Anatomy Project, Tumor Gene Index; Unpublished (1997); NCI-CGAP.
GenBank Accession No. AA551827; National Cancer Institute, Cancer Genome Anatomy Project, Tumor Gene Index; Unpublished (1997); NCI-CGAP.
GenBank Accession No. AA551825; National Cancer Institute, Cancer Genome Anatomy Project, Tumor Gene Index; Unpublished (1997); NCI-CGAP.
GenBank Accession No. AA551737; National Cancer Institute, Cancer Genome Anatomy Project, Tumor Gene Index; Unpublished (1997); NCI-CGAP.
GenBank Accession No. AA551727; National Cancer Institute, Cancer Genome Anatomy Project, Tumor Gene Index; Unpublished (1997); NCI-CGAP.
GenBank Accession No. AA551698; National Cancer Institute, Cancer Genome Anatomy Project, Tumor Gene Index; Unpublished (1997); NCI-CGAP.
GenBank Accession No. AA551463; National Cancer Institute, Cancer Genome Anatomy Project, Tumor Gene Index; Unpublished (1997); NCI-CGAP.
GenBank Accession No. AA550791; National Cancer Institute, Cancer Genome Anatomy Project, Tumor Gene Index; Unpublished (1997); NCI-CGAP.
GenBank Accession No. AA550722; National Cancer Institute, Cancer Genome Anatomy Project, Tumor Gene Index; Unpublished (1997); NCI-CGAP.
GenBank Accession No. AA548220; National Cancer Institute, Cancer Genome Anatomy Project, Tumor Gene Index; Unpublished (1997); NCI-CGAP.
GenBank Accession No. AA570183; National Cancer Institute, Cancer Genome Anatomy Project, Tumor Gene Index; Unpublished (1997); NCI-CGAP.
GenBank Accession No. AA569556; National Cancer Institute, Cancer Genome Anatomy Project, Tumor Gene Index; Unpublished (1997); NCI-CGAP.
GenBank Accession No. AA569328; National Cancer Institute, Cancer Genome Anatomy Project, Tumor Gene Index; Unpublished (1997); NCI-CGAP.
GenBank Accession No. AA568415; National Cancer Institute, Cancer Genome Anatomy Project, Tumor Gene Index; Unpublished (1997); NCI-CGAP.
GenBank Accession No. AA564966; National Cancer Institute, Cancer Genome Anatomy Project, Tumor Gene Index; Unpublished (1997); NCI-CGAP.
GenBank Accession No. AA564543; National Cancer Institute, Cancer Genome Anatomy Project, Tumor Gene Index; Unpublished (1997); NCI-CGAP.
GenBank Accession No. AA564062; National Cancer Institute, Cancer Genome Anatomy Project, Tumor Gene Index; Unpublished (1997); NCI-CGA.
GenBank Accession No. AA578900; National Cancer Institute, Cancer Genome Anatomy Project, Tumor Gene Index; Unpublished (1997); NCI-CGA.
GenBank Accession No. AA580026; National Cancer Institute, Cancer Genome Anatomy Project, Tumor Gene Index; Unpublished (1997); NCI-CGA.
GenBank Accession No. AA568108; National Cancer Institute, Cancer Genome Anatomy Project, Tumor Gene Index; Unpublished (1997); NCI-CGA.
GenBank Accession No. AA535922; National Cancer Institute, Cancer Genome Anatomy Project, Tumor Gene Index; Unpublished (1997); NCI-CGA.
GenBank Accession No. AA535763; National Cancer Institute, Cancer Genome Anatomy Project, Tumor Gene Index; Unpublished (1997); NCI-CGA.
GenBank Accession No. AA535744; National Cancer Institute, Cancer Genome Anatomy Project, Tumor Gene Index; Unpublished (1997); NCI-CGA.
GenBank Accession No. AA535559; National Cancer Institute, Cancer Genome Anatomy Project, Tumor Gene Index; Unpublished (1997); NCI-CGA.
GenBank Accession No. AA535497: National Cancer Institute, Cancer Genome Anatomy Project, Tumor Gene Index; Unpublished (1997); NCI-CGA.
GenBank Accession No. AA535462; National Cancer Institute, Cancer Genome Anatomy Project, Tumor Gene Index; Unpublished (1997); NCI-CGA.
GenBank Accession No. AA534256; National Cancer Institute, Cancer Genome Anatomy Project, Tumor Gene Index; Unpublished (1997); NCI-CGA.
GenBank Accession No. AA534135; National Cancer Institute, Cancer Genome Anatomy Project, Tumor Gene Index; Unpublished (1997); NCI-CGA.
GenBank Accession No. AA534087; National Cancer Institute, Cancer Genome Anatomy Project, Tumor Gene Index; Unpublished (1997); NCI-CGA.
GenBank Accession No. AA533961; National Cancer Institute, Cancer Genome Anatomy Project, Tumor Gene Index; Unpublished (1997); NCI-CGA.
GenBank Accession No. AA533211; National Cancer Institute, Cancer Genome Anatomy Project, Tumor Gene Index; Unpublished (1997); NCI-CGA.
GenBank Accession No. AA533169; National Cancer Institute, Cancer Genome Anatomy Project, Tumor Gene Index; Unpublished (1997); NCI-CGA.
GenBank Accession No. AA533162; National Cancer Institute, Cancer Genome Anatomy Project, Tumor Gene Index; Unpublished (1997); NCI-CGA.
GenBank Accession No. AA533145; National Cancer Institute, Cancer Genome Anatomy Project, Tumor Gene Index; Unpublished (1997); NCI-CGA.
GenBank Accession No. AA533053; National Cancer Institute, Cancer Genome Anatomy Project, Tumor Gene Index; Unpublished (1997); NCI-CGA.
GenBank Accession No. AA533045; National Cancer Institute, Cancer Genome Anatomy Project, Tumor Gene Index; Unpublished (1997); NCI-CGA.
GenBank Accession No. AA533031; National Cancer Institute, Cancer Genome Anatomy Project, Tumor Gene Index; Unpublished (1997); NCI-CGA.
GenBank Accession No. AA533004; National Cancer Institute, Cancer Genome Anatomy Project, Tumor Gene Index; Unpublished (1997); NCI-CGA.
GenBank Accession No. AA532960; National Cancer Institute, Cancer Genome Anatomy Project, Tumor Gene Index; Unpublished (1997); NCI-CGA.
GenBank Accession No. AA532912; National Cancer Institute, Cancer Genome Anatomy Project, Tumor Gene Index; Unpublished (1997); NCI-CGA.
GenBank Accession No. AA532712; National Cancer Institute, Cancer Genome Anatomy Project, Tumor Gene Index; Unpublished (1997); NCI-CGA.
GenBank Accession No. AA532710; National Cancer Institute, Cancer Genome Anatomy Project, Tumor Gene Index; Unpublished (1997); NCI-CGA.
GenBank Accession No. AA532590; National Cancer Institute, Cancer Genome Anatomy Project, Tumor Gene Index; Unpublished (1997); NCI-CGA.
GenBank Accession No. AA532578; National Cancer Institute, Cancer Genome Anatomy Project, Tumor Gene Index; Unpublished (1997); NCI-CGA.
GenBank Accession No. AA532571; National Cancer Institute, Cancer Genome Anatomy Project, Tumor Gene Index; Unpublished (1997); NCI-CGA.
GenBank Accession No. AA532567; National Cancer Institute, Cancer Genome Anatomy Project, Tumor Gene Index; Unpublished (1997); NCI-CGA.
GenBank Accession No. AA532495; National Cancer Institute, Cancer Genome Anatomy Project, Tumor Gene Index; Unpublished (1997); NCI-CGA.
GenBank Accession No. AA532472; National Cancer Institute, Cancer Genome Anatomy Project, Tumor Gene Index; Unpublished (1997); NCI-CGA.

GenBank Accession No. AA532469; National Cancer Institute, Cancer Genome Anatomy Project, Tumor Gene Index; Unpublished (1997); NCI-CGA.
GenBank Accession No. AA229964; National Cancer Institute, Cancer Genome Anatomy Project, Tumor Gene Index; Unpublished (1997); NCI-CGA.
GenBank Accession No. AA230005; National Cancer Institute, Cancer Genome Anatomy Project, Tumor Gene Index; Unpublished (1997); NCI-CGA.
GenBank Accession No. AA229092; National Cancer Institute, Cancer Genome Anatomy Project, Tumor Gene Index; Unpublished (1997); NCI-CGA.
GenBank Accession No. AA229756; National Cancer Institute, Cancer Genome Anatomy Project, Tumor Gene Index; Unpublished (1997); NCI-CGA.
GenBank Accession No. AA228949; National Cancer Institute, Cancer Genome Anatomy Project, Tumor Gene Index; Unpublished (1997); NCI-CGA.
GenBank Accession No. AA228948; National Cancer Institute, Cancer Genome Anatomy Project, Tumor Gene Index; Unpublished (1997); NCI-CGA.
GenBank Accession No. AA229223; National Cancer Institute, Cancer Genome Anatomy Project, Tumor Gene Index; Unpublished (1997); NCI-CGA.
GenBank Accession No. AA229222; National Cancer Institute, Cancer Genome Anatomy Project, Tumor Gene Index; Unpublished (1997); NCI-CGA.
GenBank Accession No. AA226623; National Cancer Institute, Cancer Genome Anatomy Project, Tumor Gene Index; Unpublished (1997); NCI-CGA.
GenBank Accession No. AA226556; National Cancer Institute, Cancer Genome Anatomy Project, Tumor Gene Index; Unpublished (1997); NCI-CGA.
GenBank Accession No. AA226240; National Cancer Institute, Cancer Genome Anatomy Project, Tumor Gene Index; Unpublished (1997); NCI-CGA.
GenBank Accession No. AA226227; National Cancer Institute, Cancer Genome Anatomy Project, Tumor Gene Index; Unpublished (1997); NCI-CGA.
GenBank Accession No. AA224934; National Cancer Institute, Cancer Genome Anatomy Project, Tumor Gene Index; Unpublished (1997); NCI-CGA.
GenBank Accession No. AA224959; National Cancer Institute, Cancer Genome Anatomy Project, Tumor Gene Index; Unpublished (1997); NCI-CGA.
GenBank Accession No. AA535733; National Cancer Institute, Cancer Genome Anatomy Project, Tumor Gene Index; Unpublished (1997); NCI-CGA.
GenBank Accession No. AA531498; National Cancer Institute, Cancer Genome Anatomy Project, Tumor Gene Index; Unpublished (1997); NCI-CGA.
GenBank Accession No. AA531381; National Cancer Institute, Cancer Genome Anatomy Project, Tumor Gene Index; Unpublished (1997); NCI-CGA.
GenBank Accession No. AA531361; National Cancer Institute, Cancer Genome Anatomy Project, Tumor Gene Index; Unpublished (1997); NCI-CGA.
GenBank Accession No. AA531341; National Cancer Institute, Cancer Genome Anatomy Project, Tumor Gene Index; Unpublished (1997); NCI-CGA.
GenBank Accession No. AA531328; National Cancer Institute, Cancer Genome Anatomy Project, Tumor Gene Index; Unpublished (1997); NCI-CGA.
GenBank Accession No. AA531238; National Cancer Institute, Cancer Genome Anatomy Project, Tumor Gene Index; Unpublished (1997); NCI-CGA.
GenBank Accession No. AA531208; National Cancer Institute, Cancer Genome Anatomy Project, Tumor Gene Index; Unpublished (1997); NCI-CGA.
GenBank Accession No. AA531202; National Cancer Institute, Cancer Genome Anatomy Project, Tumor Gene Index; Unpublished (1997); NCI-CGA.
GenBank Accession No. AA530974; National Cancer Institute, Cancer Genome Anatomy Project, Tumor Gene Index; Unpublished (1997); NCI-CGA.
GenBank Accession No. AA530954; National Cancer Institute, Cancer Genome Anatomy Project, Tumor Gene Index; Unpublished (1997); NCI-CGA.
GenBank Accession No. AA530942; National Cancer Institute, Cancer Genome Anatomy Project, Tumor Gene Index; Unpublished (1997); NCI-CGA.
GenBank Accession No. AA530939; National Cancer Institute, Cancer Genome Anatomy Project, Tumor Gene Index; Unpublished (1997); NCI-CGA.
GenBank Accession No. AA530931; National Cancer Institute, Cancer Genome Anatomy Project, Tumor Gene Index; Unpublished (1997); NCI-CGA.
GenBank Accession No. AA530906; National Cancer Institute, Cancer Genome Anatomy Project, Tumor Gene Index; Unpublished (1997); NCI-CGA.
GenBank Accession No. AA530882; National Cancer Institute, Cancer Genome Anatomy Project, Tumor Gene Index; Unpublished (1997); NCI-CGA.
GenBank Accession No. AA527825; National Cancer Institute, Cancer Genome Anatomy Project, Tumor Gene Index; Unpublished (1997); NCI-CGA.
GenBank Accession No. AA521423; National Cancer Institute, Cancer Genome Anatomy Project, Tumor Gene Index; Unpublished (1997); NCI-CGA.
GenBank Accession No. AA514915; National Cancer Institute, Cancer Genome Anatomy Project, Tumor Gene Index; Unpublished (1997); NCI-CGA.
GenBank Accession No. AA514888; National Cancer Institute, Cancer Genome Anatomy Project, Tumor Gene Index; Unpublished (1997); NCI-CGA.
GenBank Accession No. AA514804; National Cancer Institute, Cancer Genome Anatomy Project, Tumor Gene Index; Unpublished (1997); NCI-CGA.
GenBank Accession No. AA507281; National Cancer Institute, Cancer Genome Anatomy Project, Tumor Gene Index; Unpublished (1997); NCI-CGA.
GenBank Accession No. AA507230; National Cancer Institute, Cancer Genome Anatomy Project, Tumor Gene Index; Unpublished (1997); NCI-CGA.
GenBank Accession No. AA507217; National Cancer Institute, Cancer Genome Anatomy Project, Tumor Gene Index; Unpublished (1997); NCI-CGA.
GenBank Accession No. AA507215; National Cancer Institute, Cancer Genome Anatomy Project, Tumor Gene Index; Unpublished (1997); NCI-CGA.
GenBank Accession No. AA507128; National Cancer Institute, Cancer Genome Anatomy Project, Tumor Gene Index; Unpublished (1997); NCI-CGA.
GenBank Accession No. AA507093; National Cancer Institute, Cancer Genome Anatomy Project, Tumor Gene Index; Unpublished (1997); NCI-CGA.
GenBank Accession No. AA506914; National Cancer Institute, Cancer Genome Anatomy Project, Tumor Gene Index; Unpublished (1997); NCI-CGA.
GenBank Accession No. AA506804; National Cancer Institute, Cancer Genome Anatomy Project, Tumor Gene Index; Unpublished (1997); NCI-CGA.
GenBank Accession No. AA506731; National Cancer Institute, Cancer Genome Anatomy Project, Tumor Gene Index; Unpublished (1997); NCI-CGA.
GenBank Accession No. AA506377; National Cancer Institute, Cancer Genome Anatomy Project, Tumor Gene Index; Unpublished (1997); NCI-CGA.
GenBank Accession No. AA506330; National Cancer Institute, Cancer Genome Anatomy Project, Tumor Gene Index; Unpublished (1997); NCI-CGA.
GenBank Accession No. AA506319; National Cancer Institute, Cancer Genome Anatomy Project, Tumor Gene Index; Unpublished (1997); NCI-CGA.

GenBank Accession No. AA506197; National Cancer Institute, Cancer Genome Anatomy Project, Tumor Gene Index; Unpublished (1997); NCI-CGA.
GenBank Accession No. AA504066; National Cancer Institute, Cancer Genome Anatomy Project, Tumor Gene Index; Unpublished (1997); NCI-CGA.
GenBank Accession No. AA504051; National Cancer Institute, Cancer Genome Anatomy Project, Tumor Gene Index; Unpublished (1997); NCI-CGA.
GenBank Accession No. AA504003; National Cancer Institute, Cancer Genome Anatomy Project, Tumor Gene Index; Unpublished (1997); NCI-CGA.
GenBank Accession No. AA503926; National Cancer Institute, Cancer Genome Anatomy Project, Tumor Gene Index; Unpublished (1997); NCI-CGA.
GenBank Accession No. AA503909; National Cancer Institute, Cancer Genome Anatomy Project, Tumor Gene Index; Unpublished (1997); NCI-CGA.
GenBank Accession No. AA503349; National Cancer Institute, Cancer Genome Anatomy Project, Tumor Gene Index; Unpublished (1997); NCI-CGA.
GenBank Accession No. AA502078; National Cancer Institute, Cancer Genome Anatomy Project, Tumor Gene Index; Unpublished (1997); NCI-CGA.
GenBank Accession No. AA493519; National Cancer Institute, Cancer Genome Anatomy Project, Tumor Gene Index; Unpublished (1997); NCI-CGA.
GenBank Accession No. AA493332; National Cancer Institute, Cancer Genome Anatomy Project, Tumor Gene Index; Unpublished (1997); NCI-CGA.
GenBank Accession No. AA493268; National Cancer Institute, Cancer Genome Anatomy Project, Tumor Gene Index; Unpublished (1997); NCI-CGA.
GenBank Accession No. AA494246; National Cancer Institute, Cancer Genome Anatomy Project, Tumor Gene Index; Unpublished (1997); NCI-CGA.
GenBank Accession No. AA494242; National Cancer Institute, Cancer Genome Anatomy Project, Tumor Gene Index; Unpublished (1997); NCI-CGA.
GenBank Accession No. AA492451; National Cancer Institute, Cancer Genome Anatomy Project, Tumor Gene Index; Unpublished (1997); NCI-CGA.
GenBank Accession No. AA492445; National Cancer Institute, Cancer Genome Anatomy Project, Tumor Gene Index; Unpublished (1997); NCI-CGA.
GenBank Accession No. AA492438; National Cancer Institute, Cancer Genome Anatomy Project, Tumor Gene Index; Unpublished (1997); NCI-CGA.
GenBank Accession No. AA244480; National Cancer Institute, Cancer Genome Anatomy Project, Tumor Gene Index; Unpublished (1997); NCI-CGA.
GenBank Accession No. AA244452; National Cancer Institute, Cancer Genome Anatomy Project, Tumor Gene Index; Unpublished (1997); NCI-CGA.
GenBank Accession No. AA244432; National Cancer Institute, Cancer Genome Anatomy Project, Tumor Gene Index; Unpublished (1997); NCI-CGA.
GenBank Accession No. AA244362; National Cancer Institute, Cancer Genome Anatomy Project, Tumor Gene Index; Unpublished (1997); NCI-CGA.
GenBank Accession No. AA244052; National Cancer Institute, Cancer Genome Anatomy Project, Tumor Gene Index; Unpublished (1997); NCI-CGA.
GenBank Accession No. AA244289; National Cancer Institute, Cancer Genome Anatomy Project, Tumor Gene Index; Unpublished (1997); NCI-CGA.
GenBank Accession No. AA244178; National Cancer Institute, Cancer Genome Anatomy Project, Tumor Gene Index; Unpublished (1997); NCI-CGA.
GenBank Accession No. AA244091; National Cancer Institute, Cancer Genome Anatomy Project, Tumor Gene Index; Unpublished (1997); NCI-CGA.
GenBank Accession No. AA244074; National Cancer Institute, Cancer Genome Anatomy Project, Tumor Gene Index; Unpublished (1997); NCI-CGA.
GenBank Accession No. AA244017; National Cancer Institute, Cancer Genome Anatomy Project, Tumor Gene Index; Unpublished (1997); NCI-CGA.
GenBank Accession No. AA229482; National Cancer Institute, Cancer Genome Anatomy Project, Tumor Gene Index; Unpublished (1997); NCI-CGA.
GenBank Accession No. AA225974; National Cancer Institute, Cancer Genome Anatomy Project, Tumor Gene Index; Unpublished (1997); NCI-CGA.
GenBank Accession No. AA225963; National Cancer Institute, Cancer Genome Anatomy Project, Tumor Gene Index; Unpublished (1997); NCI-CGA.
GenBank Accession No. AA225880; National Cancer Institute, Cancer Genome Anatomy Project, Tumor Gene Index; Unpublished (1997); NCI-CGA.
GenBank Accession No. AA225879; National Cancer Institute, Cancer Genome Anatomy Project, Tumor Gene Index; Unpublished (1997); NCI-CGA.
GenBank Accession No. AA225381; National Cancer Institute, Cancer Genome Anatomy Project, Tumor Gene Index; Unpublished (1997); NCI-CGA.
GenBank Accession No. AA225409; National Cancer Institute, Cancer Genome Anatomy Project, Tumor Gene Index; Unpublished (1997); NCI-CGA.
GenBank Accession No. AA225213; National Cancer Institute, Cancer Genome Anatomy Project, Tumor Gene Index; Unpublished (1997); NCI-CGA.
GenBank Accession No. AA225322; National Cancer Institute, Cancer Genome Anatomy Project, Tumor Gene Index; Unpublished (1997); NCI-CGA.
GenBank Accession No. AA225308; National Cancer Institute, Cancer Genome Anatomy Project, Tumor Gene Index; Unpublished (1997); NCI-CGA.
GenBank Accession No. AA225228; National Cancer Institute, Cancer Genome Anatomy Project, Tumor Gene Index; Unpublished (1997); NCI-CGA.
GenBank Accession No. AA225152; National Cancer Institute, Cancer Genome Anatomy Project, Tumor Gene Index; Unpublished (1997); NCI-CGA.
GenBank Accession No. AA225206; National Cancer Institute, Cancer Genome Anatomy Project, Tumor Gene Index; Unpublished (1997); NCI-CGA.
GenBank Accession No. AA225143; National Cancer Institute, Cancer Genome Anatomy Project, Tumor Gene Index; Unpublished (1997); NCI-CGA.
GenBank Accession No. AA216404; National Cancer Institute, Cancer Genome Anatomy Project, Tumor Gene Index; Unpublished (1997); NCI-CGA.
GenBank Accession No. AA541768; National Cancer Institute, Cancer Genome Anatomy Project, Tumor Gene Index; Unpublished (1997); NCI-CGA.
GenBank Accession No. AA541642; National Cancer Institute, Cancer Genome Anatomy Project, Tumor Gene Index; Unpublished (1997); NCI-CGA.
GenBank Accession No. AA541611; National Cancer Institute, Cancer Genome Anatomy Project, Tumor Gene Index; Unpublished (1997); NCI-CGA.
GenBank Accession No. AA541576; National Cancer Institute, Cancer Genome Anatomy Project, Tumor Gene Index; Unpublished (1997); NCI-CGA.
GenBank Accession No. AA515982; National Cancer Institute, Cancer Genome Anatomy Project, Tumor Gene Index; Unpublished (1997); NCI-CGA.
GenBank Accession No. AA513240; National Cancer Institute, Cancer Genome Anatomy Project, Tumor Gene Index; Unpublished (1997); NCI-CGA.
GenBank Accession No. AA508144; National Cancer Institute, Cancer Genome Anatomy Project, Tumor Gene Index; Unpublished (1997); NCI-CGA.

GenBank Accession No. AA503689; National Cancer Institute, Cancer Genome Anatomy Project, Tumor Gene Index; Unpublished (1997); NCI-CGA.
GenBank Accession No. AA503688; National Cancer Institute, Cancer Genome Anatomy Project, Tumor Gene Index; Unpublished (1997); NCI-CGA.
GenBank Accession No. AA503682; National Cancer Institute, Cancer Genome Anatomy Project, Tumor Gene Index; Unpublished (1997); NCI-CGA.
GenBank Accession No. AA503677; National Cancer Institute, Cancer Genome Anatomy Project, Tumor Gene Index; Unpublished (1997); NCI-CGA.
GenBank Accession No. AA503340; National Cancer Institute, Cancer Genome Anatomy Project, Tumor Gene Index; Unpublished (1997); NCI-CGA.
GenBank Accession No. AA503064; National Cancer Institute, Cancer Genome Anatomy Project, Tumor Gene Index; Unpublished (1997); NCI-CGA.
GenBank Accession No. AA502978; National Cancer Institute, Cancer Genome Anatomy Project, Tumor Gene Index; Unpublished (1997); NCI-CGA.
GenBank Accession No. AA492429; National Cancer Institute, Cancer Genome Anatomy Project, Tumor Gene Index; Unpublished (1997); NCI-CGA.
GenBank Accession No. AA492411; National Cancer Institute, Cancer Genome Anatomy Project, Tumor Gene Index; Unpublished (1997); NCI-CGA.
GenBank Accession No. AA492389; National Cancer Institute, Cancer Genome Anatomy Project, Tumor Gene Index; Unpublished (1997); NCI-CGA.
GenBank Accession No. AA492382; National Cancer Institute, Cancer Genome Anatomy Project, Tumor Gene Index; Unpublished (1997); NCI-CGA.
GenBank Accession No. AA492334; National Cancer Institute, Cancer Genome Anatomy Project, Tumor Gene Index; Unpublished (1997); NCI-CGA.
GenBank Accession No. AA492329; National Cancer Institute, Cancer Genome Anatomy Project, Tumor Gene Index; Unpublished (1997); NCI-CGA.
GenBank Accession No. AA492327; National Cancer Institute, Cancer Genome Anatomy Project, Tumor Gene Index; Unpublished (1997); NCI-CGA.
GenBank Accession No. AA492312; National Cancer Institute, Cancer Genome Anatomy Project, Tumor Gene Index; Unpublished (1997); NCI-CGA.
GenBank Accession No. AA492311; National Cancer Institute, Cancer Genome Anatomy Project, Tumor Gene Index; Unpublished (1997); NCI-CGA.
GenBank Accession No. AA492295; National Cancer Institute, Cancer Genome Anatomy Project, Tumor Gene Index; Unpublished (1997); NCI-CGA.
GenBank Accession No. AA492255; National Cancer Institute, Cancer Genome Anatomy Project, Tumor Gene Index; Unpublished (1997); NCI-CGA.
GenBank Accession No. AA226160; National Cancer Institute, Cancer Genome Anatomy Project, Tumor Gene Index; Unpublished (1997); NCI-CGA.
GenBank Accession No. AA225625; National Cancer Institute, Cancer Genome Anatomy Project, Tumor Gene Index; Unpublished (1997); NCI-CGA.
GenBank Accession No. AA515104; National Cancer Institute, Cancer Genome Anatomy Project, Tumor Gene Index; Unpublished (1997); NCI-CGA.
GenBank Accession No. AA508636; National Cancer Institute, Cancer Genome Anatomy Project, Tumor Gene Index; Unpublished (1997); NCI-CGA.
GenBank Accession No. AA508432; National Cancer Institute, Cancer Genome Anatomy Project, Tumor Gene Index; Unpublished (1997); NCI-CGA.
GenBank Accession No. AA508367; National Cancer Institute, Cancer Genome Anatomy Project, Tumor Gene Index; Unpublished (1997); NCI-CGA.
GenBank Accession No. AA508360; National Cancer Institute, Cancer Genome Anatomy Project, Tumor Gene Index; Unpublished (1997); NCI-CGA.
GenBank Accession No. AA508348; National Cancer Institute, Cancer Genome Anatomy Project, Tumor Gene Index; Unpublished (1997); NCI-CGA.
GenBank Accession No. AA508128; National Cancer Institute, Cancer Genome Anatomy Project, Tumor Gene Index; Unpublished (1997); NCI-CGA.
GenBank Accession No. AA508112; National Cancer Institute, Cancer Genome Anatomy Project, Tumor Gene Index; Unpublished (1997); NCI-CGA.
GenBank Accession No. AA508096; National Cancer Institute, Cancer Genome Anatomy Project, Tumor Gene Index; Unpublished (1997); NCI-CGA.
GenBank Accession No. AA508078; National Cancer Institute, Cancer Genome Anatomy Project, Tumor Gene Index; Unpublished (1997); NCI-CGA.
GenBank Accession No. AA508013; National Cancer Institute, Cancer Genome Anatomy Project, Tumor Gene Index; Unpublished (1997); NCI-CGA.
GenBank Accession No. AA507996; National Cancer Institute, Cancer Genome Anatomy Project, Tumor Gene Index; Unpublished (1997); NCI-CGA.
GenBank Accession No. AA507995; National Cancer Institute, Cancer Genome Anatomy Project, Tumor Gene Index; Unpublished (1997); NCI-CGA.
GenBank Accession No. AA507983; National Cancer Institute, Cancer Genome Anatomy Project, Tumor Gene Index; Unpublished (1997); NCI-CGA.
GenBank Accession No. AA507968; National Cancer Institute, Cancer Genome Anatomy Project, Tumor Gene Index; Unpublished (1997); NCI-CGA.
GenBank Accession No. AA507373; National Cancer Institute, Cancer Genome Anatomy Project, Tumor Gene Index; Unpublished (1997); NCI-CGA.
GenBank Accession No. AA507370; National Cancer Institute, Cancer Genome Anatomy Project, Tumor Gene Index; Unpublished (1997); NCI-CGA.
GenBank Accession No. AA507369; National Cancer Institute, Cancer Genome Anatomy Project, Tumor Gene Index; Unpublished (1997); NCI-CGA.
GenBank Accession No. AA507305; National Cancer Institute, Cancer Genome Anatomy Project, Tumor Gene Index; Unpublished (1997); NCI-CGA.
GenBank Accession No. AA507287; National Cancer Institute, Cancer Genome Anatomy Project, Tumor Gene Index; Unpublished (1997); NCI-CGA.
GenBank Accession No. AA506475; National Cancer Institute, Cancer Genome Anatomy Project, Tumor Gene Index; Unpublished (1997); NCI-CGA.
GenBank Accession No. AA503666; National Cancer Institute, Cancer Genome Anatomy Project, Tumor Gene Index; Unpublished (1997); NCI-CGA.
GenBank Accession No. AA503609; National Cancer Institute, Cancer Genome Anatomy Project, Tumor Gene Index; Unpublished (1997); NCI-CGA.
GenBank Accession No. AA503429; National Cancer Institute, Cancer Genome Anatomy Project, Tumor Gene Index; Unpublished (1997); NCI-CGA.
GenBank Accession No. AA503276; National Cancer Institute, Cancer Genome Anatomy Project, Tumor Gene Index; Unpublished (1997); NCI-CGA.
GenBank Accession No. AA503115; National Cancer Institute, Cancer Genome Anatomy Project, Tumor Gene Index; Unpublished (1997); NCI-CGA.
GenBank Accession No. AA502981; National Cancer Institute, Cancer Genome Anatomy Project, Tumor Gene Index; Unpublished (1997); NCI-CGA.
GenBank Accession No. AA502973; National Cancer Institute, Cancer Genome Anatomy Project, Tumor Gene Index; Unpublished (1997); NCI-CGA.

GenBank Accession No. AA502965; National Cancer Institute, Cancer Genome Anatomy Project, Tumor Gene Index; Unpublished (1997); NCI-CGA.
GenBank Accession No. AA502200; National Cancer Institute, Cancer Genome Anatomy Project, Tumor Gene Index; Unpublished (1997); NCI-CGA.
GenBank Accession No. AA502191; National Cancer Institute, Cancer Genome Anatomy Project, Tumor Gene Index; Unpublished (1997); NCI-CGA.
GenBank Accession No. AA502180; National Cancer Institute, Cancer Genome Anatomy Project, Tumor Gene Index; Unpublished (1997); NCI-CGA.
GenBank Accession No. AA502154; National Cancer Institute, Cancer Genome Anatomy Project, Tumor Gene Index; Unpublished (1997); NCI-CGA.
GenBank Accession No. AA502074; National Cancer Institute, Cancer Genome Anatomy Project, Tumor Gene Index; Unpublished (1997); NCI-CGA.
GenBank Accession No. AA502073; National Cancer Institute, Cancer Genome Anatomy Project, Tumor Gene Index; Unpublished (1997); NCI-CGA.
GenBank Accession No. AA502072; National Cancer Institute, Cancer Genome Anatomy Project, Tumor Gene Index; Unpublished (1997); NCI-CGA.
GenBank Accession No. AA502071; National Cancer Institute, Cancer Genome Anatomy Project, Tumor Gene Index; Unpublished (1997); NCI-CGA.
GenBank Accession No. AA493445; National Cancer Institute, Cancer Genome Anatomy Project, Tumor Gene Index; Unpublished (1997); NCI-CGA.
GenBank Accession No. AA494243; National Cancer Institute, Cancer Genome Anatomy Project, Tumor Gene Index; Unpublished (1997); NCI-CGA.
GenBank Accession No. AA492207; National Cancer Institute, Cancer Genome Anatomy Project, Tumor Gene Index; Unpublished (1997); NCI-CGA.
GenBank Accession No. AA492204; National Cancer Institute, Cancer Genome Anatomy Project, Tumor Gene Index; Unpublished (1997); NCI-CGA.
GenBank Accession No. AA492168; National Cancer Institute, Cancer Genome Anatomy Project, Tumor Gene Index; Unpublished (1997); NCI-CGA.
GenBank Accession No. AA492163; National Cancer Institute, Cancer Genome Anatomy Project, Tumor Gene Index; Unpublished (1997); NCI-CGA.
GenBank Accession No. AA507789; National Cancer Institute, Cancer Genome Anatomy Project, Tumor Gene Index; Unpublished (1997); NCI-CGA.
GenBank Accession No. AA507785; National Cancer Institute, Cancer Genome Anatomy Project, Tumor Gene Index; Unpublished (1997); NCI-CGA.
GenBank Accession No. AA507685; National Cancer Institute, Cancer Genome Anatomy Project, Tumor Gene Index; Unpublished (1997); NCI-CGA.
GenBank Accession No. AA507679; National Cancer Institute, Cancer Genome Anatomy Project, Tumor Gene Index; Unpublished (1997); NCI-CGA.
GenBank Accession No. AA507545; National Cancer Institute, Cancer Genome Anatomy Project, Tumor Gene Index; Unpublished (1997); NCI-CGA.
GenBank Accession No. AA470548; National Cancer Institute, Cancer Genome Anatomy Project, Tumor Gene Index; Unpublished (1997); NCI-CGA.
GenBank Accession No. AA470501; National Cancer Institute, Cancer Genome Anatomy Project, Tumor Gene Index; Unpublished (1997); NCI-CGA.
GenBank Accession No. AA468708; National Cancer Institute, Cancer Genome Anatomy Project, Tumor Gene Index; Unpublished (1997); NCI-CGA.
GenBank Accession No. AA282364; National Cancer Institute, Cancer Genome Anatomy Project, Tumor Gene Index; Unpublished (1997); NCI-CGA.
GenBank Accession No. AA226680; National Cancer Institute, Cancer Genome Anatomy Project, Tumor Gene Index; Unpublished (1997); NCI-CGA.
GenBank Accession No. AA226632; National Cancer Institute, Cancer Genome Anatomy Project, Tumor Gene Index; Unpublished (1997); NCI-CGA.
GenBank Accession No. AA226459; National Cancer Institute, Cancer Genome Anatomy Project, Tumor Gene Index; Unpublished (1997); NCI-CGA.
GenBank Accession No. AA226384; National Cancer Institute, Cancer Genome Anatomy Project, Tumor Gene Index; Unpublished (1997); NCI-CGA.
GenBank Accession No. AA226101; National Cancer Institute, Cancer Genome Anatomy Project, Tumor Gene Index; Unpublished (1997); NCI-CGA.
GenBank Accession No. AA226010; National Cancer Institute, Cancer Genome Anatomy Project, Tumor Gene Index; Unpublished (1997); NCI-CGA.
GenBank Accession No. AA225109; National Cancer Institute, Cancer Genome Anatomy Project, Tumor Gene Index; Unpublished (1997); NCI-CGA.
GenBank Accession No. AA225025; National Cancer Institute, Cancer Genome Anatomy Project, Tumor Gene Index; Unpublished (1997); NCI-CGA.
GenBank Accession No. AA507830; National Cancer Institute, Cancer Genome Anatomy Project, Tumor Gene Index; Unpublished (1997); NCI-CGA.
GenBank Accession No. AA507778; National Cancer Institute, Cancer Genome Anatomy Project, Tumor Gene Index; Unpublished (1997); NCI-CGA.
GenBank Accession No. AA507769; National Cancer Institute, Cancer Genome Anatomy Project, Tumor Gene Index; Unpublished (1997); NCI-CGA.
GenBank Accession No. AA507759; National Cancer Institute, Cancer Genome Anatomy Project, Tumor Gene Index; Unpublished (1997); NCI-CGA.
GenBank Accession No. AA282246; National Cancer Institute, Cancer Genome Anatomy Project, Tumor Gene Index; Unpublished (1997); NCI-CGA.
GenBank Accession No. AA281742; National Cancer Institute, Cancer Genome Anatomy Project, Tumor Gene Index; Unpublished (1997); NCI-CGA.
GenBank Accession No. AA177153; National Cancer Institute, Cancer Genome Anatomy Project, Tumor Gene Index; Unpublished (1997); NCI-CGA.
GenBank Accession No. AA176984; National Cancer Institute, Cancer Genome Anatomy Project, Tumor Gene Index; Unpublished (1997); NCI-CGA.
GenBank Accession No. AA508900; National Cancer Institute, Cancer Genome Anatomy Project, Tumor Gene Index; Unpublished (1997); NCI-CGA.
GenBank Accession No. AA507669; National Cancer Institute, Cancer Genome Anatomy Project, Tumor Gene Index; Unpublished (1997); NCI-CGA.
GenBank Accession No. AA507664; National Cancer Institute, Cancer Genome Anatomy Project, Tumor Gene Index; Unpublished (1997); NCI-CGA.
GenBank Accession No. AA507659; National Cancer Institute, Cancer Genome Anatomy Project, Tumor Gene Index; Unpublished (1997); NCI-CGA.
GenBank Accession No. AA507615; National Cancer Institute, Cancer Genome Anatomy Project, Tumor Gene Index; Unpublished (1997); NCI-CGA.
GenBank Accession No. AA469373; National Cancer Institute, Cancer Genome Anatomy Project, Tumor Gene Index; Unpublished (1997); NCI-CGA.
GenBank Accession No. AA469293; National Cancer Institute, Cancer Genome Anatomy Project, Tumor Gene Index; Unpublished (1997); NCI-CGA.
GenBank Accession No. AA469226; National Cancer Institute, Cancer Genome Anatomy Project, Tumor Gene Index; Unpublished (1997); NCI-CGA.

GenBank Accession No. AA469209; National Cancer Institute, Cancer Genome Anatomy Project, Tumor Gene Index; Unpublished (1997); NCI-CGA.
GenBank Accession No. AA469201; National Cancer Institute, Cancer Genome Anatomy Project, Tumor Gene Index; Unpublished (1997); NCI-CGA.
GenBank Accession No. AA469154; National Cancer Institute, Cancer Genome Anatomy Project, Tumor Gene Index; Unpublished (1997); NCI-CGA.
GenBank Accession No. AA469131; National Cancer Institute, Cancer Genome Anatomy Project, Tumor Gene Index; Unpublished (1997); NCI-CGA.
GenBank Accession No. AA397457; National Cancer Institute, Cancer Genome Anatomy Project, Tumor Gene Index; Unpublished (1997); NCI-CGA.
GenBank Accession No. AA256653; National Cancer Institute, Cancer Genome Anatomy Project, Tumor Gene Index; Unpublished (1997); NCI-CGA.
GenBank Accession No. AA2521205; National Cancer Institute, Cancer Genome Anatomy Project, Tumor Gene Index; Unpublished (1997); NCI-CGA.
GenBank Accession No. AA214567; National Cancer Institute, Cancer Genome Anatomy Project, Tumor Gene Index; Unpublished (1997); NCI-CGA.
GenBank Accession No. AA214560; National Cancer Institute, Cancer Genome Anatomy Project, Tumor Gene Index; Unpublished (1997); NCI-CGA.
GenBank Accession No. AA496651; WashU-Merck EST Project 1997; Unpublished 1997; Hillier,L., et al.
GenBank Accession No. AA405143; WashU-Merck EST Project 1997; Unpublished 1997; Hillier,L., et al.
GenBank Accession No. AA399481; WashU-Merck EST Project 1997; Unpublished 1997; Hillier,L., et al.
GenBank Accession No. AA399431; WashU-Merck EST Project 1997; Unpublished 1997; Hillier,L., et al.
GenBank Accession No. AA399327; WashU-Merck EST Project 1997; Unpublished 1997; Hillier,L., et al.
GenBank Accession No. AA398256; WashU-Merck EST Project 1997; Unpublished 1997; Hillier,L., et al.
GenBank Accession No. AA397627; WashU-Merck EST Project 1997; Unpublished 1997; Hillier,L., et al.
GenBank Accession No. AA490376; WashU-Merck EST Project 1997; Unpublished 1997; Hillier,L., et al.
GenBank Accession No. AA490274; WashU-Merck EST Project 1997; Unpublished 1997; Hillier,L., et al.
GenBank Accession No. AA481448; WashU-Merck EST Project 1997; Unpublished 1997; Hillier,L., et al.
GenBank Accession No. AA478083; WashU-Merck EST Project 1997; Unpublished 1997; Hillier,L., et al.
GenBank Accession No. AA476254; WashU-Merck EST Project 1997; Unpublished 1997; Hillier,L., et al.
GenBank Accession No. AA258382; WashU-Merck EST Project 1997; Unpublished 1997; Hillier,L., et al.
GenBank Accession No. AA255421; WashU-Merck EST Project 1997; Unpublished 1997; Hillier,L., et al.
GenBank Accession No. AA256549; WashU-Merck EST Project 1997; Unpublished 1997; Hillier,L., et al.
GenBank Accession No. AA256947; WashU-Merck EST Project 1997; Unpublished 1997; Hillier,L., et al.
GenBank Accession No. AA135071; Generation and analysis of 280,000 human expressed sequence tags; Genome Res. 6 (9), 807-828 (1996); Hillier,L., et al.
GenBank Accession No. AA541455; National Cancer Institute, Cancer Genome Anatomy Project, Tumor Gene Index; Unpublished (1997); NCI-CGA.
GenBank Accession No. AA528273; National Cancer Institute, Cancer Genome Anatomy Project, Tumor Gene Index; Unpublished (1997); NCI-CGA.
GenBank Accession No. AA527734; National Cancer Institute, Cancer Genome Anatomy Project, Tumor Gene Index; Unpublished (1997); NCI-CGA.
GenBank Accession No. AA527728; National Cancer Institute, Cancer Genome Anatomy Project, Tumor Gene Index; Unpublished (1997); NCI-CGA.
GenBank Accession No. AA526493; National Cancer Institute, Cancer Genome Anatomy Project, Tumor Gene Index; Unpublished (1997); NCI-CGA.
GenBank Accession No. AA526491; National Cancer Institute, Cancer Genome Anatomy Project, Tumor Gene Index; Unpublished (1997); NCI-CGA.
GenBank Accession No. AA525091; National Cancer Institute, Cancer Genome Anatomy Project, Tumor Gene Index; Unpublished (1997); NCI-CGA.
GenBank Accession No. AA524998; National Cancer Institute, Cancer Genome Anatomy Project, Tumor Gene Index; Unpublished (1997); NCI-CGA.
GenBank Accession No. AA524914; National Cancer Institute, Cancer Genome Anatomy Project, Tumor Gene Index; Unpublished (1997); NCI-CGA.
GenBank Accession No. AA524675; National Cancer Institute, Cancer Genome Anatomy Project, Tumor Gene Index; Unpublished (1997); NCI-CGA.
GenBank Accession No. AA524439; National Cancer Institute, Cancer Genome Anatomy Project, Tumor Gene Index; Unpublished (1997); NCI-CGA.
GenBank Accession No. AA522599; National Cancer Institute, Cancer Genome Anatomy Project, Tumor Gene Index; Unpublished (1997); NCI-CGA.
GenBank Accession No. AA507652; National Cancer Institute, Cancer Genome Anatomy Project, Tumor Gene Index; Unpublished (1997); NCI-CGA.
GenBank Accession No. AA507633; National Cancer Institute, Cancer Genome Anatomy Project, Tumor Gene Index; Unpublished (1997); NCI-CGA.
GenBank Accession No. AA507510; National Cancer Institute, Cancer Genome Anatomy Project, Tumor Gene Index; Unpublished (1997); NCI-CGA.
GenBank Accession No. AA130785; Generation and analysis of 280,000 human expressed sequence tags; Genome Res. 6 (9), 807-828 (1996); Hillier, L., et al.
GenBank Accession No. AA133485; Generation and analysis of 280,000 human expressed sequence tags; Genome Res. 6 (9), 807-828 (1996); Hillier, L., et al.
GenBank Accession No. AA129739; Generation and analysis of 280,000 human expressed sequence tags; Genome Res. 6 (9), 807-828 (1996); Hillier, L., et al.
GenBank Accession No. AA084502; Generation and analysis of 280,000 human expressed sequence tags; Genome Res. 6 (9), 807-828 (1996); Hillier, L., et al.
GenBank Accession No. AA464900; WashU-Merck EST Project 1997; Unpublished 1997; Hillier,L., et al.
GenBank Accession No. AA463818; WashU-Merck EST Project 1997; Unpublished 1997; Hillier,L., et al.
GenBank Accession No. AA461062; WashU-Merck EST Project 1997; Unpublished 1997; Hillier,L., et al.
GenBank Accession No. AA461020; WashU-Merck EST Project 1997; Unpublished 1997; Hillier,L., et al.
GenBank Accession No. AA460672; WashU-Merck EST Project 1997; Unpublished 1997; Hillier,L., et al.
GenBank Accession No. AA460492; WashU-Merck EST Project 1997; Unpublished 1997; Hillier,L., et al.
GenBank Accession No. AA460475; WashU-Merck EST Project 1997; Unpublished 1997; Hillier,L., et al.
GenBank Accession No. AA460043; WashU-Merck EST Project 1997; Unpublished 1997; Hillier,L., et al.
GenBank Accession No. AA459954; WashU-Merck EST Project 1997; Unpublished 1997; Hillier,L., et al.
GenBank Accession No. AA454090; WashU-Merck EST Project 1997; Unpublished 1997; Hillier,L., et al.
GenBank Accession No. AA450348; WashU-Merck EST Project 1997; Unpublished 1997; Hillier,L., et al.
GenBank Accession No. AA448534; WashU-Merck EST Project 1997; Unpublished 1997; Hillier,L., et al.

GenBank Accession No. AA447552; WashU-Merck EST Project 1997; Unpublished 1997; Hillier,L., et al.
GenBank Accession No. AA442736; WashU-Merck EST Project 1997; Unpublished 1997; Hillier,L., et al.
GenBank Accession No. AA431678; WashU-Merck EST Project 1997; Unpublished 1997; Hillier,L., et al.
GenBank Accession No. AA195564; Generation and analysis of 280,000 human expressed sequence tags; Genome Res. 6 (9), 807-828 (1996); Hillier, L., et al.
GenBank Accession No. AA194723; Generation and analysis of 280,000 human expressed sequence tags; Genome Res. 6 (9), 807-828 (1996); Hillier, L., et al.
GenBank Accession No. AA150024; Generation and analysis of 280,000 human expressed sequence tags; Genome Res. 6 (9), 807-828 (1996); Hillier, L., et al.
GenBank Accession No. AA147382; Generation and analysis of 280,000 human expressed sequence tags; Genome Res. 6 (9), 807-828 (1996); Hillier, L., et al.
GenBank Accession No. AA412460; WashU-Merck EST Project 1997; Unpublished 1997; Hillier,L., et al.
GenBank Accession No. AA412459; WashU-Merck EST Project 1997; Unpublished 1997; Hillier,L., et al.
GenBank Accession No. AA410464; WashU-Merck EST Project 1997; Unpublished 1997; Hillier,L., et al.
GenBank Accession No. AA410463; WashU-Merck EST Project 1997; Unpublished 1997; Hillier,L., et al.
GenBank Accession No. AA405173; WashU-Merck EST Project 1997; Unpublished 1997; Hillier,L., et al.
GenBank Accession No. AA152264; Generation and analysis of 280,000 human expressed sequence tags; Genome Res. 6 (9), 807-828 (1996); Hillier, L., et al.
GenBank Accession No. AA135514; Generation and analysis of 280,000 human expressed sequence tags; Genome Res. 6 (9), 807-828 (1996); Hillier, L., et al.
GenBank Accession No. AA130372; Generation and analysis of 280,000 human expressed sequence tags; Genome Res. 6 (9), 807-828 (1996); Hillier, L., et al.
GenBank Accession No. AA129970; Generation and analysis of 280,000 human expressed sequence tags; Genome Res. 6 (9), 807-828 (1996); Hillier, L., et al.
GenBank Accession No. AA125837; Generation and analysis of 280,000 human expressed sequence tags; Genome Res. 6 (9), 807-828 (1996); Hillier, L., et al.
GenBank Accession No. AA125836; Generation and analysis of 280,000 human expressed sequence tags; Genome Res. 6 (9), 807-828 (1996); Hillier, L., et al.
GenBank Accession No. AA115606; Generation and analysis of 280,000 human expressed sequence tags; Genome Res. 6 (9), 807-828 (1996); Hillier, L., et al.
GenBank Accession No. AA115123; Generation and analysis of 280,000 human expressed sequence tags; Genome Res. 6 (9), 807-828 (1996); Hillier, L., et al.
GenBank Accession No. AA058703; Generation and analysis of 280,000 human expressed sequence tags; Genome Res. 6 (9), 807-828 (1996); Hillier, L., et al.
GenBank Accession No. AA046156; Generation and analysis of 280,000 human expressed sequence tags; Genome Res. 6 (9), 807-828 (1996); Hillier, L., et al.
GenBank Accession No. AA045920; Generation and analysis of 280,000 human expressed sequence tags; Genome Res. 6 (9), 807-828 (1996); Hillier, L., et al.
GenBank Accession No. AA381624; Initial assessment of human gene diversity and expression patterns based upon 83 million nucleotides of cDNA sequence; Nature 377(6547 Suppl), 3-174 (1995); Adams,M.D., et al.
GenBank Accession No. AA379842; Initial assessment of human gene diversity and expression patterns based upon 83 million nucleotides of cDNA sequence; Nature 377(6547 Suppl), 3-174 (1995); Adams,M.D., et al.
GenBank Accession No. AA379577; Initial assessment of human gene diversity and expression patterns based upon 83 million nucleotides of cDNA sequence; Nature 377(6547 Suppl), 3-174 (1995); Adams,M.D., et al.
GenBank Accession No. AA377343; Initial assessment of human gene diversity and expression patterns based upon 83 million nucleotides of cDNA sequence; Nature 377(6547 Suppl), 3-174 (1995); Adams,M.D., et al.
GenBank Accession No. AA378447; Initial assessment of human gene diversity and expression patterns based upon 83 million nucleotides of cDNA sequence; Nature 377(6547 Suppl), 3-174 (1995); Adams,M.D., et al.
GenBank Accession No. AA377020; Initial assessment of human gene diversity and expression patterns based upon 83 million nucleotides of cDNA sequence; Nature 377(6547 Suppl), 3-174 (1995); Adams,M.D., et al.
GenBank Accession No. AA375392; Initial assessment of human gene diversity and expression patterns based upon 83 million nucleotides of cDNA sequence; Nature 377(6547 Suppl), 3-174 (1995); Adams,M.D., et al.
GenBank Accession No. AA374880; Initial assessment of human gene diversity and expression patterns based upon 83 million nucleotides of cDNA sequence; Nature 377(6547 Suppl), 3-174 (1995); Adams,M.D., et al.
GenBank Accession No. AA374782; Initial assessment of human gene diversity and expression patterns based upon 83 million nucleotides of cDNA sequence; Nature 377(6547 Suppl), 3-174 (1995); Adams,M.D., et al.
GenBank Accession No. AA373739; Initial assessment of human gene diversity and expression patterns based upon 83 million nucleotides of cDNA sequence; Nature 377(6547 Suppl), 3-174 (1995); Adams,M.D., et al.
GenBank Accession No. AA373146; Initial assessment of human gene diversity and expression patterns based upon 83 million nucleotides of cDNA sequence; Nature 377(6547 Suppl), 3-174 (1995); Adams,M.D., et al.
GenBank Accession No. AA372212; Initial assessment of human gene diversity and expression patterns based upon 83 million nucleotides of cDNA sequence; Nature 377(6547 Suppl), 3-174 (1995); Adams,M.D., et al.
GenBank Accession No. AA371381; Initial assessment of human gene diversity and expression patterns based upon 83 million nucleotides of cDNA sequence; Nature 377(6547 Suppl), 3-174 (1995); Adams,M.D., et al.
GenBank Accession No. AA371241; Initial assessment of human gene diversity and expression patterns based upon 83 million nucleotides of cDNA sequence; Nature 377(6547 Suppl), 3-174 (1995); Adams,M.D., et al.
GenBank Accession No. AA371211; Initial assessment of human gene diversity and expression patterns based upon 83 million nucleotides of cDNA sequence; Nature 377(6547 Suppl), 3-174 (1995); Adams,M.D., et al.
GenBank Accession No. AA371158; Initial assessment of human gene diversity and expression patterns based upon 83 million nucleotides of cDNA sequence; Nature 377(6547 Suppl), 3-174 (1995); Adams,M.D., et al.
GenBank Accession No. AA370902; Initial assessment of human gene diversity and expression patterns based upon 83 million nucleotides of cDNA sequence; Nature 377(6547 Suppl), 3-174 (1995); Adams,M.D., et al.
GenBank Accession No. AA370878; Initial assessment of human gene diversity and expression patterns based upon 83 million nucleotides of cDNA sequence; Nature 377(6547 Suppl), 3-174 (1995); Adams,M.D., et al.
GenBank Accession No. AA369995; Initial assessment of human gene diversity and expression patterns based upon 83 million nucleotides of cDNA sequence; Nature 377(6547 Suppl), 3-174 (1995); Adams,M.D., et al.
GenBank Accession No. AA369975; Initial assessment of human gene diversity and expression patterns based upon 83 million nucleotides of cDNA sequence; Nature 377(6547 Suppl), 3-174 (1995); Adams,M.D., et al.
GenBank Accession No. AA369957; Rapid cDNA sequencing (expressed sequence tags) from a directionally cloned human infant brain cDNA library; Nat. Genet. 4, 373-380 (1993); Adams,M. D., et al.

GenBank Accession No. AA367807; Initial assessment of human gene diversity and expression patterns based upon 83 million nucleotides of cDNA sequence; Nature 377(6547 Suppl), 3-174 (1995); Adams,M.D., et al.
GenBank Accession No. AA364975; Initial assessment of human gene diversity and expression patterns based upon 83 million nucleotides of cDNA sequence; Nature 377(6547 Suppl), 3-174 (1995); Adams,M.D., et al.
GenBank Accession No. AA361655; Initial assessment of human gene diversity and expression patterns based upon 83 million nucleotides of cDNA sequence; Nature 377(6547 Suppl), 3-174 (1995); Adams,M.D., et al.
GenBank Accession No. AA360690; Initial assessment of human gene diversity and expression patterns based upon 83 million nucleotides of cDNA sequence; Nature 377(6547 Suppl), 3-174 (1995); Adams,M.D., et al.
GenBank Accession No. AA360619; Initial assessment of human gene diversity and expression patterns based upon 83 million nucleotides of cDNA sequence; Nature 377(6547 Suppl), 3-174 (1995); Adams,M.D., et al.
GenBank Accession No. AA360537; Initial assessment of human gene diversity and expression patterns based upon 83 million nucleotides of cDNA sequence; Nature 377(6547 Suppl), 3-174 (1995); Adams,M.D., et al.
GenBank Accession No. AA358983; Initial assessment of human gene diversity and expression patterns based upon 83 million nucleotides of cDNA sequence; Nature 377(6547 Suppl), 3-174 (1995); Adams,M.D., et al.
GenBank Accession No. AA357362; Initial assessment of human gene diversity and expression patterns based upon 83 million nucleotides of cDNA sequence; Nature 377(6547 Suppl), 3-174 (1995); Adams,M.D., et al.
GenBank Accession No. AA355454; Initial assessment of human gene diversity and expression patterns based upon 83 million nucleotides of cDNA sequence; Nature 377(6547 Suppl), 3-174 (1995); Adams,M.D., et al.
GenBank Accession No. AA347726; Initial assessment of human gene diversity and expression patterns based upon 83 million nucleotides of cDNA sequence; Nature 377(6547 Suppl), 3-174 (1995); Adams,M.D., et al.
GenBank Accession No. AA347621; Initial assessment of human gene diversity and expression patterns based upon 83 million nucleotides of cDNA sequence; Nature 377(6547 Suppl), 3-174 (1995); Adams,M.D., et al.
GenBank Accession No. AA346951; Initial assessment of human gene diversity and expression patterns based upon 83 million nucleotides of cDNA sequence; Nature 377(6547 Suppl), 3-174 (1995); Adams,M.D., et al.
GenBank Accession No. AA341153; Rapid cDNA sequencing (expressed sequence tags) from a directionally cloned human infant cDNA library; Nat. Genet. 4, 373-380 (1993); Adams,M. D., et al.
GenBank Accession No. AA339588; Initial assessment of human gene diversity and expression patterns based upon 83 million nucleotides of cDNA sequence; Nature 377(6547 Suppl), 3-174 (1995); Adams,M.D., et al.
GenBank Accession No. AA338092; Initial assessment of human gene diversity and expression patterns based upon 83 million nucleotides of cDNA sequence; Nature 377(6547 Suppl), 3-174 (1995); Adams,M.D., et al.
GenBank Accession No. AA332153; Initial assessment of human gene diversity and expression patterns based upon 83 million nucleotides of cDNA sequence; Nature 377(6547 Suppl), 3-174 (1995); Adams,M.D., et al.
GenBank Accession No. AA327758; Initial assessment of human gene diversity and expression patterns based upon 83 million nucleotides of cDNA sequence; Nature 377(6547 Suppl), 3-174 (1995); Adams,M.D., et al.
GenBank Accession No. AA317353; Initial assessment of human gene diversity and expression patterns based upon 83 million nucleotides of cDNA sequence; Nature 377(6547 Suppl), 3-174 (1995); Adams,M.D., et al.
GenBank Accession No. AA317051; Initial assessment of human gene diversity and expression patterns based upon 83 million nucleotides of cDNA sequence; Nature 377(6547 Suppl), 3-174 (1995); Adams,M.D., et al.
GenBank Accession No. AA316821; Initial assessment of human gene diversity and expression patterns based upon 83 million nucleotides of cDNA sequence; Nature 377(6547 Suppl), 3-174 (1995); Adams,M.D., et al.
GenBank Accession No. AA316565; Initial assessment of human gene diversity and expression patterns based upon 83 million nucleotides of cDNA sequence; Nature 377(6547 Suppl), 3-174 (1995); Adams,M.D., et al.
GenBank Accession No. AA313455; Initial assessment of human gene diversity and expression patterns based upon 83 million nucleotides of cDNA sequence; Nature 377(6547 Suppl), 3-174 (1995); Adams,M.D., et al.
GenBank Accession No. AA311834; Initial assessment of human gene diversity and expression patterns based upon 83 million nucleotides of cDNA sequence; Nature 377(6547 Suppl), 3-174 (1995); Adams,M.D., et al.
GenBank Accession No. AA308561; Initial assessment of human gene diversity and expression patterns based upon 83 million nucleotides of cDNA sequence; Nature 377(6547 Suppl), 3-174 (1995); Adams,M.D., et al.
GenBank Accession No. AA305190; Initial assessment of human gene diversity and expression patterns based upon 83 million nucleotides of cDNA sequence; Nature 377(6547 Suppl), 3-174 (1995); Adams,M.D., et al.
GenBank Accession No. AA305061; Initial assessment of human gene diversity and expression patterns based upon 83 million nucleotides of cDNA sequence; Nature 377(6547 Suppl), 3-174 (1995); Adams,M.D., et al.
GenBank Accession No. AA304722; Initial assessment of human gene diversity and expression patterns based upon 83 million nucleotides of cDNA sequence; Nature 377(6547 Suppl), 3-174 (1995); Adams,M.D., et al.
GenBank Accession No. AA304273; Initial assessment of human gene diversity and expression patterns based upon 83 million nucleotides of cDNA sequence; Nature 377(6547 Suppl), 3-174 (1995); Adams,M.D., et al.
GenBank Accession No. AA303809; Initial assessment of human gene diversity and expression patterns based upon 83 million nucleotides of cDNA sequence; Nature 377(6547 Suppl), 3-174 (1995); Adams,M.D., et al.
GenBank Accession No. AA303436; Initial assessment of human gene diversity and expression patterns based upon 83 million nucleotides of cDNA sequence; Nature 377(6547 Suppl), 3-174 (1995); Adams,M.D., et al.
GenBank Accession No. AA303078; Rapid cDNA sequencing (expressed sequence tags) from a directionally cloned human infant brain cDNA library; Nat. Genet. 4, 373-380 (1993); Adams, M. D., et al.
GenBank Accession No. AA303077; Rapid cDNA sequencing (expressed sequence tags) from a directionally cloned human infant brain cDNA library; Nat. Genet. 4, 373-380 (1993); Adams, M. D., et al.
GenBank Accession No. AA300220; Initial assessment of human gene diversity and expression patterns based upon 83 million nucleotides of cDNA sequence; Nature 377(6547 Suppl), 3-174 (1995); Adams,M.D., et al.
GenBank Accession No. AA298881; Initial assessment of human gene diversity and expression patterns based upon 83 million nucleotides of cDNA sequence; Nature 377(6547 Suppl), 3-174 (1995); Adams,M.D., et al.
GenBank Accession No. AA298885; Initial assessment of human gene diversity and expression patterns based upon 83 million nucleotides of cDNA sequence; Nature 377(6547 Suppl), 3-174 (1995); Adams,M.D., et al.
GenBank Accession No. AA298657; Initial assessment of human gene diversity and expression patterns based upon 83 million nucleotides of cDNA sequence; Nature 377(6547 Suppl), 3-174 (1995); Adams,M.D., et al.

GenBank Accession No. AA298645; Initial assessment of human gene diversity and expression patterns based upon 83 million nucleotides of cDNA sequence; Nature 377(6547 Suppl), 3-174 (1995); Adams,M.D., et al.
GenBank Accession No. AA298291; Initial assessment of human gene diversity and expression patterns based upon 83 million nucleotides of cDNA sequence; Nature 377(6547 Suppl), 3-174 (1995); Adams,M.D., et al.
GenBank Accession No. AA298082; Initial assessment of human gene diversity and expression patterns based upon 83 million nucleotides of cDNA sequence; Nature 377(6547 Suppl), 3-174 (1995); Adams,M.D., et al.
GenBank Accession No. AA297908; Initial assessment of human gene diversity and expression patterns based upon 83 million nucleotides of cDNA sequence; Nature 377(6547 Suppl), 3-174 (1995); Adams,M.D., et al.
GenBank Accession No. AA298066; Initial assessment of human gene diversity and expression patterns based upon 83 million nucleotides of cDNA sequence; Nature 377(6547 Suppl), 3-174 (1995); Adams,M.D., et al.
GenBank Accession No. AA297811; Initial assessment of human gene diversity and expression patterns based upon 83 million nucleotides of cDNA sequence; Nature 377(6547 Suppl), 3-174 (1995); Adams,M.D., et al.
GenBank Accession No. AA297608; Initial assessment of human gene diversity and expression patterns based upon 83 million nucleotides of cDNA sequence; Nature 377(6547 Suppl), 3-174 (1995); Adams,M.D., et al.
GenBank Accession No. AA297030; Initial assessment of human gene diversity and expression patterns based upon 83 million nucleotides of cDNA sequence; Nature 377(6547 Suppl), 3-174 (1995); Adams,M.D., et al.
GenBank Accession No. AA297024; Initial assessment of human gene diversity and expression patterns based upon 83 million nucleotides of cDNA sequence; Nature 377(6547 Suppl), 3-174 (1995); Adams,M.D., et al.
GenBank Accession No. AA297316; Initial assessment of human gene diversity and expression patterns based upon 83 million nucleotides of cDNA sequence; Nature 377(6547 Suppl), 3-174 (1995); Adams,M.D., et al.
GenBank Accession No. AA297256; Initial assessment of human gene diversity and expression patterns based upon 83 million nucleotides of cDNA sequence; Nature 377(6547 Suppl), 3-174 (1995); Adams,M.D., et al.
GenBank Accession No. AA296793; Initial assessment of human gene diversity and expression patterns based upon 83 million nucleotides of cDNA sequence; Nature 377(6547 Suppl), 3-174 (1995); Adams,M.D., et al.
GenBank Accession No. AA296225; Initial assessment of human gene diversity and expression patterns based upon 83 million nucleotides of cDNA sequence; Nature 377(6547 Suppl), 3-174 (1995); Adams,M.D., et al.
GenBank Accession No. AA295182; Initial assessment of human gene diversity and expression patterns based upon 83 million nucleotides of cDNA sequence; Nature 377(6547 Suppl), 3-174 (1995); Adams,M.D., et al.
GenBank Accession No. AA294850; Initial assessment of human gene diversity and expression patterns based upon 83 million nucleotides of cDNA sequence; Nature 377(6547 Suppl), 3-174 (1995); Adams,M.D., et al.
GenBank Accession No. AA234584; WashU-Merck EST Project 1997; Unpublished 1997; Hillier,L., et al.
GenBank Accession No. AA236476; WashU-Merck EST Project 1997; Unpublished 1997; Hillier,L., et al.
GenBank Accession No. AA220956; Generation and analysis of 280,000 human expressed sequence tags; Genome Res. 6 (9), 807-828 (1996); Hillier, L., et al.
GenBank Accession No. AA219114; Generation and analysis of 280,000 human expressed sequence tags; Genome Res. 6 (9), 807-828 (1996); Hillier, L., et al.
GenBank Accession No. AA063043; Generation and analysis of 280,000 human expressed sequence tags; Genome Res. 6 (9), 807-828 (1996); Hillier, L., et al.
GenBank Accession No. AA056130; Generation and analysis of 280,000 human expressed sequence tags; Genome Res. 6 (9), 807-828 (1996); Hillier, L., et al.
GenBank Accession No. AA209534; Generation and analysis of 280,000 human expressed sequence tags; Genome Res. 6 (9), 807-828 (1996); Hillier, L., et al.
GenBank Accession No. AA190958; Generation and analysis of 280,000 human expressed sequence tags; Genome Res. 6 (9), 807-828 (1996); Hillier, L., et al.
GenBank Accession No. AA190865; Generation and analysis of 280,000 human expressed sequence tags; Genome Res. 6 (9), 807-828 (1996); Hillier, L., et al.
GenBank Accession No. AA188576; Generation and analysis of 280,000 human expressed sequence tags; Genome Res. 6 (9), 807-828 (1996); Hillier, L., et al.
GenBank Accession No. AA188533; Generation and analysis of 280,000 human expressed sequence tags; Genome Res. 6 (9), 807-828 (1996); Hillier, L., et al.
GenBank Accession No. U51145; High-density filter differential display; Unpublished (1996); Lin,B. and Frischauf,A.M.
GenBank Accession No. AA164906; Generation and analysis of 280,000 human expressed sequence tags; Genome Res. 6 (9), 807-828 (1996); Hillier, L., et al.
GenBank Accession No. AA158516; Generation and analysis of 280,000 human expressed sequence tags; Genome Res. 6 (9), 807-828 (1996); Hillier, L., et al.
GenBank Accession No. AA158327; Generation and analysis of 280,000 human expressed sequence tags; Genome Res. 6 (9), 807-828 (1996); Hillier, L., et al.
GenBank Accession No. AA158036; Generation and analysis of 280,000 human expressed sequence tags; Genome Res. 6 (9), 807-828 (1996); Hillier, L., et al.
GenBank Accession No. AA149664; Generation and analysis of 280,000 human expressed sequence tags; Genome Res. 6 (9), 807-828 (1996); Hillier, L., et al.
GenBank Accession No. AA151536; WashU-Merck EST Project 1995; Unpublished 1995; Hillier, L., et al.
GenBank Accession No. AA149251; WashU-Merck EST Project 1995; Unpublished 1995; Hillier, L., et al.
GenBank Accession No. AA148742; Generation and analysis of 280,000 human expressed sequence tags; Genome Res. 6 (9), 807-828 (1996); Hillier, L., et al.
GenBank Accession No. AA142830; WashU-Merck EST Project 1995; Unpublished 1995; Hillier, L., et al.
GenBank Accession No. AA135576; WashU-Merck EST Project 1995; Unpublished 1995; Hillier, L., et al.
GenBank Accession No. AA134741; WashU-Merck EST Project 1995; Unpublished 1995; Hillier, L., et al.
GenBank Accession No. AA016198; WashU-Merck EST Project 1995; Unpublished 1995; Hillier, L., et al.
GenBank Accession No. W96255; WashU-Merck EST Project 1995; Unpublished 1996; Hillier, L., et al.
GenBank Accession No. AA133340; Generation and analysis of 280,000 human expressed sequence tags; Genome Res. 6 (9), 807-828 (1996); Hillier, L., et al.
GenBank Accession No. AA129913; Generation and analysis of 280,000 human expressed sequence tags; Genome Res. 6 (9), 807-828 (1996); Hillier, L., et al.
GenBank Accession No. W31233; WashU-Merck EST Project 1995; Unpublished 1995; Hillier, L., et al.
GenBank Accession No. AA086038; Generation and analysis of 280,000 human expressed sequence tags; Genome Res. 6 (9), 807-828 (1996); Hillier, L., et al.
GenBank Accession No. AA082042; Generation and analysis of 280,000 human expressed sequence tags; Genome Res. 6 (9), 807-828 (1996); Hillier, L., et al.
GenBank Accession No. W63796; WashU-Merck EST Project 1995; Unpublished 1995; Hillier, L., et al.
GenBank Accession No. AA223617; WashU-Merck EST Project 1995; Unpublished 1997; Hillier, L., et al.
GenBank Accession No. AA218549; WashU-NCI Human EST Project 1997; Unpublished 1997; Hillier, L., et al.

GenBank Accession No. AA218548; WashU-NCI Human EST Project 1997; Unpublished 1997; Hillier, L., et al.
GenBank Accession No. AA216757; WashU-NCI Human EST Project 1997; Unpublished 1997; Hillier, L., et al.
GenBank Accession No. AA216755; WashU-NCI Human EST Project 1997; Unpublished 1997; Hillier, L., et al.
GenBank Accession No. AA161431; WashU-NCI Human EST Project 1997; Unpublished 1997; Hillier, L., et al.
GenBank Accession No. AA227333; WashU-NCI Human EST Project 1997; Unpublished 1997; Hillier, L., et al.
GenBank Accession No. AA227381; WashU-NCI Human EST Project 1997; Unpublished 1997; Hillier, L., et al.
GenBank Accession No. AA227015; WashU-NCI Human EST Project 1997; Unpublished 1997; Hillier, L., et al.
GenBank Accession No. AA226931; WashU-NCI Human EST Project 1997; Unpublished 1997; Hillier, L., et al.
GenBank Accession No. AA224580; WashU-NCI Human EST Project 1997; Unpublished 1997; Hillier, L., et al.
GenBank Accession No. AA161219; WashU-NCI Human EST Project 1997; Unpublished 1997; Hillier, L., et al.
GenBank Accession No. AA159121; WashU-NCI Human EST Project 1997; Unpublished 1997; Hillier, L., et al.
GenBank Accession No. AA489319; WashU-NCI Human EST Project 1997; Unpublished 1997; Hillier, L., et al.
GenBank Accession No. AA489463; WashU-NCI Human EST Project 1997; Unpublished 1997; Hillier, L., et al
GenBank Accession No. AA100216; Generation and analysis of 280,000 human expressed sequence tags; Genome Res. 6 (9), 807-828 (1996); Hillier, L., et al.
GenBank Accession No. AA079751; Generation and analysis of 280,000 human expressed sequence tags; Genome Res. 6 (9), 807-828 (1996); Hillier, L., et al.
GenBank Accession No. AA075724; Generation and analysis of 280,000 human expressed sequence tags; Genome Res. 6 (9), 807-828 (1996); Hillier, L., et al.
GenBank Accession No. AA064595; Generation and analysis of 280,000 human expressed sequence tags; Genome Res. 6 (9), 807-828 (1996); Hillier, L., et al.
GenBank Accession No. AA065044; Generation and analysis of 280,000 human expressed sequence tags; Genome Res. 6 (9), 807-828 (1996); Hillier, L., et al.
GenBank Accession No. AA477270; WashU-NCI Human EST Project 1997; Unpublished 1997; Hillier, L., et al
GenBank Accession No. AA405215; WashU-NCI Human EST Project 1997; Unpublished 1997; Hillier, L., et al
GenBank Accession No. AA402665; WashU-NCI Human EST Project 1997; Unpublished 1997; Hillier, L., et al
GenBank Accession No. AA402235; WashU-NCI Human EST Project 1997; Unpublished 1997; Hillier, L., et al
GenBank Accession No. AA159086; WashU-NCI Human EST Project 1997; Unpublished 1997; Hillier, L., et al
GenBank Accession No. AA146624; WashU-NCI Human EST Project 1997; Unpublished 1997; Hillier, L., et al
GenBank Accession No. AA143739; WashU-NCI Human EST Project 1997; Unpublished 1997; Hillier, L., et al
GenBank Accession No. AA143726; WashU-NCI Human EST Project 1997; Unpublished 1997; Hillier, L., et al
GenBank Accession No. AA143555; WashU-NCI Human EST Project 1997; Unpublished 1997; Hillier, L., et al
GenBank Accession No. AA428515; WashU-NCI Human EST Project 1997; Unpublished 1997; Hillier, L., et al
GenBank Accession No. AA429428; WashU-NCI Human EST Project 1997; Unpublished 1997; Hillier, L., et al
GenBank Accession No. AA430318; WashU-NCI Human EST Project 1997; Unpublished 1997; Hillier, L., et al
GenBank Accession No. AA425157; WashU-NCI Human EST Project 1997; Unpublished 1997; Hillier, L., et al
GenBank Accession No. AA419490; WashU-NCI Human EST Project 1997; Unpublished 1997; Hillier, L., et al
GenBank Accession No. AA587386; National Cancer Institute, Cancer Genome Anatomy Project, Tumor Gene Index; Unpublished (1997); NCI-CGA.
GenBank Accession No. AA582961; National Cancer Institute, Cancer Genome Anatomy Project, Tumor Gene Index; Unpublished (1997); NCI-CGA.
GenBank Accession No. AA579316; National Cancer Institute, Cancer Genome Anatomy Project, Tumor Gene Index; Unpublished (1997); NCI-CGA.
GenBank Accession No. AA578507; National Cancer Institute, Cancer Genome Anatomy Project, Tumor Gene Index; Unpublished (1997); NCI-CGA.
GenBank Accession No. AA574391; National Cancer Institute, Cancer Genome Anatomy Project, Tumor Gene Index; Unpublished (1997); NCI-CGA.
GenBank Accession No. AA576497; National Cancer Institute, Cancer Genome Anatomy Project, Tumor Gene Index; Unpublished (1997); NCI-CGA.
GenBank Accession No. AA558349; National Cancer Institute, Cancer Genome Anatomy Project, Tumor Gene Index; Unpublished (1997); NCI-CGA.
GenBank Accession No. AA565889; National Cancer Institute, Cancer Genome Anatomy Project, Tumor Gene Index; Unpublished (1997); NCI-CGA.
GenBank Accession No. AA564499; National Cancer Institute, Cancer Genome Anatomy Project, Tumor Gene Index; Unpublished (1997); NCI-CGA.
GenBank Accession No. AA577007; National Cancer Institute, Cancer Genome Anatomy Project, Tumor Gene Index; Unpublished (1997); NCI-CGA.
GenBank Accession No. AA572905; National Cancer Institute, Cancer Genome Anatomy Project, Tumor Gene Index; Unpublished (1997); NCI-CGA.
GenBank Accession No. AA534799; National Cancer Institute, Cancer Genome Anatomy Project, Tumor Gene Index; Unpublished (1997); NCI-CGA.
GenBank Accession No. AA534542; National Cancer Institute, Cancer Genome Anatomy Project, Tumor Gene Index; Unpublished (1997); NCI-CGA.
GenBank Accession No. AA533505; National Cancer Institute, Cancer Genome Anatomy Project, Tumor Gene Index; Unpublished (1997); NCI-CGA.
GenBank Accession No. AA228426; National Cancer Institute, Cancer Genome Anatomy Project, Tumor Gene Index; Unpublished (1997); NCI-CGA.
GenBank Accession No. AA228353; National Cancer Institute, Cancer Genome Anatomy Project, Tumor Gene Index; Unpublished (1997); NCI-CGA.
GenBank Accession No. AA516514; National Cancer Institute, Cancer Genome Anatomy Project, Tumor Gene Index; Unpublished (1997); NCI-CGA.
GenBank Accession No. AA515498; National Cancer Institute, Cancer Genome Anatomy Project, Tumor Gene Index; Unpublished (1997); NCI-CGA.
GenBank Accession No. AA503633; National Cancer Institute, Cancer Genome Anatomy Project, Tumor Gene Index; Unpublished (1997); NCI-CGA.
GenBank Accession No. AA261959; National Cancer Institute, Cancer Genome Anatomy Project, Tumor Gene Index; Unpublished (1997); NCI-CGA.
GenBank Accession No. AA554836; National Cancer Institute, Cancer Genome Anatomy Project, Tumor Gene Index; Unpublished (1997); NCI-CGA.
GenBank Accession No. AA486867; WashU-Merck EST Project 1997;Unpublished 1997; Hillier, L., et al.
GenBank Accession No. AA485845; WashU-Merck EST Project 1997;Unpublished 1997; Hillier, L., et al.
GenBank Accession No. AA485712; WashU-Merck EST Project 1997;Unpublished 1997; Hillier, L., et al.
GenBank Accession No. AA291354; Generation and analysis of 280,000 human expressed sequence tags; Genome Res. 6 (9), 807-828 (1996); Hillier, L., et al.
GenBank Accession No. AA234880; Generation and analysis of 280,000 human expressed sequence tags; Genome Res. 6 (9), 807-828 (1996); Hillier, L., et al.

GenBank Accession No. AA234715; WashU-Merck EST Project 1997;Unpublished 1997; Hillier, L., et al.
GenBank Accession No. AA236409; WashU-Merck EST Project 1997;Unpublished 1997; Hillier, L., et al.
GenBank Accession No. AA236408; WashU-Merck EST Project 1997;Unpublished 1997; Hillier, L., et al.
GenBank Accession No. AA228049; WashU-Merck EST Project 1997;Unpublished 1997; Hillier, L., et al.
GenBank Accession No. AA228011; WashU-Merck EST Project 1997;Unpublished 1997; Hillier, L., et al.
GenBank Accession No. AA527509; National Cancer Institute, Cancer Genome Anatomy Project, Tumor Gene Index; Unpublished (1997); NCI-CGA.
GenBank Accession No. AA526987; National Cancer Institute, Cancer Genome Anatomy Project, Tumor Gene Index; Unpublished (1997); NCI-CGA.
GenBank Accession No. AA458463; WashU-Merck EST Project 1997;Unpublished 1997; Hillier, L., et al.
GenBank Accession No. AA455377; WashU-Merck EST Project 1997;Unpublished 1997; Hillier, L., et al.
GenBank Accession No. AA455223; WashU-Merck EST Project 1997;Unpublished 1997; Hillier, L., et al.
GenBank Accession No. AA448940; WashU-Merck EST Project 1997;Unpublished 1997; Hillier, L., et al.
GenBank Accession No. AA442975; WashU-Merck EST Project 1997;Unpublished 1997; Hillier, L., et al.
GenBank Accession No. AA442650; WashU-Merck EST Project 1997;Unpublished 1997; Hillier, L., et al.
GenBank Accession No. AA442640; WashU-Merck EST Project 1997;Unpublished 1997; Hillier, L., et al.
GenBank Accession No. AA436795; WashU-Merck EST Project 1997;Unpublished 1997; Hillier, L., et al.
GenBank Accession No. AA410374; WashU-Merck EST Project 1997;Unpublished 1997; Hillier, L., et al.
GenBank Accession No. AA411593; WashU-Merck EST Project 1997;Unpublished 1997; Hillier, L., et al.
GenBank Accession No. AA411540; WashU-Merck EST Project 1997;Unpublished 1997; Hillier, L., et al.
GenBank Accession No. AA405235; WashU-Merck EST Project 1997;Unpublished 1997; Hillier, L., et al.
GenBank Accession No. AA402978; WashU-Merck EST Project 1997;Unpublished 1997; Hillier, L., et al.
GenBank Accession No. AA402380; WashU-Merck EST Project 1997;Unpublished 1997; Hillier, L., et al.
GenBank Accession No. AA402234; WashU-Merck EST Project 1997;Unpublished 1997; Hillier, L., et al.
GenBank Accession No. AA400276; WashU-Merck EST Project 1997;Unpublished 1997; Hillier, L., et al.
GenBank Accession No. AA401316; WashU-Merck EST Project 1997;Unpublished 1997; Hillier, L., et al.
GenBank Accession No. AA035266; Generation and analysis of 280,000 human expressed sequence tags; Genome Res. 6 (9), 807-828 (1996); Hillier, L., et al.
GenBank Accession No. AA031678; Generation and analysis of 280,000 human expressed sequence tags; Genome Res. 6 (9), 807-828 (1996); Hillier, L., et al.
GenBank Accession No. AA031677; Generation and analysis of 280,000 human expressed sequence tags; Genome Res. 6 (9), 807-828 (1996); Hillier, L., et al.
GenBank Accession No. AA026175; Generation and analysis of 280,000 human expressed sequence tags; Genome Res. 6 (9), 807-828 (1996); Hillier, L., et al.
GenBank Accession No. AA010229; Generation and analysis of 280,000 human expressed sequence tags; Genome Res. 6 (9), 807-828 (1996); Hillier, L., et al.
GenBank Accession No. AA385221; Initial assessment of human gene diversity and expression patterns based upon 83 million nucleotides of cDNA sequence; Nature 377(6547 Suppl), 3-174 (1995); Adams,M.D., et al.
GenBank Accession No. AA375326; Initial assessment of human gene diversity and expression patterns based upon 83 million nucleotides of cDNA sequence; Nature 377(6547 Suppl), 3-174 (1995); Adams,M.D., et al.
GenBank Accession No. AA374874; Initial assessment of human gene diversity and expression patterns based upon 83 million nucleotides of cDNA sequence; Nature 377(6547 Suppl), 3-174 (1995); Adams,M.D., et al.
GenBank Accession No. AA374263; Initial assessment of human gene diversity and expression patterns based upon 83 million nucleotides of cDNA sequence; Nature 377(6547 Suppl), 3-174 (1995); Adams,M.D., et al.
GenBank Accession No. AA359764; Initial assessment of human gene diversity and expression patterns based upon 83 million nucleotides of cDNA sequence; Nature 377(6547 Suppl), 3-174 (1995); Adams,M.D., et al.
GenBank Accession No. AA349570; 3,400 expressed sequence tags identify diversity of transcripts from human brain; Nat. Genet. 4, 256-267 (1993), Adams,M.D., et al.
GenBank Accession No. AA349569; 3,400 expressed sequence tags identify diversity of transcripts from human brain; Nat. Genet. 4, 256-267 (1993), Adams,M.D., et al.
GenBank Accession No. AA347823; Initial assessment of human gene diversity and expression patterns based upon 83 million nucleotides of cDNA sequence; Nature 377(6547 Suppl), 3-174 (1995); Adams,M.D., et al.
GenBank Accession No. AA344459; Initial assessment of human gene diversity and expression patterns based upon 83 million nucleotides of cDNA sequence; Nature 377(6547 Suppl), 3-174 (1995); Adams,M.D., et al.
GenBank Accession No. AA343828; Initial assessment of human gene diversity and expression patterns based upon 83 million nucleotides of cDNA sequence; Nature 377(6547 Suppl), 3-174 (1995); Adams,M.D., et al.
GenBank Accession No. AA332443; Initial assessment of human gene diversity and expression patterns based upon 83 million nucleotides of cDNA sequence; Nature 377(6547 Suppl), 3-174 (1995); Adams,M.D., et al.
GenBank Accession No. AA331589; Initial assessment of human gene diversity and expression patterns based upon 83 million nucleotides of cDNA sequence; Nature 377(6547 Suppl), 3-174 (1995); Adams,M.D., et al.
GenBank Accession No. AA321034; Initial assessment of human gene diversity and expression patterns based upon 83 million nucleotides of cDNA sequence; Nature 377(6547 Suppl), 3-174 (1995); Adams,M.D., et al.
GenBank Accession No. AA319878; Initial assessment of human gene diversity and expression patterns based upon 83 million nucleotides of cDNA sequence; Nature 377(6547 Suppl), 3-174 (1995); Adams,M.D., et al.
GenBank Accession No. AA317601; Initial assessment of human gene diversity and expression patterns based upon 83 million nucleotides of cDNA sequence; Nature 377(6547 Suppl), 3-174 (1995); Adams,M.D., et al.
GenBank Accession No. AA300847; Initial assessment of human gene diversity and expression patterns based upon 83 million nucleotides of cDNA sequence; Nature 377(6547 Suppl), 3-174 (1995); Adams,M.D., et al.
GenBank Accession No. AA297594; Initial assessment of human gene diversity and expression patterns based upon 83 million nucleotides of cDNA sequence; Nature 377(6547 Suppl), 3-174 (1995); Adams,M.D., et al.
GenBank Accession No. AA297535; Initial assessment of human gene diversity and expression patterns based upon 83 million nucleotides of cDNA sequence; Nature 377(6547 Suppl), 3-174 (1995); Adams,M.D., et al.
GenBank Accession No. AA297007; Initial assessment of human gene diversity and expression patterns based upon 83 million nucleotides of cDNA sequence; Nature 377(6547 Suppl), 3-174 (1995); Adams,M.D., et al.
GenBank Accession No. AA296694; Initial assessment of human gene diversity and expression patterns based upon 83 million nucleotides of cDNA sequence; Nature 377(6547 Suppl), 3-174 (1995); Adams,M.D., et al.

GenBank Accession No. AA294974; Initial assessment of human gene diversity and expression patterns based upon 83 million nucleotides of cDNA sequence; Nature 377(6547 Suppl), 3-174 (1995); Adams,M.D., et al.
GenBank Accession No. AA294885; Initial assessment of human gene diversity and expression patterns based upon 83 million nucleotides of cDNA sequence; Nature 377(6547 Suppl), 3-174 (1995); Adams,M.D., et al.
GenBank Accession No. AA294870; Initial assessment of human gene diversity and expression patterns based upon 83 million nucleotides of cDNA sequence; Nature 377(6547 Suppl), 3-174 (1995); Adams,M.D., et al.
GenBank Accession No. AA046902; Generation and analysis of 280,000 human expressed sequence tags; Genome Res. 6 (9), 807-828 (1996); Hillier, L., et al.
GenBank Accession No. AA021288; Generation and analysis of 280,000 human expressed sequence tags; Genome Res. 6 (9), 807-828 (1996); Hillier, L., et al.
GenBank Accession No. AA019581; Generation and analysis of 280,000 human expressed sequence tags; Genome Res. 6 (9), 807-828 (1996); Hillier, L., et al.
GenBank Accession No. AA019189; Generation and analysis of 280,000 human expressed sequence tags; Genome Res. 6 (9), 807-828 (1996); Hillier, L., et al.
GenBank Accession No. AA018201; Generation and analysis of 280,000 human expressed sequence tags; Genome Res. 6 (9), 807-828 (1996); Hillier, L., et al.
GenBank Accession No. N62098; Generation and analysis of 280,000 human expressed sequence tags; Genome Res. 6 (9), 807-828 (1996); Hillier, L., et al.
GenBank Accession No. N57774; Generation and analysis of 280,000 human expressed sequence tags; Genome Res. 6 (9), 807-828 (1996); Hillier, L., et al.
GenBank Accession No. AA205675; Generation and analysis of 280,000 human expressed sequence tags; Genome Res. 6 (9), 807-828 (1996); Hillier, L., et al.
GenBank Accession No. AA205710; Generation and analysis of 280,000 human expressed sequence tags; Genome Res. 6 (9), 807-828 (1996); Hillier, L., et al.
GenBank Accession No. AA155597; Generation and analysis of 280,000 human expressed sequence tags; Genome Res. 6 (9), 807-828 (1996); Hillier, L., et al.
GenBank Accession No. AA146682; Generation and analysis of 280,000 human expressed sequence tags; Genome Res. 6 (9), 807-828 (1996); Hillier, L., et al.
GenBank Accession No. AA146681; Generation and analysis of 280,000 human expressed sequence tags; Genome Res. 6 (9), 807-828 (1996); Hillier, L., et al.
GenBank Accession No. AA101474; Generation and analysis of 280,000 human expressed sequence tags; Genome Res. 6 (9), 807-828 (1996); Hillier, L., et al.
GenBank Accession No. AA101473; Generation and analysis of 280,000 human expressed sequence tags; Genome Res. 6 (9), 807-828 (1996); Hillier, L., et al.
GenBank Accession No. AA056635; Generation and analysis of 280,000 human expressed sequence tags; Genome Res. 6 (9), 807-828 (1996); Hillier, L., et al.
GenBank Accession No. AA129456; Generation and analysis of 280,000 human expressed sequence tags; Genome Res. 6 (9), 807-828 (1996); Hillier, L., et al.
GenBank Accession No. AA121609; Generation and analysis of 280,000 human expressed sequence tags; Genome Res. 6 (9), 807-828 (1996); Hillier, L., et al.
GenBank Accession No. AA101475; Generation and analysis of 280,000 human expressed sequence tags; Genome Res. 6 (9), 807-828 (1996); Hillier, L., et al.
GenBank Accession No. C05685; Human pancreatic islet ESTs; Unpublished (1995); Takeda,J.
GenBank Accession No. W44900; The WashU-Merck EST Project; Unpublished 1995; Hillier, L., Wilson, R., et al.
GenBank Accession No. W39595; The WashU-Merck EST Project; Unpublished 1995; Hillier, L., Wilson, R., et al.
GenBank Accession No. AA053511; Generation and analysis of 280,000 human expressed sequence tags; Genome Res. 6 (9), 807-828 (1996); Hillier, L., et al.
GenBank Accession No. AA053124; Generation and analysis of 280,000 human expressed sequence tags; Genome Res. 6 (9), 807-828 (1996); Hillier, L., et al.
GenBank Accession No. AA044127; The WashU-Merck EST Project; Unpublished 1995; Hillier, L., Wilson, R., et al.
GenBank Accession No. AA040335; The WashU-Merck EST Project; Unpublished 1995; Hillier, L., Wilson, R., et al.
GenBank Accession No. AA019588; The WashU-Merck EST Project; Unpublished 1995; Hillier, L., Wilson, R., et al.
GenBank Accession No. AA018379; The WashU-Merck EST Project; Unpublished 1995; Hillier, L., Wilson, R., et al.
GenBank Accession No. R58843; Gene-based Sequence Tagged Sites (STSs) as the basis for a human gene map; Nat. Genet. 10, 415-423 (1995); Berry,R., et al.
GenBank Accession No. R58836; Gene-based Sequence Tagged Sites (STSs) as the basis for a human gene map; Nat. Genet. 10, 415-423 (1995); Berry,R., et al.
GenBank Accession No. W60092; Generation and analysis of 280,000 human expressed sequence tags; Genome Res. 6 (9), 807-828 (1996); Hillier, L., et al.
GenBank Accession No. W52884; Generation and analysis of 280,000 human expressed sequence tags; Genome Res. 6 (9), 807-828 (1996); Hillier, L., et al.
GenBank Accession No. W17355; The WashU-Merck EST Project; Unpublished 1995; Hillier, L., Wilson, R., et al.
GenBank Accession No. W01171; The WashU-Merck EST Project; Unpublished 1995; Hillier, L., Wilson, R., et al.
GenBank Accession No. N84168; cDNAs from fetal heart (1996); Unpublished (1996); Liew,C.C.
GenBank Accession No. N78968; The WashU-Merck EST Project; Unpublished 1995; Hillier, L., Wilson, R., et al.
GenBank Accession No. N68345; The WashU-Merck EST Project; Unpublished 1995; Hillier, L., Wilson, R., et al.
GenBank Accession No. N67591; Generation and analysis of 280,000 human expressed sequence tags; Genome Res. 6 (9), 807-828 (1996); Hillier, L., et al.
GenBank Accession No. U47684; Identification of differentially expressed RNA in A431 cells treated with different concentration of EGF; Unpublished (1996); Yang,Y., et al.
GenBank Accession No. U47683; Identification of differentially expressed RNA in A431 cells treated with different concentration of EGF; Unpublished (1996); Yang,Y., et al.
GenBank Accession No. U47682; Identification of differentially expressed RNA in A431 cells treated with different concentration of EGF; Unpublished (1996); Yang,Y., et al.
GenBank Accession No. U47681; Identification of differentially expressed RNA in A431 cells treated with different concentration of EGF; Unpublished (1996); Yang,Y., et al.
GenBank Accession No. U47680; Identification of differentially expressed RNA in A431 cells treated with different concentration of EGF; Unpublished (1996); Yang,Y., et al.
GenBank Accession No. N50212; The WashU-Merck EST Project; Unpublished 1995; Hillier, L., Wilson, R., et al.
GenBank Accession No. N39377; The WashU-Merck EST Project; Unpublished 1995; Hillier, L., Wilson, R., et al.
GenBank Accession No. N38850; The WashU-Merck EST Project; Unpublished 1995; Hillier, L., Wilson, R., et al.
GenBank Accession No. N36498; The WashU-Merck EST Project; Unpublished 1995; Hillier, L., Wilson, R., et al.
GenBank Accession No. N31430; The WashU-Merck EST Project; Unpublished 1995; Hillier, L., Wilson, R., et al.
GenBank Accession No. H97085; The WashU-Merck EST Project; Unpublished 1995; Hillier, L., Wilson, R., et al.
GenBank Accession No. H91047; The WashU-Merck EST Project; Unpublished 1995; Hillier, L., Wilson, R., et al.
GenBank Accession No. H86405; The WashU-Merck EST Project; Unpublished 1995; Hillier, L., Wilson, R., et al.
GenBank Accession No. H84417; The WashU-Merck EST Project; Unpublished 1995; Hillier, L., Wilson, R., et al.

GenBank Accession No. H68588; Generation and analysis of 280,000 human expressed sequence tags; Genome Res. 6 (9), 807-828 (1996); Hillier, L., et al.
GenBank Accession No. H64659; Generation and analysis of 280,000 human expressed sequence tags; Genome Res. 6 (9), 807-828 (1996); Hillier, L., et al.
GenBank Accession No. H69813; Generation and analysis of 280,000 human expressed sequence tags; Genome Res. 6 (9), 807-828 (1996); Hillier, L., et al.
GenBank Accession No. H64927; Generation and analysis of 280,000 human expressed sequence tags; Genome Res. 6 (9), 807-828 (1996); Hillier, L., et al.
GenBank Accession No. H60189; The WashU-Merck EST Project; Unpublished 1995; Hillier, L., Wilson, R., et al.
GenBank Accession No. H58355; The WashU-Merck EST Project; Unpublished 1995; Hillier, L., Wilson, R., et al.
GenBank Accession No. R98591; The WashU-Merck EST Project; Unpublished 1995; Hillier, L., Wilson, R., et al.
GenBank Accession No. R97226; The WashU-Merck EST Project; Unpublished 1995; Hillier, L., Wilson, R., et al.
GenBank Accession No. T29409; Initial assessment of human gene diversity and expression patterns based upon 83 million Basepairs of cDNA sequence; Nature 377(6547 Suppl), 3-174 (1995); Adams,M.D., et al.
GenBank Accession No. T28758; Initial assessment of human gene diversity and expression patterns based upon 83 million Basepairs of cDNA sequence; Nature 377, 3-174 (1995); Adams,M.D., et al.
GenBank Accession No. T27801; Initial assessment of human gene diversity and expression patterns based upon 83 million Basepairs of cDNA sequence; Nature 377, 3-174 (1995); Adams,M.D., et al.
GenBank Accession No. T27668; Initial assessment of human gene diversity and expression patterns based upon 83 million Basepairs of cDNA sequence; Nature 377, 3-174 (1995); Adams,M.D., et al.
GenBank Accession No. H30204; The WashU-Merck EST Project; Unpublished 1995; Hillier, L., Wilson, R., et al.
GenBank Accession No. R83528; The WashU-Merck EST Project; Unpublished 1995; Hillier, L., Wilson, R., et al.
GenBank Accession No. H46786; The WashU-Merck EST Project; Unpublished 1995; Hillier, L., Wilson, R., et al.
GenBank Accession No. H46717; The WashU-Merck EST Project; Unpublished 1995; Hillier, L., Wilson, R., et al.
GenBank Accession No. H27190; The WashU-Merck EST Project; Unpublished 1995; Hillier, L., Wilson, R., et al.
GenBank Accession No. H27189; The WashU-Merck EST Project; Unpublished 1995; Hillier, L., Wilson, R., et al.
GenBank Accession No. H14216; The WashU-Merck EST Project; Unpublished 1995; Hillier, L., Wilson, R., et al.
GenBank Accession No. H15129; The WashU-Merck EST Project; Unpublished 1995; Hillier, L., Wilson, R., et al.
GenBank Accession No. H08540; The WashU-Merck EST Project; Unpublished 1995; Hillier, L., Wilson, R., et al.
GenBank Accession No. H03729; The WashU-Merck EST Project; Unpublished 1995; Hillier, L., Wilson, R., et al.
GenBank Accession No. H02836; The WashU-Merck EST Project; Unpublished 1995; Hillier, L., Wilson, R., et al.
GenBank Accession No. H00194; The WashU-Merck EST Project; Unpublished 1995; Hillier, L., Wilson, R., et al.
GenBank Accession No. R82385; The WashU-Merck EST Project; Unpublished 1995; Hillier, L., Wilson, R., et al.
GenBank Accession No. R81037; The WashU-Merck EST Project; Unpublished 1995; Hillier, L., Wilson, R., et al.
GenBank Accession No. R45640; The WashU-Merck EST Project; Unpublished 1995; Hillier, L., Wilson, R., et al.
GenBank Accession No. R52415; The WashU-Merck EST Project; Unpublished 1995; Hillier, L., Wilson, R., et al.
GenBank Accession No. R37964; The WashU-Merck EST Project; Unpublished 1995; Hillier, L., Wilson, R., et al.
GenBank Accession No. R36774; The WashU-Merck EST Project; Unpublished 1995; Hillier, L., Wilson, R., et al.
GenBank Accession No. R35776; The WashU-Merck EST Project; Unpublished 1995; Hillier, L., Wilson, R., et al.
GenBank Accession No. R35665; The WashU-Merck EST Project; Unpublished 1995; Hillier, L., Wilson, R., et al.
GenBank Accession No. R24709; The WashU-Merck EST Project; Unpublished 1995; Hillier, L., Wilson, R., et al.
GenBank Accession No. R20581; The WashU-Merck EST Project; Unpublished 1995; Hillier, L., Wilson, R., et al.
GenBank Accession No. R14663; The WashU-Merck EST Project; Unpublished 1995; Hillier, L., Wilson, R., et al.
GenBank Accession No. R13879; The WashU-Merck EST Project; Unpublished 1995; Hillier, L., Wilson, R., et al.
GenBank Accession No. R12231; The WashU-Merck EST Project; Unpublished 1995; Hillier, L., Wilson, R., et al.
GenBank Accession No. R09329; The WashU-Merck EST Project; Unpublished 1995; Hillier, L., Wilson, R., et al.
GenBank Accession No. R01932; The WashU-Merck EST Project; Unpublished 1995; Hillier, L., Wilson, R., et al.
GenBank Accession No. T79290; The WashU-Merck EST Project; Unpublished 1995; Hillier, L., Wilson, R., et al.
GenBank Accession No. T80514; The WashU-Merck EST Project; Unpublished 1995; Hillier, L., Wilson, R., et al.
GenBank Accession No. T78384; The WashU-Merck EST Project; Unpublished 1995; Hillier, L., Wilson, R., et al.
GenBank Accession No. T77496; The WashU-Merck EST Project; Unpublished 1995; Hillier, L., Wilson, R., et al.
GenBank Accession No. T77091; The WashU-Merck EST Project; Unpublished 1995; Hillier, L., Wilson, R., et al.
GenBank Accession No. T63539; Generation and analysis of 280,000 human expressed sequence tags; Genome Res. 6 (9), 807-828 (1996); Hillier, L., et al.
GenBank Accession No. T40520; Generation and analysis of 280,000 human expressed sequence tags; Genome Res. 6 (9), 807-828 (1996); Hillier, L., et al.
GenBank Accession No. T39469; Generation and analysis of 280,000 human expressed sequence tags; Genome Res. 6 (9), 807-828 (1996); Hillier, L., et al.
GenBank Accession No. T39335; Generation and analysis of 280,000 human expressed sequence tags; Genome Res. 6 (9), 807-828 (1996); Hillier, L., et al.
GenBank Accession No. T39329; Generation and analysis of 280,000 human expressed sequence tags; Genome Res. 6 (9), 807-828 (1996); Hillier, L., et al.
GenBank Accession No. T09011; Rapid cDNA sequencing (expressed sequence tags) from a directionally cloned human infant brain cDNA library; Nat. Genet. 4, 373-380 (1993); Adams,M.D., et al.
GenBank Accession No. T08853; Rapid cDNA sequencing (expressed sequence tags) from a directionally cloned human infant brain cDNA library; Nat. Genet. 4, 373-380 (1993); Adams,M.D., et al.
GenBank Accession No. T08049; Rapid cDNA sequencing (expressed sequence tags) from a directionally cloned human infant brain cDNA library; Nat. Genet. 4, 373-380 (1993); Adams,M.D., et al.
GenBank Accession No. T06741; 3,400 expressed sequence tags identify diversity of transcripts from human brain; Nat. Genet. 4, 256-267 (1993); Adams,M.D., et al.
GenBank Accession No. T06471; 3,400 expressed sequence tags identify diversity of transcripts from human brain; Nat. Genet. 4, 256-267 (1993); Adams,M.D., et al.
*Dayhoff, NP_077300.1, Gene 293 (1-2), 47-57 (2002), Rupp, P.A., et al.

* cited by examiner

FIGURE 1

ACTGCACCTCGGTTCTATCGATTGAATTCCCCGGGGATCCTCTAGAGATCCCTCGACCTC
GACCCACGCGTCCGGGCCGGAGCAGCACGGCCGCAGGACCTGGAGCTCCGGCTGCGTC
TTCCCGCAGCGCTACCCGCCATGCGCCTGCCGCGCCGGGCCGCGCTGGGGCTCCTGCCG
CTTCTGCTGCTGCTGCCGCCCGCGCCGGAGGCCGCCAAGAAGCCGACGCCCTGCCACCG
GTGCCGGGGGCTGGTGGACAAGTTTAACCAGGGGATGGTGGACACCGCAAAGAAGAAC
TTTGGCGGCGGGAACACGGCTTGGGAGGAAAAGACGCTGTCCAAGTACGAGTCCAGCG
AGATTCGCCTGCTGGAGATCCTGGAGGGGCTGTGCGAGAGCAGCGACTTCGAATGCAA
TCAGATGCTAGAGGCGCAGGAGGAGCACCTGGAGGCCTGGTGGCTGCAGCTGAAGAGC
GAATATCCTGACTTATTCGAGTGGTTTTGTGTGAAGACACTGAAAGTGTGCTGCTCTCCA
GGAACCTACGGTCCCGACTGTCTCGCATGCCAGGGCGGATCCCAGAGGCCCTGCAGCG
GGAATGGCCACTGCAGCGGAGATGGGAGCAGACAGGGCGACGGGTCCTGCCGGTGCCA
CATGGGGTACCAGGGCCCGCTGTGCACTGACTGCATGGACGGCTACTTCAGCTCGCTCC
GGAACGAGACCCACAGCATCTGCACAGCCTGTGACGAGTCCTGCAAGACGTGCTCGGG
CCTGACCAACAGAGACTGCGGCGAGTGTGAAGTGGGCTGGGTGCTGGACGAGGGCGCC
TGTGTGGATGTGGACGAGTGTGCGGCCGAGCCGCCTCCCTGCAGCGCTGCGCAGTTCTG
TAAGAACGCCAACGGCTCCTACACGTGCGAAGAGTGTGACTCCAGCTGTGTGGGCTGCA
CAGGGGAAGGCCCAGGAAACTGTAAAGAGTGTATCTCTGGCTACGCGAGGGAGCACGG
ACAGTGTGCAGATGTGGACGAGTGCTCACTAGCAGAAAAAACCTGTGTGAGGAAAAAC
GAAAACTGCTACAATACTCCAGGGAGCTACGTCTGTGTGTGTCCTGACGGCTTCGAAGA
AACGGAAGATGCCTGTGTGCCGCCGGCAGAGGCTGAAGCCACAGAAGGAGAAAGCCCG
ACACAGCTGCCCTCCCGCGAAGACCTGTAATGTGCCGGACTTACCCTTTAAATTATTCA
GAAGGATGTCCCGTGGAAAATGTGGCCCTGAGGATGCCGTCTCCTGCAGTGGACAGCG
GCGGGGAGAGGCTGCCTGCTCTCTAACGGTTGATTCTCATTTGTCCCTTAAACAGCTGC
ATTTCTTGGTTGTTCTTAAACAGACTTGTATATTTTGATACAGTTCTTTGTAATAAAATTG
ACCATTGTAGGTAATCAGGAGGAAAAAAAAAAAAAAAAAAAAAAAAAAAGGGCGGCCGCG
ACTCTAGAGTCGACCTGCAGAAGCTTGGCCGCCATGGCCCAACTTGTTTATTGCAGCTT
ATAATGGTTACAAATAAAGCAATAGCATCACAAATTTCACAAATAAAGCATTTTTTTCA
CTGCATTCTAGTTGTGGTTTGTCCAAACTCATCAATGTATCTTATCATGTCTGGATCGGG
AATTAATTCGGCGCAGCACCATGGCCTGAAATAACCTCTGAAAGAGGAACTTGGTTAGG
TACCTTCTGAGGCGGAAAGAACCAGCTGTGGAATGTGTGTCAGTTAGGGTGTGGAAAGT
CCCCAGGCTCCCCAGCAGGCAGAAGTATGCAAGCATGCATCTCAATTAGTCAGCAACCC
AGTTT

FIGURE 2

><subunit 1 of 1, 353 aa, 0 stop

><MW: 38192, pI: 4.53, NX(S/T): 2

MRLPRRAALGLLPLLLLLPPAPEAAKKPTPCHRCRGLVDKFNQGMVDTAKKNFGGGNTAW
EEKTLSKYESSEIRLLEILEGLCESSDFECNQMLEAQEEHLEAWWLQLKSEYPDLFEWFCVK
TLKVCCSPGTYGPDCLACQGGSQRPCSGNGHCSGDGSRQGDGSCRCHMGYQGPLCTDCM
DGYFSSLRNETHSICTACDESCKTCSGLTNRDCGECEVGWVLDEGACVDVDECAAEPPPCS
AAQFCKNANGSYTCEECDSSCVGCTGEGPGNCKECISGYAREHGQCADVDECSLAEKTCV
RKNENCYNTPGSYVCVCPDGFEETEDACVPPAEAEATEGESPTQLPSREDL

Signal peptide:

amino acids 1-24

N-glycosylation sites.

amino acids 190-194 and 251-255

Glycosaminoglycan attachment sites.

amino acids 149-153 and 155-159 cAMP- and cGMP-dependent protein kinase phosphorylation site.

amino acids 26-30

Casein kinase II phosphorylation sites.

amino acids 58-62, 66-70, 86-90, 197-201, 210-214, 255-259, 295-299, 339-343 and 349-353

Tyrosine kinase phosphorylation site.

amino acids 303-310

N-myristoylation sites.

amino acids 44-50, 54-60, 55-61, 81-87, 150-156, 158-164, 164-170, 252-258 and 313-319

Aspartic acid and asparagine hydroxylation site.

amino acids 308-320

EGF-like domain cysteine pattern signature.

amino acids 166-178

Leucine zipper pattern.

amino acids 94-116

FIGURE 3

CAGGTCCAACTGCACCTCGGTTCTATCGATTGAATTCCCCGGGGATCCTCTAGAGATCC
CTCGACCTCGACCCACGCGTCCGCCAGGCCGGGAGGCGACGCGCCCAGCCGTCTAAAC
GGGAACAGCCCTGGCTGAGGGAGCTGCAGCGCAGCAGAGTATCTGACGGCGCCAGGTT
GCGTAGGTGCGGCACGAGGAGTTTTCCCGGCAGCGAGGAGGTCCTGAGCAGCATGGCC
CGGAGGAGCGCCTTCCCTGCCGCCGCGCTCTGGCTCTGGAGCATCCTCCTGTGCCTGCT
GGCACTGCGGGCGGAGGCCGGGCCGCCGCAGGAGGAGAGCCTGTACCTATGGATCGAT
GCTCACCAGGCAAGAGTACTCATAGGATTTGAAGAAGATATCCTGATTGTTTCAGAGGG
GAAAATGGCACCTTTTACACATGATTTCAGAAAAGCGCAACAGAGAATGCCAGCTATTC
CTGTCAATATCCATTCCATGAATTTTACCTGGCAAGCTGCAGGGCAGGCAGAATACTTC
TATGAATTCCTGTCCTTGCGCTCCCTGGATAAAGGCATCATGGCAGATCCAACCGTCAA
TGTCCCTCTGCTGGGAACAGTGCCTCACAAGGCATCAGTTGTTCAAGTTGGTTTCCCATG
TCTTGGAAAACAGGATGGGGTGGCAGCATTTGAAGTGGATGTGATTGTTATGAATTCTG
AAGGCAACACCATTCTCCAAACACCTCAAAATGCTATCTTCTTTAAAACATGTCAACAA
GCTGAGTGCCCAGGCGGGTGCCGAAATGGAGGCTTTTGTAATGAAAGACGCATCTGCG
AGTGTCCTGATGGGTTCCACGGACCTCACTGTGAGAAAGCCCTTTGTACCCCACGATGT
ATGAATGGTGGACTTTGTGTGACTCCTGGTTTCTGCATCTGCCCACCTGGATTCTATGGA
GTGAACTGTGACAAAGCAAACTGCTCAACCACCTGCTTTAATGGAGGGACCTGTTTCTA
CCCTGGAAAATGTATTTGCCCTCCAGGACTAGAGGGAGAGCAGTGTGAAATCAGCAAA
TGCCCACAACCCTGTCGAAATGGAGGTAAATGCATTGGTAAAAGCAAATGTAAGTGTTC
CAAAGGTTACCAGGGAGACCTCTGTTCAAAGCCTGTCTGCGAGCCTGGCTGTGGTGCAC
ATGGAACCTGCCATGAACCCAACAAATGCCAATGTCAAGAAGGTTGGCATGGAAGACA
CTGCAATAAAAGGTACGAAGCCAGCCTCATACATGCCCTGAGGCCAGCAGGCGCCCAG
CTCAGGCAGCACACGCCTTCACTTAAAAAGGCCGAGGAGCGGCGGGATCCACCTGAAT
CCAATTACATCTGGTGAACTCCGACATCTGAAACGTTTTAAGTTACACCAAGTTCATAG
CCTTTGTTAACCTTTCATGTGTTGAATGTTCAAATAATGTTCATTACACTTAAGAATACT
GGCCTGAATTTTATTAGCTTCATTATAAATCACTGAGCTGATATTTACTCTTCCTTTTAA
GTTTTCTAAGTACGTCTGTAGCATGATGGTATAGATTTTCTTGTTTCAGTGCTTTGGGAC
AGATTTTATATTATGTCAATTGATCAGGTTAAAATTTTCAGTGTGTAGTTGGCAGATATT
TTCAAAATTACAATGCATTTATGGTGTCTGGGGGCAGGGGAACATCAGAAAGGTTAAAT
TGGGCAAAAATGCGTAAGTCACAAGAATTTGGATGGTGCAGTTAATGTTGAAGTTACAG
CATTTCAGATTTTATTGTCAGATATTTAGATGTTTGTTACATTTTTAAAAATTGCTCTTAA
TTTTTAAACTCTCAATACAATATATTTTGACCTTACCATTATTCCAGAGATTCAGTATTA
AAAAAAAAAAAATTACACTGTGGTAGTGGCATTTAAACAATATAATATATTCTAAACAC
AATGAAATAGGGAATATAATGTATGAACTTTTTGCATTGGCTTGAAGCAATATAATATA
TTGTAAACAAAACACAGCTCTTACCTAATAAACATTTTATACTGTTTGTATGTATAAAAT
AAAGGTGCTGCTTTAGTTTTTTGGAAAAAAAAAAAAAAAAAAAAAAAAAAAAAAAAAAA
AAAAAAGGGCGGCCGCGACTCTAGAGTCGACCTGCAGAAGCTTGGCCGCCATGGCCC
AACTTGTTTATTGCAGCTTATAATG

FIGURE 4

></usr/seqdb2/sst/DNA/Dnaseqs.min/ss.DNA33094
><subunit 1 of 1, 379 aa, 0 stop
><MW: 41528, pI: 7.97, NX(S/T): 2

MARRSAFPAAALWLWSILLCLLALRAEAGPPQEESLYLWIDAHQARVLIGFEEDILIVSEGK
MAPFTHDFRKAQQRMPAIPVNIHSMNFTWQAAGQAEYFYEFLSLRSLDKGIMADPTVNVPL
LGTVPHKASVVQVGFPCLGKQDGVAAFEVDVIVMNSEGNTILQTPQNAIFFKTCQQAECPG
GCRNGGFCNERRICECPDGFHGPHCEKALCTPRCMNGGLCVTPGFCICPPGFYGVNCDKAN
CSTTCFNGGTCFYPGKCICPPGLEGEQCEISKCPQPCRNGGKCIGKSKCKCSKGYQGDLCSK
PVCEPGCGAHGTCHEPNKCQCQEGWHGRHCNKRYEASLIHALRPAGAQLRQHTPSLKKAE
ERRDPPESNYIW

Signal peptide:

amino acids 1-28

N-glycosylation site.

amino acids 88-92, 245-249

Casein kinase II phosphorylation site.

amino acids 319-323

Tyrosine kinase phosphorylation site.

amino acids 370-378

N-myristoylation sites.

amino acids 184-190, 185-191, 189-195, 315-321

ATP/GTP-binding site motif A (P-loop).

amino acids 285-293

EGF-like domain cysteine pattern signature.

amino acids 198-210, 230-242, 262-274, 294-306, 326-338

SEQUENCE LISTING

<160> NUMBER OF SEQ ID NOS: 15

<210> SEQ ID NO 1
<211> LENGTH: 1825
<212> TYPE: DNA
<213> ORGANISM: Homo sapiens

<400> SEQUENCE: 1

```
actgcacctc ggttctatcg attgaattcc ccggggatcc tctagagatc cctcgacctc      60
gacccacgcg tccgggccgg agcagcacgg ccgcaggacc tggagctccg gctgcgtctt     120
cccgcagcgc tacccgccat gcgcctgccg cgccgggccg cgctggggct cctgccgctt     180
ctgctgctgc tgccgcccgc gccggaggcc gccaagaagc cgacgccctg ccaccggtgc     240
cgggggctgg tggacaagtt taaccagggg atggtggaca ccgcaaagaa gaactttggc     300
ggcgggaaca cggcttggga ggaaaagacg ctgtccaagt acgagtccag cgagattcgc     360
ctgctggaga tcctggaggg gctgtgcgag agcagcgact tcgaatgcaa tcagatgcta     420
gaggcgcagg aggagcacct ggaggcctgg tggctgcagc tgaagagcga atatcctgac     480
ttattcgagt ggttttgtgt gaagacactg aaagtgtgct gctctccagg aacctacggt     540
cccgactgtc tcgcatgcca gggcggatcc cagaggccct gcagcgggaa tggccactgc     600
agcggagatg ggagcagaca gggcgacggg tcctgccggt gccacatggg gtaccagggc     660
ccgctgtgca ctgactgcat ggacggctac ttcagctcgc tccggaacga gacccacagc     720
atctgcacag cctgtgacga gtcctgcaag acgtgctcgg gcctgaccaa cagagactgc     780
ggcgagtgtg aagtgggctg ggtgctggac gagggcgcct gtgtggatgt ggacgagtgt     840
gcggccgagc cgcctccctg cagcgctgcg cagttctgta agaacgccaa cggctcctac     900
acgtgcgaag agtgtgactc cagctgtgtg ggctgcacag gggaaggccc aggaaactgt     960
aaagagtgta tctctggcta cgcgagggag cacggacagt gtgcagatgt ggacgagtgc    1020
tcactagcag aaaaaacctg tgtgaggaaa aacgaaaact gctacaatac tccagggagc    1080
tacgtctgtg tgtgtcctga cggcttcgaa gaaacggaag atgcctgtgt gccgccggca    1140
gaggctgaag ccacagaagg agaaagcccg acacagctgc cctcccgcga agacctgtaa    1200
tgtgccggac ttacccttta aattattcag aaggatgtcc cgtggaaaat gtggccctga    1260
ggatgccgtc tcctgcagtg gacagcggcg gggagaggct gcctgctctc taacggttga    1320
ttctcatttg tcccttaaac agctgcattt cttggttgtt cttaaacaga cttgtatatt    1380
ttgatacagt tctttgtaat aaaattgacc attgtaggta atcaggagga aaaaaaaaa    1440 aaaaaaaaa aagggcggc cgcgactcta gagtcgacct gcagaagctt ggccgccatg    1500
gcccaacttg tttattgcag cttataatgg ttacaaataa agcaatagca tcacaaattt    1560
cacaaataaa gcattttttt cactgcattc tagttgtggt ttgtccaaac tcatcaatgt    1620
atcttatcat gtctggatcg ggaattaatt cggcgcagca ccatggcctg aaataacctc    1680
tgaaagagga acttggttag gtaccttctg aggcggaaag aaccagctgt ggaatgtgtg    1740
```
tcagttaggg tgtggaaagt ccccaggctc cccagcaggc agaagtatgc aagcatgcat    1800
ctcaattagt cagcaaccca gtttt                                         1825

<210> SEQ ID NO 2
<211> LENGTH: 353
<212> TYPE: PRT
<213> ORGANISM: Homo sapiens

<400> SEQUENCE: 2

Met Arg Leu Pro Arg Arg Ala Ala Leu Gly Leu Leu Pro Leu Leu
 1               5                  10                  15

Leu Leu Pro Pro Ala Pro Glu Ala Ala Lys Lys Pro Thr Pro Cys His
                20                  25                  30

Arg Cys Arg Gly Leu Val Asp Lys Phe Asn Gln Gly Met Val Asp Thr
            35                  40                  45

Ala Lys Lys Asn Phe Gly Gly Gly Asn Thr Ala Trp Glu Glu Lys Thr
        50                  55                  60

Leu Ser Lys Tyr Glu Ser Ser Glu Ile Arg Leu Leu Glu Ile Leu Glu
65                  70                  75                  80

Gly Leu Cys Glu Ser Ser Asp Phe Glu Cys Asn Gln Met Leu Glu Ala
                85                  90                  95

Gln Glu Glu His Leu Glu Ala Trp Trp Leu Gln Leu Lys Ser Glu Tyr
            100                 105                 110

Pro Asp Leu Phe Glu Trp Phe Cys Val Lys Thr Leu Lys Val Cys Cys
        115                 120                 125

Ser Pro Gly Thr Tyr Gly Pro Asp Cys Leu Ala Cys Gln Gly Gly Ser
    130                 135                 140

Gln Arg Pro Cys Ser Gly Asn Gly His Cys Ser Gly Asp Gly Ser Arg
145                 150                 155                 160

Gln Gly Asp Gly Ser Cys Arg Cys His Met Gly Tyr Gln Gly Pro Leu
                165                 170                 175

Cys Thr Asp Cys Met Asp Gly Tyr Phe Ser Ser Leu Arg Asn Glu Thr
            180                 185                 190

His Ser Ile Cys Thr Ala Cys Asp Glu Ser Cys Lys Thr Cys Ser Gly
        195                 200                 205

Leu Thr Asn Arg Asp Cys Gly Glu Cys Glu Val Gly Trp Val Leu Asp
    210                 215                 220

Glu Gly Ala Cys Val Asp Val Asp Glu Cys Ala Ala Glu Pro Pro Pro
225                 230                 235                 240

Cys Ser Ala Ala Gln Phe Cys Lys Asn Ala Asn Gly Ser Tyr Thr Cys
                245                 250                 255

Glu Glu Cys Asp Ser Ser Cys Val Gly Cys Thr Gly Glu Gly Pro Gly
            260                 265                 270

Asn Cys Lys Glu Cys Ile Ser Gly Tyr Ala Arg Glu His Gly Gln Cys
        275                 280                 285

Ala Asp Val Asp Glu Cys Ser Leu Ala Glu Lys Thr Cys Val Arg Lys
    290                 295                 300

Asn Glu Asn Cys Tyr Asn Thr Pro Gly Ser Tyr Val Cys Val Cys Pro
305                 310                 315                 320

Asp Gly Phe Glu Glu Thr Glu Asp Ala Cys Val Pro Pro Ala Glu Ala
                325                 330                 335

Glu Ala Thr Glu Gly Glu Ser Pro Thr Gln Leu Pro Ser Arg Glu Asp
            340                 345                 350

Leu

<210> SEQ ID NO 3
<211> LENGTH: 2206
<212> TYPE: DNA
<213> ORGANISM: Homo sapiens

<400> SEQUENCE: 3

| | | | | | |
|---|---|---|---|---|---|
| caggtccaac | tgcacctcgg | ttctatcgat | tgaattcccc | ggggatcctc | tagagatccc | 60 |
| tcgacctcga | cccacgcgtc | cgccaggccg | ggaggcgacg | cgcccagccg | tctaaacggg | 120 |
| aacagccctg | gctgagggag | ctgcagcgca | gcagagtatc | tgacggcgcc | aggttgcgta | 180 |
| ggtgcggcac | gaggagtttt | cccggcagcg | aggaggtcct | gagcagcatg | gcccggagga | 240 |
| gcgccttccc | tgccgccgcg | ctctggctct | ggagcatccc | cctgtgcctg | ctggcactgc | 300 |
| gggcggaggc | cgggccgccg | caggaggaga | gcctgtacct | atggatcgat | gctcaccagg | 360 |
| caagagtact | cataggattt | gaagaagata | tcctgattgt | tcagagggg | aaaatggcac | 420 |
| cttttacaca | tgatttcaga | aaagcgcaac | agagaatgcc | agctattcct | gtcaatatcc | 480 |
| attccatgaa | ttttacctgg | caagctgcag | ggcaggcaga | atacttctat | gaattcctgt | 540 |
| ccttgcgctc | cctggataaa | ggcatcatgg | cagatccaac | cgtcaatgtc | cctctgctgg | 600 |
| gaacagtgcc | tcacaaggca | tcagttgttc | aagttggttt | cccatgtctt | ggaaaacagg | 660 |
| atggggtggc | agcatttgaa | gtggatgtga | ttgttatgaa | ttctgaaggc | aacaccattc | 720 |
| tccaaacacc | tcaaaatgct | atcttcttta | aaacatgtca | acaagctgag | tgcccaggcg | 780 |
| ggtgccgaaa | tggaggcttt | tgtaatgaaa | gacgcatctg | cgagtgtcct | gatgggttcc | 840 |
| acggacctca | ctgtgagaaa | gcccttgta | ccccacgatg | tatgaatggt | ggactttgtg | 900 |
| tgactcctgg | tttctgcatc | tgcccacctg | gattctatgg | agtgaactgt | gacaaagcaa | 960 |
| actgctcaac | cacctgcttt | aatgagggga | cctgtttcta | ccctggaaaa | tgtatttgcc | 1020 |
| ctccaggact | agagggagag | cagtgtgaaa | tcagcaaatg | cccacaaccc | tgtcgaaatg | 1080 |
| gaggtaaatg | cattggtaaa | agcaaatgta | agtgttccaa | aggttaccag | ggagacctct | 1140 |
| gttcaaagcc | tgtctgcgag | cctggctgtg | gtgcacatgg | aacctgccat | gaacccaaca | 1200 |
| aatgccaatg | tcaagaaggt | tggcatgaa | gacactgcaa | taaaggtac | gaagccagcc | 1260 |
| tcatacatgc | cctgaggcca | gcaggcgccc | agctcaggca | gcacacgcct | tcacttaaaa | 1320 |
| aggccgagga | gcggcgggat | ccacctgaat | ccaattacat | ctggtgaact | ccgacatctg | 1380 |
| aaacgtttta | agttacacca | agttcatagc | ctttgttaac | ctttcatgtg | ttgaatgttc | 1440 |
| aaataatgtt | cattcacactt | aagaatactg | gcctgaattt | tattagcttc | attataaatc | 1500 |
| actgagctga | tatttactct | tccttttaag | ttttctaagt | acgtctgtag | catgatggta | 1560 |
| tagattttct | tgtttcagtg | ctttgggaca | gattttatat | tatgtcaatt | gatcaggtta | 1620 |
| aaattttcag | tgtgtagttg | gcagatattt | tcaaaattac | aatgcattta | tggtgtctgg | 1680 |
| gggcagggga | acatcagaaa | ggttaaattg | gcaaaaatg | cgtaagtcac | aagaatttgg | 1740 |
| atggtgcagt | taatgttgaa | gttacagcat | ttcagatttt | attgtcagat | atttagatgt | 1800 |
| ttgttacatt | tttaaaaatt | gctcttaatt | tttaaactct | caatacaata | tattttgacc | 1860 |
| ttaccattat | tccagagatt | cagtattaaa | aaaaaaaaa | ttcactgtg | gtagtggcat | 1920 |
| ttaaacaata | taatatattc | taaacacaat | gaaatagga | atataatgta | tgaacttttt | 1980 |
| gcattggctt | gaagcaatat | aatatatattgt | aaacaaaaca | cagctcttac | ctaataaaca | 2040 |
| ttttatactg | tttgtatgta | taaataaag | gtgctgcttt | agttttttgg | aaaaaaaaaa | 2100 |

```
aaaaaaaaaa aaaaaaaaaa aaaaaaaaaa gggcggccgc gactctagag tcgacctgca    2160
gaagcttggc cgccatggcc caacttgttt attgcagctt ataatg                    2206
```

<210> SEQ ID NO 4
<211> LENGTH: 379
<212> TYPE: PRT
<213> ORGANISM: Homo sapiens

<400> SEQUENCE: 4

```
Met Ala Arg Arg Ser Ala Phe Pro Ala Ala Leu Trp Leu Trp Ser
 1               5                  10                  15

Ile Leu Leu Cys Leu Leu Ala Leu Arg Ala Glu Ala Gly Pro Pro Gln
                20                  25                  30

Glu Glu Ser Leu Tyr Leu Trp Ile Asp Ala His Gln Ala Arg Val Leu
            35                  40                  45

Ile Gly Phe Glu Glu Asp Ile Leu Ile Val Ser Glu Gly Lys Met Ala
        50                  55                  60

Pro Phe Thr His Asp Phe Arg Lys Ala Gln Gln Arg Met Pro Ala Ile
65                  70                  75                  80

Pro Val Asn Ile His Ser Met Asn Phe Thr Trp Gln Ala Ala Gly Gln
                85                  90                  95

Ala Glu Tyr Phe Tyr Glu Phe Leu Ser Leu Arg Ser Leu Asp Lys Gly
            100                 105                 110

Ile Met Ala Asp Pro Thr Val Asn Val Pro Leu Leu Gly Thr Val Pro
        115                 120                 125

His Lys Ala Ser Val Val Gln Val Gly Phe Pro Cys Leu Gly Lys Gln
145                 150                 155                 160

Asp Gly Val Ala Ala Phe Glu Val Asp Val Ile Val Met Asn Ser Glu
145                 150                 155                 160

Gly Asn Thr Ile Leu Gln Thr Pro Gln Asn Ala Ile Phe Phe Lys Thr
                165                 170                 175

Cys Gln Gln Ala Glu Cys Pro Gly Gly Cys Arg Asn Gly Gly Phe Cys
            180                 185                 190

Asn Glu Arg Arg Ile Cys Glu Cys Pro Asp Gly Phe His Gly Pro His
        195                 200                 205

Cys Glu Lys Ala Leu Cys Thr Pro Arg Cys Met Asn Gly Gly Leu Cys
    210                 215                 220

Val Thr Pro Gly Phe Cys Ile Cys Pro Pro Gly Phe Tyr Gly Val Asn
225                 230                 235                 240

Cys Asp Lys Ala Asn Cys Ser Thr Thr Cys Phe Asn Gly Gly Thr Cys
                245                 250                 255

Phe Tyr Pro Gly Lys Cys Ile Cys Pro Pro Gly Leu Glu Gly Glu Gln
            260                 265                 270

Cys Glu Ile Ser Lys Cys Pro Gln Pro Cys Arg Asn Gly Gly Lys Cys
        275                 280                 285

Ile Gly Lys Ser Lys Cys Lys Cys Ser Lys Gly Tyr Gln Gly Asp Leu
    290                 295                 300

Cys Ser Lys Pro Val Cys Glu Pro Gly Cys Gly Ala His Gly Thr Cys
305                 310                 315                 320

His Glu Pro Asn Lys Cys Gln Cys Gln Glu Gly Trp His Gly Arg His
                325                 330                 335

Cys Asn Lys Arg Tyr Glu Ala Ser Leu Ile His Ala Leu Arg Pro Ala
            340                 345                 350
```

```
Gly Ala Gln Leu Arg Gln His Thr Pro Ser Leu Lys Lys Ala Glu Glu
        355                 360                 365

Arg Arg Asp Pro Pro Glu Ser Asn Tyr Ile Trp
    370                 375
```

<210> SEQ ID NO 5
<211> LENGTH: 45
<212> TYPE: DNA
<213> ORGANISM: Artificial Sequence
<220> FEATURE:
<223> OTHER INFORMATION: Synthetic Oligonucleotide Probe

<400> SEQUENCE: 5
agggagcacg gacagtgtgc agatgtggac gagtgctcac tagca         45

<210> SEQ ID NO 6
<211> LENGTH: 21
<212> TYPE: DNA
<213> ORGANISM: Artificial Sequence
<220> FEATURE:
<223> OTHER INFORMATION: Synthetic Oligonucleotide Primer

<400> SEQUENCE: 6
agagtgtatc tctggctacg c         21

<210> SEQ ID NO 7
<211> LENGTH: 22
<212> TYPE: DNA
<213> ORGANISM: Artificial Sequence
<220> FEATURE:
<223> OTHER INFORMATION: Synthetic Oligonucleotide Primer

<400> SEQUENCE: 7
taagtccggc acattacagg tc         22

<210> SEQ ID NO 8
<211> LENGTH: 49
<212> TYPE: DNA
<213> ORGANISM: Artificial Sequence
<220> FEATURE:
<223> OTHER INFORMATION: Synthetic Oligonucleotide Probe

<400> SEQUENCE: 8
cccacgatgt atgaatggtg gactttgtgt gactcctggt ttctgcatc         49

<210> SEQ ID NO 9
<211> LENGTH: 22
<212> TYPE: DNA
<213> ORGANISM: Artificial Sequence
<220> FEATURE:
<223> OTHER INFORMATION: Synthetic Oligonucleotide Primer

<400> SEQUENCE: 9
aaagacgcat ctgcgagtgt cc         22

<210> SEQ ID NO 10
<211> LENGTH: 23
<212> TYPE: DNA
<213> ORGANISM: Artificial Sequence
<220> FEATURE:
<223> OTHER INFORMATION: Synthetic Oligonucleotide Primer

<400> SEQUENCE: 10
tgctgatttc acactgctct ccc         23

```
-continued

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 11
cagaaggatg tcccgtggaa                                              20

<210> SEQ ID NO 12
<211> LENGTH: 17
<212> TYPE: DNA
<213> ORGANISM: Artificial Sequence
<220> FEATURE:
<223> OTHER INFORMATION: Synthetic Oligonucleotide Primer

<400> SEQUENCE: 12
gccgctgtcc actgcag                                                 17

<210> SEQ ID NO 13
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 13
gacggcatcc tcagggccac a                                            21

<210> SEQ ID NO 14
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 14
ggattctaat acgactcact atagggctca gaaaagcgca acagagaa                48

<210> SEQ ID NO 15
<211> LENGTH: 47
<212> TYPE: DNA
<213> ORGANISM: Artificial Sequence
<220> FEATURE:
<223> OTHER INFORMATION: Synthetic Oligonucleotide Probe

<400> SEQUENCE: 15
ctatgaaatt aaccctcact aaagggatgt cttccatgcc aaccttc                 47
```

US 7,449,551 B2

PRO211 POLYPEPTIDES

RELATED APPLICATIONS

This application is a continuation of, and claims priority under 35 USC §120 to, U.S. application Ser. No. 09/905,075 filed Jul. 13, 2001, which is a continuation of, and claims priority under 35 USC §120 to, U.S. application Ser. No. 09/665,350 filed Sep. 18, 2000, which is a continuation of, and claims priority under 35 USC §120 to, PCT Application PCT/US00/04414 filed Feb. 22, 2000, which is a continuation-in-part of, and claims priority under 35 USC §120 to, PCT Application PCT/US99/23089 filed Oct. 5, 1999, which claims priority under 35 USC §119 to U.S. Provisional Application 60/104,080 filed Oct. 13, 1998, where PCT Application PCT/US99/23089 filed Oct. 5, 1999 is a continuation-in-part of, and claims priority under 35 USC §120 to PCT Application PCT/US98/19330 filed Sep. 16, 1998, which is a continuation-in-part of, and claims priority under 35 USC §120 to, PCT Application PCT/US98/18824 filed Sep. 10, 1998, which claims priority under 35 USC §119 to U.S. Provisional Application 60/059,263 filed Sep. 18, 1997, the entire disclosures of which are hereby expressly incorporated by reference.

FIELD OF THE INVENTION

The present invention relates generally to the identification and isolation of novel DNA and to the recombinant production of novel polypeptides.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., *Proc. Natl. Acad. Sci.* 93:7108-7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

PRO211 and PRO217

Epidermal growth factor (EGF) is a conventional mitogenic factor that stimulates the proliferation of various types of cells including epithelial cells and fibroblasts. EGF binds to and activates the EGF receptor (EGFR), which initiates intracellular signaling and subsequent effects. The EGFR is expressed in neurons of the cerebral cortex, cerebellum, and hippocampus in addition to other regions of the central nervous system (CNS). In addition, EGF is also expressed in various regions of the CNS. Therefore, EGF acts not only on mitotic cells, but also on postmitotic neurons. In fact, many studies have indicated that EGF has neurotrophic or neuromodulatory effects on various types of neurons in the CNS. For example, EGF acts directly on cultured cerebral cortical and cerebellar neurons, enhancing neurite outgrowth and survival. On the other hand, EGF also acts on other cell types, including septal cholinergic and mesencephalic dopaminergic neurons, indirectly through glial cells. Evidence of the effects of EGF on neurons in the CNS is accumulating, but the mechanisms of action remain essentially unknown. EGF-induced signaling in mitotic cells is better understood than in postmitotic neurons. Studies of cloned pheochromocytoma PC12 cells and cultured cerebral cortical neurons have suggested that the EGF-induced neurotrophic actions are mediated by sustained activation of the EGFR and mitogen-activated protein kinase (MAPK) in response to EGF. The sustained intracellular signaling correlates with the decreased rate of EGFR down-regulation, which might determine the response of neuronal cells to EGF. It is likely that EGF is a multi-potent growth factor that acts upon various types of cells including mitotic cells and postmitotic neurons.

EGF is produced by the salivary and Brunner's glands of the gastrointestinal system, kidney, pancreas, thyroid gland, pituitary gland, and the nervous system, and is found in body fluids such as saliva, blood, cerebrospinal fluid (CSF), urine, amniotic fluid, prostatic fluid, pancreatic juice, and breast milk, Plata-Salaman, *Peptides* 12: 653-663 (1991).

EGF is mediated by its membrane specific receptor, which contains an intrinsic tyrosine kinase. Stoscheck et al, *J. Cell Biochem.* 31:135-152 (1986). EGF is believed to function by binding to the extracellular portion of its receptor which induces a transmembrane signal that activates the intrinsic tyrosine kinase.

Purification and sequence analysis of the EGF-like domain has revealed the presence of six conserved cysteine residues which cross-bind to create three peptide loops, Savage et al., *J. Biol. Chem.* 248: 7669-7672 (1979). It is now generally known that several other peptides can react with the EGF receptor which share the same generalized motif $X_nCX_7CX_{4/5}CX_{10}CXCX_5GX_2CX_n$, where X represents any non-cysteine amino acid, and n is a variable repeat number. Non isolated peptides having this motif include TGF-α, amphiregulin, schwannoma-derived growth factor (SDGF), heparin-binding EGF-like growth factors and certain virally encoded peptides (e.g., Vaccinia virus, Reisner, *Nature* 313: 801-803 (1985), Shope fibroma virus, Chang et al., Mol Cell Biol. 7: 535-540 (1987), Molluscum contagiosum, Porter and Archard, *J. Gen. Virol.* 68: 673-682 (1987), and Myxoma virus, Upton et al., *J. Virol.* 61: 1271-1275 (1987), Prigent and Lemoine, *Prog. Growth Factor Res.* 4: 1-24 (1992).

EGF-like domains are not confined to growth factors but have been observed in a variety of cell-surface and extracellular proteins which have interesting properties in cell adhesion, protein-protein interaction and development, Laurence and Gusterson, *Tumor Biol.* 11: 229-261 (1990). These proteins include blood coagulation factors (factors VI, IX, X, XII, protein C, protein S, protein Z, tissue plasminogen activator, urokinase), extracellular matrix components (laminin, cytotactin, entactin), cell surface receptors (LDL receptor, thrombomodulin receptor) and immunity-related proteins (complement Clr, uromodulin).

Even more interesting, the general structure pattern of EGF-like precursors is preserved through lower organisms as well as in mammalian cells. A number of genes with developmental significance have been identified in invertebrates with EGF-like repeats. For example, the notch gene of *Drosophila* encodes 36 tandemly arranged 40 amino acid repeats which show homology to EGF, Wharton et al., *Cell* 43: 557-581 (1985). Hydropathy plots indicate a putative membrane spanning domain, with the EGF-related sequences being located on the extracellular side of the membrane. Other homeotic genes with EGF-like repeats include Delta, 95F and 5ZD which were identified using probes based on Notch, and the nematode gene Lin-12 which encodes a putative receptor for a developmental signal transmitted between two specified cells.

Specifically, EGF has been shown to have potential in the preservation and maintenance of gastrointestinal mucosa and the repair of acute and chronic mucosal lesions, Konturek et al., *Eur. J. Gastroenterol Hepatol.* 7 (10), 933-37 (1995), including the treatment of necrotizing enterocolitis, Zollinger-Ellison syndrome, gastrointestinal ulceration gastrointestinal ulcerations and congenital microvillus atrophy, Guglietta and Sullivan, *Eur. J. Gastroenterol Hepatol*, 7(10), 945-50 (1995). Additionally, EGF has been implicated in hair follicle differentiation; du Cros, *J. Invest. Dermatol.* 101 (1 Suppl.), 106S-113S (1993), Hillier, *Clin. Endocrinol.* 33(4), 427-28 (1990); kidney function, Hamm et al., *Semin. Nephrol.* 13 (1): 109-15 (1993), Harris, *Am. J. Kidney Dis.* 17(6): 627-30 (1991); tear fluid, van Setten et al., *Int. Ophthalmol* 15(6); 359-62 (1991); vitamin K mediated blood coagulation, Stenflo et al., *Blood* 78(7): 1637-51 (1991). EGF is also implicated various skin disease characterized by abnormal keratinocyte differentiation, e.g., psoriasis, epithelial cancers such as squamous cell carcinomas of the lung, epidermoid carcinoma of the vulva and gliomas. King et al., *Am. J. Med. Sci.* 296: 154-158 (1988).

Of great interest is mounting evidence that genetic alterations in growth factors signaling pathways are closely linked to developmental abnormalities and to chronic diseases including cancer. Aaronson, *Science* 254: 1146-1153 (1991). For example, c-erb-2 (also known as HER-2), a proto-oncogene with close structural similarity to EGF receptor protein, is overexpressed in human breast cancer. King et al., *Science* 229: 974-976 (1985); Gullick, *Hormones and their actions*, Cooke et al., eds, Amsterdam, Elsevier, pp 349-360 (1986).

We herein describe the identification and characterization of novel polypeptides having homology to EGF, wherein those polypeptides are herein designated PRO211 and PRO217.

Summary of the Invention

PRO211 and PRO217

Applicants have identified cDNA clones that encode novel polypeptides having homology to EGF, designated in the present application as "PRO211" and "PRO217" polypeptides.

In one embodiment, the invention provides an isolated nucleic acid molecule comprising DNA encoding a PRO211 or PRO217 polypeptide. In one aspect, the isolated nucleic acid comprises DNA encoding EGF-like homologue PRO211 and PRO217 polypeptides of FIG. 2 (SEQ ID NO:2) and/or 4 (SEQ ID NO:4) indicated in FIG. 1 (SEQ ID NO1) and/or FIG. 3 (SEQ ID NO:3), respectively, or is complementary to such encoding nucleic acid sequence, and remains stably bound to it under at least moderate, and optionally, under high stringency conditions.

In another embodiment, the invention provides isolated PRO211 and PRO217 EGF-like homologue PRO211 and PRO217 polypeptides. In particular, the invention provides isolated native sequence PRO211 and PRO217 EGF-like homologue polypeptides, which in one embodiment, includes an amino acid sequence comprising residues: 1 to 353 of FIG. 2 (SEQ ID NO:2) or (2) 1 to 379 of FIG. 4 (SEQ ID NO: 4).

Additional Embodiments

In other embodiments of the present invention, the invention provides vectors comprising DNA encoding any of the herein described polypeptides. Host cell comprising any such vector are also provided. By way of example, the host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In another embodiment, the invention provides an antibody which specifically binds to any of the above or below described polypeptides. Optionally, the antibody is a monoclonal antibody, humanized antibody, antibody fragment or single-chain antibody.

In yet other embodiments, the invention provides oligonucleotide probes useful for isolating genomic and cDNA nucleotide sequences, wherein those probes may be derived from any of the above or below described nucleotide sequences.

In other embodiments, the invention provides an isolated nucleic acid molecule comprising a nucleotide sequence that encodes a PRO polypeptide.

In one aspect, the isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule encoding a PRO polypeptide having a full-length amino acid sequence as disclosed herein, an amino acid sequence lacking the signal peptide as disclosed herein or an extracellular domain of a transmembrane protein, with or without the signal peptide, as disclosed herein, or (b) the complement of the DNA molecule of (a).

In other aspects, the isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule comprising the coding sequence of a full-length PRO polypeptide cDNA as disclosed herein, the coding sequence of a PRO polypeptide lacking the signal peptide as disclosed herein or the coding sequence of an extracellular domain of a transmembrane PRO polypeptide, with or without the signal peptide, as disclosed herein, or (b) the complement of the DNA molecule of (a).

In a further aspect, the invention concerns an isolated nucleic acid molecule comprising a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule that encodes the same mature polypeptide encoded by any of the human protein cDNAs deposited with the ATCC as disclosed herein, or (b) the complement of the DNA molecule of (a).

Another aspect the invention provides an isolated nucleic acid molecule comprising a nucleotide sequence encoding a PRO polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO polypeptides are contemplated.

Another embodiment is directed to fragments of a PRO polypeptide coding sequence, or the complement thereof, that may find use as, for example, hybridization probes or for encoding fragments of a PRO polypeptide that may optionally encode a polypeptide comprising a binding site for an anti-PRO antibody. Such nucleic acid fragments are usually at least about 20 nucleotides in length, preferably at least about 30 nucleotides in length, more preferably at least about 40 nucleotides in length, yet more preferably at least about 50 nucleotides in length, yet more preferably at least about 60 nucleotides in length, yet more preferably at least about 70 nucleotides in length, yet more preferably at least about 80 nucleotides in length, yet more preferably at least about 90 nucleotides in length, yet more preferably at least about 100 nucleotides in length, yet more preferably at least about 110 nucleotides in length, yet more preferably at least about 120 nucleotides in length, yet more preferably at least about 130 nucleotides in length, yet more preferably at least about 140 nucleotides in length, yet more preferably at least about 150 nucleotides in length, yet more preferably at least about 160 nucleotides in length, yet more preferably at least about 170 nucleotides in length, yet more preferably at least about 180 nucleotides in length, yet more preferably at least about 190 nucleotides in length, yet more preferably at least about 200 nucleotides in length, yet more preferably at least about 250 nucleotides in length, yet more preferably at least about 300 nucleotides in length, yet more preferably at least about 350 nucleotides in length, yet more preferably at least about 400 nucleotides in length, yet more preferably at least about 450 nucleotides in length, yet more preferably at least about 500 nucleotides in length, yet more preferably at least about 600 nucleotides in length, yet more preferably at least about 700 nucleotides in length, yet more preferably at least about 800 nucleotides in length, yet more preferably at least about 900 nucleotides in length and yet more preferably at least about 1000 nucleotides in length, wherein in this context the term "about" means the referenced nucleotide sequence length plus or minus 10% of that referenced length. It is noted that novel fragments of a PRO polypeptide-encoding nucleotide sequence may be determined in a routine manner by aligning the PRO polypeptide-encoding nucleotide sequence with other known nucleotide sequences using any of a number of well known sequence alignment programs and determining which PRO polypeptide-encoding nucleotide sequence fragment(s) are novel. All of such PRO polypeptide-encoding nucleotide sequences are contemplated herein. Also contemplated are the PRO polypeptide fragments encoded by these nucleotide molecule fragments, preferably those PRO polypeptide fragments that comprise a binding site for an anti-PRO antibody.

In another embodiment, the invention provides isolated PRO polypeptide encoded by any of the isolated nucleic acid sequences hereinabove identified.

In a certain aspect, the invention concerns an isolated PRO polypeptide, comprising an amino acid sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to a PRO polypeptide having a full-length amino acid sequence as disclosed herein, an amino acid sequence lacking the signal peptide as disclosed herein or an extracellular domain of a transmembrane protein, with or without the signal peptide, as disclosed herein.

In a further aspect, the invention concerns an isolated PRO polypeptide comprising an amino acid sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to an amino acid sequence encoded by any of the human protein cDNAs deposited with the ATCC as disclosed herein.

In a further aspect, the invention concerns an isolated PRO polypeptide comprising an amino acid sequence scoring at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives and yet more preferably at least about 99% positives when compared with the amino acid sequence of a PRO polypeptide having a full-length amino acid sequence as disclosed herein, an amino acid sequence lacking the signal peptide as disclosed herein or an extracellular domain of a transmembrane protein, with or without the signal peptide, as disclosed herein.

In a specific aspect, the invention provides an isolated PRO polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

Another aspect the invention provides an isolated PRO polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

In yet another embodiment, the invention concerns agonists and antagonists of a native PRO polypeptide as defined herein. In a particular embodiment, the agonist or antagonist is an anti-PRO antibody or a small molecule.

In a further embodiment, the invention concerns a method of identifying agonists or antagonists to a PRO polypeptide which comprise contacting the PRO polypeptide with a candidate molecule and monitoring a biological activity mediated by said PRO polypeptide. Preferably, the PRO polypeptide is a native PRO polypeptide.

In a still further embodiment, the invention concerns a composition of matter comprising a PRO polypeptide, or an agonist or antagonist of a PRO polypeptide as herein described, or an anti-PRO antibody, in combination with a carrier. Optionally, the carrier is a pharmaceutically acceptable carrier.

Another embodiment of the present invention is directed to the use of a PRO polypeptide, or an agonist or antagonist thereof as hereinbefore described, or an anti-PRO antibody, for the preparation of a medicament useful in the treatment of a condition which is responsive to the PRO polypeptide, an agonist or antagonist thereof or an anti-PRO antibody.

BRIEF DESCRIPTION OF THE DRAWINGS

FIG. 1 shows a nucleotide sequence (SEQ ID NO:1) of a native sequence PRO211 cDNA, wherein SEQ ID NO:1 is a clone designated herein as "DNA32292-1131".

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a native sequence PRO217 cDNA, wherein SEQ ID NO:3 is a clone designated herein as "DNA33094-1131".

FIG. 4 shows the amino acid sequence (SEQ ID NO:4) derived from the coding sequence of SEQ ID NO:3 shown in FIG. 3.

DETAILED DESCRIPTION OF THE PREFERRED EMBODIMENTS

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO polypeptides described herein may be isolated from a variety of sources, such as from human tissue types or from another source, or prepared by recombinant or synthetic methods.

A "native sequence PRO polypeptide" comprises a polypeptide having the same amino acid sequence as the corresponding PRO polypeptide derived from nature. Such native sequence PRO polypeptides can be isolated from nature or can be produced by recombinant or synthetic means. The term "native sequence PRO polypeptide" specifically encompasses naturally-occurring truncated or secreted forms of the specific PRO polypeptide (e.g., an extracellular domain sequence), naturally-occurring variant forms (e.g., alternatively spliced forms) and naturally-occurring allelic variants of the polypeptide. In various embodiments of the invention, the native sequence PRO polypeptides disclosed herein are mature or full-length native sequence polypeptides comprising the full-length amino acids sequences shown in the accompanying figures. Start and stop codons are shown in bold font and underlined in the figures. However, while the PRO polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO polypeptides.

The PRO polypeptide "extracellular domain" or "ECD" refers to a form of the PRO polypeptide which is essentially free of the transmembrane and cytoplasmic domains. Ordinarily, a PRO polypeptide ECD will have less than 1% of such transmembrane and/or cytoplasmic domains and preferably, will have less than 0.5% of such domains. It will be understood that any transmembrane domains identified for the PRO polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO polypeptide may contain from about 5 or fewer amino acids on either side of the transmembrane domain/extracellular domain boundary as identified in the Examples or specification and such polypeptides, with or without the associated signal peptide, and nucleic acid encoding them, are comtemplated by the present invention.

The approximate location of the "signal peptides" of the various PRO polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO polypeptide variant" means an active PRO polypeptide as defined above or below having at least about 80% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Such PRO polypeptide variants include, for instance, PRO polypeptides wherein one or more amino acid residues are added, or deleted, at the N- or C-terminus of the full-length native amino acid sequence. Ordinarily, a PRO polypeptide variant will have at least about 80% amino acid sequence identity, preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and most preferably at least about 99% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other specifically defined fragment of a full-length PRO polypeptide sequence as disclosed herein. Ordinarily, PRO variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, more often at least about 150 amino acids in length, more often at least about 200 amino acids in length, more often at least about 300 amino acids in length, or more.

"Percent (%) amino acid sequence identity" with respect to the PRO polypeptide sequences identified herein is defined as the percentage of amino acid residues in a candidate sequence that are identical with the amino acid residues in the specific PRO polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X," "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the PRO polypeptide of interest having a sequence derived from the native PRO polypeptide and the comparison amino acid sequence of interest (i.e., the sequence against which the PRO polypeptide of interest is being compared which may be a PRO variant polypeptide) as determined by WU-BLAST-2 by (b) the total number of amino acid residues of the PRO polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the PRO polypeptide of interest.

Percent amino acid sequence identity may also be determined using the sequence comparison program NCBI-BLAST2 (Altschul et al., *Nucleic Acids Res.* 25:3389-3402 (1997)). NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO variant polynucleotide" or "PRO variant nucleic acid sequence" means a nucleic acid molecule which encodes an active PRO polypeptide as defined below and which has at least about 80% nucleic acid sequence identity with a nucleotide acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Ordinarily, a PRO variant polynucleotide will have at least about 80% nucleic acid sequence identity, more preferably at least about 81% nucleic acid sequence identity, more preferably at least about 82% nucleic acid sequence identity, more preferably at least about 83% nucleic acid sequence identity, more preferably at least about 84% nucleic acid sequence identity, more preferably at least about 85% nucleic acid sequence identity, more preferably at least about 86% nucleic acid sequence identity, more preferably at least about 87% nucleic acid sequence identity, more preferably at least about 88% nucleic acid sequence identity, more preferably at least about 89% nucleic acid sequence identity, more preferably at least about 90% nucleic acid sequence identity, more preferably at least about 91% nucleic acid sequence identity, more preferably at least about 92% nucleic acid sequence identity, more preferably at least about 93% nucleic acid sequence identity, more preferably at least about 94% nucleic acid sequence identity, more preferably at least about 95% nucleic acid sequence identity, more preferably at least about 96% nucleic acid sequence identity, more preferably at least about 97% nucleic acid sequence identity, more preferably at least about 98% nucleic acid sequence identity and yet more preferably at least about 99% nucleic acid sequence identity with a nucleic acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal sequence, as disclosed herein or any other fragment of a full-length PRO polypeptide sequence as disclosed herein. Variants do not encompass the native nucleotide sequence.

Ordinarily, PRO variant polynucleotides are at least about 30 nucleotides in length, often at least about 60 nucleotides in length, more often at least about 90 nucleotides in length, more often at least about 120 nucleotides in length, more often at least about 150 nucleotides in length, more often at least about 180 nucleotides in length, more often at least about 210 nucleotides in length, more often at least about 240 nucleotides in length, more often at least about 270 nucleotides in length, more often at least about 300 nucleotides in length, more often at least about 450 nucleotides in length, more often at least about 600 nucleotides in length, more often at least about 900 nucleotides in length, or more.

"Percent (%) nucleic acid sequence identity" with respect to PRO-encoding nucleic acid sequences identified herein is defined as the percentage of nucleotides in a candidate sequence that are identical with the nucleotides in the PRO nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the PRO polypeptide-encoding nucleic acid molecule of interest having a sequence derived from the native sequence PRO polypeptide-encoding nucleic acid and the comparison nucleic acid molecule of interest (i.e., the sequence against which the PRO polypeptide-encoding nucleic acid molecule of interest is being compared which may be a variant PRO polynucleotide) as determined by WU-BLAST-2 by (b) the total number of nucleotides of the PRO polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO polypeptide-encoding nucleic acid molecule of interest.

Percent nucleic acid sequence identity may also be determined using the sequence comparison program NCBI-BLAST2 (Altschul et al., *Nucleic Acids Res.* 25:3389-3402 (1997)). NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO variant polynucleotides are nucleic acid molecules that encode an active PRO polypeptide and which are capable of hybridizing, preferably under stringent hybridization and wash conditions, to nucleotide sequences encoding a full-length PRO polypeptide as disclosed herein. PRO variant polypeptides may be those that are encoded by a PRO variant polynucleotide.

The term "positives", in the context of sequence comparison performed as described above, includes residues in the sequences compared that are not identical but have similar properties (e.g. as a result of conservative substitutions, see Table 6 below). For purposes herein, the % value of positives is determined by dividing (a) the number of amino acid residues scoring a positive value between the PRO polypeptide amino acid sequence of interest having a sequence derived from the native PRO polypeptide sequence and the comparison amino acid sequence of interest (i.e., the amino acid sequence against which the PRO polypeptide sequence is being compared) as determined in the BLOSUM62 matrix of WU-BLAST-2 by (b) the total number of amino acid residues of the PRO polypeptide of interest.

Unless specifically stated otherwise, the % value of positives is calculated as described in the immediately preceding paragraph. However, in the context of the amino acid sequence identity comparisons performed as described for ALIGN-2 and NCBI-BLAST-2 above, includes amino acid residues in the sequences compared that are not only identical, but also those that have similar properties. Amino acid residues that score a positive value to an amino acid residue of interest are those that are either identical to the amino acid residue of interest or are a preferred substitution (as defined in Table 6 below) of the amino acid residue of interest.

For amino acid sequence comparisons using ALIGN-2 or NCBI-BLAST2, the % value of positives of a given amino acid sequence A to, with, or against a given amino acid sequence B (which can alternatively be phrased as a given amino acid sequence A that has or comprises a certain % positives to, with, or against a given amino acid sequence B) is calculated as follows:

100 times the fraction X/Y where X is the number of amino acid residues scoring a positive value as defined above by the sequence alignment program ALIGN-2 or NCBI-BLAST2 in that program's alignment of A and B, and where Y is the total number of amino acid residues in B. It will be appreciated that where the length of amino acid sequence A is not equal to the length of amino acid sequence B, the % positives of A to B will not equal the % positives of B to A.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO polypeptide natural environment will not be present. Ordinarily, however, isolated polypeptide will be prepared by at least one purification step.

An "isolated" PRO polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO monoclonal antibodies (including agonist, antagonist, and neutralizing antibodies), anti-PRO antibody compositions with poly-epitopic specificity, single chain anti-PRO antibodies, and fragments of anti-PRO antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a PRO polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of a PRO polypeptide which retain a biological and/or an immunological activity of native or naturally-occurring PRO, wherein "biological" activity refers to a biological function (either inhibitory or stimulatory) caused by a native or naturally-occurring PRO other than the ability to induce the production of an antibody against an antigenic epitope possessed by a native or naturally-occurring PRO and an "immunological" activity refers to the ability to induce the production of an antibody against an antigenic epitope possessed by a native or naturally-occurring PRO.

The term "antagonist" is used in the broadest sense, and includes any molecule that partially or fully blocks, inhibits, or neutralizes a biological activity of a native PRO polypeptide disclosed herein. In a similar manner, the term "agonist" is used in the broadest sense and includes any molecule that mimics a biological activity of a native PRO polypeptide disclosed herein. Suitable agonist or antagonist molecules specifically include agonist or antagonist antibodies or antibody fragments, fragments or amino acid sequence variants of native PRO polypeptides, peptides, antisense oligonucleotides, small organic molecules, etc. Methods for identifying agonists or antagonists of a PRO polypeptide may comprise contacting a PRO polypeptide with a candidate agonist or antagonist molecule and measuring a detectable change in one or more biological activities normally associated with the PRO polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

Table 1

```
/*
 *
 * C-C increased from 12 to 15
 * Z is average of EQ
 * B is average of ND
 * match with stop is _M; stop-stop = 0; J (joker) match = 0
 */
define  _M    -8    /* value of a match with a stop */ int      _day[26][26] = {
/*       A  B  C  D  E  F  G  H  I  J  K  L  M  N  O  P  Q  R  S  T  U  V  W  X  Y  Z */
/* A */ { 2, 0,-2, 0, 0,-4, 1,-1,-1, 0,-1,-2,-1, 0,_M, 1, 0,-2, 1, 1, 0, 0,-6, 0,-3, 0},
/* B */ { 0, 3,-4, 3, 2,-5, 0, 1,-2, 0, 0,-3,-2, 2,_M,-1, 1, 0, 0, 0, 0,-2,-5, 0,-3, 1},
/* C */ {-2,-4,15,-5,-5,-4,-3,-3,-2, 0,-5,-6,-5,-4,_M,-3,-5,-4, 0,-2, 0,-2,-8, 0, 0,-5},
/* D */ { 0, 3,-5, 4, 3,-6, 1, 1,-2, 0, 0,-4,-3, 2,_M,-1, 2,-1, 0, 0, 0,-2,-7, 0,-4, 2},
/* E */ { 0, 2,-5, 3, 4,-5, 0, 1,-2, 0, 0,-3,-2, 1,_M,-1, 2,-1, 0, 0, 0,-2,-7, 0,-4, 3},
/* F */ {-4,-5,-4,-6,-5, 9,-5,-2, 1, 0,-5, 2, 0,-4,_M,-5,-5,-4,-3,-3, 0,-1, 0, 0, 7,-5},
/* G */ { 1, 0,-3, 1, 0,-5, 5,-2,-3, 0,-2,-4,-3, 0,_M,-1,-1,-3, 1, 0, 0, 0,-1,-7, 0,-5, 0},
/* H */ {-1, 1,-3, 1, 1,-2,-2, 6,-2, 0, 0,-2,-2, 2,_M, 0, 3, 2,-1,-1, 0,-2,-3, 0, 0, 2},
/* I */ {-1,-2,-2,-2,-2, 1,-3,-2, 5, 0,-2, 2, 2,-2,_M,-2,-2,-2,-1, 0, 0, 4,-5, 0,-1,-2},
/* J */ { 0, 0, 0, 0, 0, 0, 0, 0, 0, 0, 0, 0, 0, 0,_M, 0, 0, 0, 0, 0, 0, 0, 0, 0, 0, 0},
/* K */ {-1, 0,-5, 0, 0,-5,-2, 0,-2, 0, 5,-3, 0, 1,_M,-1, 1, 3, 0, 0, 0,-2,-3, 0,-4, 0},
/* L */ {-2,-3,-6,-4,-3, 2,-4,-2, 2, 0,-3, 6, 4,-3,_M,-3,-2,-3,-3,-1, 0, 2,-2, 0,-1,-2},
/* M */ {-1,-2,-5,-3,-2, 0,-3,-2, 2, 0, 0, 4, 6,-2,_M,-2,-1, 0,-2,-1, 0, 2,-4, 0,-2,-1},
/* N */ { 0, 2,-4, 2, 1,-4, 0, 2,-2, 0, 1,-3,-2, 2,_M,-1, 1, 0, 1, 0, 0,-2,-4, 0,-2, 1},
/* O */ {_M,_M,_M,_M,_M,_M,_M,_M,_M,_M,_M,_M,_M,_M, 0,_M,_M,_M,_M,_M,_M,_M,_M,_M,_M,_M},
/* P */ { 1,-1,-3,-1,-1,-5,-1, 0,-2, 0,-1,-3,-2,-1,_M, 6, 0, 0, 1, 0, 0,-1,-6, 0,-5, 0},
/* Q */ { 0, 1,-5, 2, 2,-5,-1, 3,-2, 0, 1,-2,-1, 1,_M, 0, 4, 1,-1,-1, 0,-2,-5, 0,-4, 3},
/* R */ {-2, 0,-4,-1,-1,-4,-3, 2,-2, 0, 3,-3, 0, 0,_M, 0, 1, 6, 0,-1, 0,-2, 2, 0,-4, 0},
/* S */ { 1, 0, 0, 0, 0,-3, 1,-1,-1, 0, 0,-3,-2, 1,_M, 1,-1, 0, 2, 1, 0,-1,-2, 0,-3, 0},
/* T */ { 1, 0,-2, 0, 0,-3, 0,-1, 0, 0, 0,-1,-1, 0,_M, 0,-1,-1, 1, 3, 0, 0,-5, 0,-3, 0},
/* U */ { 0, 0, 0, 0, 0, 0, 0, 0, 0, 0, 0, 0, 0, 0,_M, 0, 0, 0, 0, 0, 0, 0, 0, 0, 0, 0},
/* V */ { 0,-2,-2,-2,-2,-1,-1,-2, 4, 0,-2, 2, 2,-2,_M,-1,-2,-2,-1, 0, 0, 4,-6, 0,-2,-2},
/* W */ {-6,-5,-8,-7,-7, 0,-7,-3,-5, 0,-3,-2,-4,-4,_M,-6,-5, 2,-2,-5, 0,-6,17, 0, 0,-6},
/* X */ { 0, 0, 0, 0, 0, 0, 0, 0, 0, 0, 0, 0, 0, 0,_M, 0, 0, 0, 0, 0, 0, 0, 0, 0, 0, 0},
/* Y */ {-3,-3, 0,-4,-4, 7,-5, 0,-1, 0,-4,-1,-2,-2,_M,-5,-4,-4,-3,-3, 0,-2, 0, 0,10,-4},
/* Z */ { 0, 1,-5, 2, 3,-5, 0, 2,-2, 0, 0,-2,-1, 1,_M, 0, 3, 0, 0, 0, 0,-2,-6, 0,-4, 4}
};
```

Table 1 (cont')

```
/*
*/
#include <stdio.h>
include <ctype.h> define  MAXJMP   16      /* max jumps in a diag */
define  MAXGAP   24      /* don't continue to penalize gaps larger than this */
#define  JMPS     1024    /* max jmps in an path */
define  MX       4       /* save if there's at least MX-1 bases since last jmp */ define  DMAT     3       /* value of matching bases */
define  DMIS     0       /* penalty for mismatched bases */
#define  DINS0    8       /* penalty for a gap */
#define  DINS1    1       /* penalty per base */
#define  PINS0    8       /* penalty for a gap */
define  PINS1    4       /* penalty per residue */ struct jmp {
        short           n[MAXJMP];      /* size of jmp (neg for dely) */
        unsigned short  x[MAXJMP];      /* base no. of jmp in seq x */
};                                      /* limits seq to 2^16 -1 */ struct diag {
        int             score;          /* score at last jmp */
        long            offset;         /* offset of prev block */
        short           ijmp;           /* current jmp index */
        struct jmp      jp;             /* list of jmps */
};

struct path {
        int             spc;            /* number of leading spaces */
        short           n[JMPS];        /* size of jmp (gap) */
        int             x[JMPS];        /* loc of jmp (last elem before gap) */
};

char            *ofile;                 /* output file name */
char            *namex[2];              /* seq names: getseqs() */
char            *prog;                  /* prog name for err msgs */
char            *seqx[2];               /* seqs: getseqs() */
int             dmax;                   /* best diag: nw() */
int             dmax0;                  /* final diag */
int             dna;                    /* set if dna: main() */
int             endgaps;                /* set if penalizing end gaps */
int             gapx, gapy;             /* total gaps in seqs */
int             len0, len1;             /* seq lens */
int             ngapx, ngapy;           /* total size of gaps */
int             smax;                   /* max score: nw() */
int             *xbm;                   /* bitmap for matching */
long            offset;                 /* current offset in jmp file */
struct  diag    *dx;                    /* holds diagonals */
struct  path    pp[2];                  /* holds path for seqs */ char            *calloc(), *malloc(), *index(), *strcpy();
char            *getseq(), *g_calloc();
```

Table 1 (cont')

```
/* Needleman-Wunsch alignment program
*
* usage: progs file1 file2
* where file1 and file2 are two dna or two protein sequences.
* The sequences can be in upper- or lower-case an may contain ambiguity
* Any lines beginning with ';', '>' or '<' are ignored
* Max file length is 65535 (limited by unsigned short x in the jmp struct)
* A sequence with 1/3 or more of its elements ACGTU is assumed to be DNA
* Output is in the file "align.out"
*
* The program may create a tmp file in /tmp to hold info about traceback.
* Original version developed under BSD 4.3 on a vax 8650
*/
include "nw.h"
#include "day.h"

static    _dbval[26] = {
          1,14,2,13,0,0,4,11,0,0,12,0,3,15,0,0,0,5,6,8,8,7,9,0,10,0
};

static    _pbval[26] = {
          1, 2|(1<<('D'-'A'))|(1<<('N'-'A')), 4, 8, 16, 32, 64,
          128, 256, 0xFFFFFFF, 1<<10, 1<<11, 1<<12, 1<<13, 1<<14,
          1<<15, 1<<16, 1<<17, 1<<18, 1<<19, 1<<20, 1<<21, 1<<22,
          1<<23, 1<<24, 1<<25|(1<<('E'-'A'))|(1<<('Q'-'A'))
};

main(ac, av)                                                                    main
          int       ac;
          char      *av[];
{
          prog = av[0];
          if (ac != 3) {
                    fprintf(stderr,"usage: %s file1 file2\n", prog);
                    fprintf(stderr,"where file1 and file2 are two dna or two protein sequences.\n");
                    fprintf(stderr,"The sequences can be in upper- or lower-case\n");
                    fprintf(stderr,"Any lines beginning with ';' or '<' are ignored\n");
                    fprintf(stderr,"Output is in the file \"align.out\"\n");
                    exit(1);
          }
          namex[0] = av[1];
          namex[1] = av[2];
          seqx[0] = getseq(namex[0], &len0);
          seqx[1] = getseq(namex[1], &len1);
          xbm = (dna)? _dbval : _pbval;

endgaps = 0;              /* 1 to penalize endgaps */
          ofile = "align.out";      /* output file */ nw();         /* fill in the matrix, get the possible jmps */
          readjmps();   /* get the actual jmps */
          print();      /* print stats, alignment */ cleanup(0);   /* unlink any tmp files */
}
```

Table 1 (cont')

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()
{
        char        *px, *py;        /* seqs and ptrs */
        int         *ndely, *dely;   /* keep track of dely */
        int         ndelx, delx;     /* keep track of delx */
        int         *tmp;            /* for swapping row0, row1 */
        int         mis;             /* score for each type */
        int         ins0, ins1;      /* insertion penalties */
        register    id;              /* diagonal index */
        register    ij;              /* jmp index */
        register    *col0, *col1;    /* score for curr, last row */
        register    xx, yy;          /* index into seqs */ dx = (struct diag *)g_calloc("to get diags", len0+len1+1, sizeof(struct diag));

ndely = (int *)g_calloc("to get ndely", len1+1, sizeof(int));
        dely  = (int *)g_calloc("to get dely", len1+1, sizeof(int));
        col0  = (int *)g_calloc("to get col0", len1+1, sizeof(int));
        col1  = (int *)g_calloc("to get col1", len1+1, sizeof(int));
        ins0  = (dna)? DINS0 : PINS0;
        ins1  = (dna)? DINS1 : PINS1;

smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;        /* Waterman Bull Math Biol 84 */
        }
        else
                for (yy = 1; yy <= len1; yy++)
                        dely[yy] = -ins0;

/* fill in match matrix
        */
        for (px = seqx[0], xx = 1; xx <= len0; px++, xx++) {
                /* initialize first entry in col
                */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

Table 1 (cont')

...nw

```
for (py = seqx[1], yy = 1; yy <= len1; py++, yy++) {
        mis = col0[yy-1];
    if (dna)
                mis += (xbm[*px-'A']&xbm[*py-'A'])? DMAT : DMIS;
    else
                mis += _day[*px-'A'][*py-'A'];

/* update penalty for del in x seq;
     * favor new del over ongong del
     * ignore MAXGAP if weighting endgaps
     */
    if (endgaps || ndely[yy] < MAXGAP) {
            if (col0[yy] - ins0 >= dely[yy]) {
                    dely[yy] = col0[yy] - (ins0+ins1);
                    ndely[yy] = 1;
            } else {
                    dely[yy] -= ins1;
                    ndely[yy]++;
            }
    } else {
            if (col0[yy] - (ins0+ins1) >= dely[yy]) {
                    dely[yy] = col0[yy] - (ins0+ins1);
                    ndely[yy] = 1;
            } else
                    ndely[yy]++;
    }

/* update penalty for del in y seq;
     * favor new del over ongong del
     */
    if (endgaps || ndelx < MAXGAP) {
            if (col1[yy-1] - ins0 >= delx) {
                    delx = col1[yy-1] - (ins0+ins1);
                    ndelx = 1;
            } else {
                    delx -= ins1;
                    ndelx++;
            }
    } else {
            if (col1[yy-1] - (ins0+ins1) >= delx) {
                    delx = col1[yy-1] - (ins0+ins1);
                    ndelx = 1;
            } else
                    ndelx++;
    }

/* pick the maximum score; we're favoring
     * mis over any del and delx over dely
     */
```

Table 1 (cont')

```
                      id = xx - yy + len1 - 1;
                      if (mis >= delx && mis >= dely[yy])
                                 col1[yy] = mis;
                      else if (delx >= dely[yy]) {
                                 col1[yy] = delx;
                                 ij = dx[id].ijmp;
                                 if (dx[id].jp.n[0] && (!dna || (ndelx >= MAXJMP
                                 && xx > dx[id].jp.x[ij]+MX) || mis > dx[id].score+DINS0)) {
                                            dx[id].ijmp++;
                                            if (++ij >= MAXJMP) {
                                                       writejmps(id);
                                                       ij = dx[id].ijmp = 0;
                                                       dx[id].offset = offset;
                                                       offset += sizeof(struct jmp) + sizeof(offset);
                                            }
                                 }
                                 dx[id].jp.n[ij] = ndelx;
                                 dx[id].jp.x[ij] = xx;
                                 dx[id].score = delx;
                      }
                      else {
                                 col1[yy] = dely[yy];
                                 ij = dx[id].ijmp;
                      if (dx[id].jp.n[0] && (!dna || (ndely[yy] >= MAXJMP
                                 && xx > dx[id].jp.x[ij]+MX) || mis > dx[id].score+DINS0)) {
                                            dx[id].ijmp++;
                                            if (++ij >= MAXJMP) {
                                                       writejmps(id);
                                                       ij = dx[id].ijmp = 0;
                                                       dx[id].offset = offset;
                                                       offset += sizeof(struct jmp) + sizeof(offset);
                                            }
                                 }
                                 dx[id].jp.n[ij] = -ndely[yy];
                                 dx[id].jp.x[ij] = xx;
                                 dx[id].score = dely[yy];
                      }
                      if (xx == len0 && yy < len1) {
                                 /* last col
                                 */
                                 if (endgaps)
                                            col1[yy] -= ins0+ins1*(len1-yy);
                                 if (col1[yy] > smax) {
                                            smax = col1[yy];
                                            dmax = id;
                                 }
                      }
            }
            if (endgaps && xx < len0)
                      col1[yy-1] -= ins0+ins1*(len0-xx);
            if (col1[yy-1] > smax) {
                      smax = col1[yy-1];
                      dmax = id;
            }
            tmp = col0; col0 = col1; col1 = tmp;
 }
 (void) free((char *)ndely);
 (void) free((char *)dely);
 (void) free((char *)col0);
 (void) free((char *)col1);
}
```

Table 1 (cont')

```c
/*
*
* print() -- only routine visible outside this module
*
* static:
* getmat() -- trace back best path, count matches: print()
* pr_align() -- print alignment of described in array p[]: print()
* dumpblock() -- dump a block of lines with numbers, stars: pr_align()
* nums() -- put out a number line: dumpblock()
* putline() -- put out a line (name, [num], seq, [num]): dumpblock()
* stars() - -put a line of stars: dumpblock()
* stripname() -- strip any path and prefix from a seqname
*/ include "nw.h"

define SPC      3
#define P_LINE   256    /* maximum output line */
define P_SPC    3      /* space between name or num and seq */ extern   _day[26][26];
int      olen;          /* set output line length */
FILE     *fx;           /* output file */ print()
{
        int    lx, ly, firstgap, lastgap;    /* overlap */ if ((fx = fopen(ofile, "w")) == 0) {
                fprintf(stderr,"%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) {          /* leading gap in x */
                pp[0].spc = firstgap = len1 - dmax - 1;
                ly -= pp[0].spc;
        }
        else if (dmax > len1 - 1) {     /* leading gap in y */
                pp[1].spc = firstgap = dmax - (len1 - 1);
                lx -= pp[1].spc;
        }
        if (dmax0 < len0 - 1) {         /* trailing gap in x */
                lastgap = len0 - dmax0 -1;
                lx -= lastgap;
        }
        else if (dmax0 > len0 - 1) {    /* trailing gap in y */
                lastgap = dmax0 - (len0 - 1);
                ly -= lastgap;
        }
        getmat(lx, ly, firstgap, lastgap);
        pr_align();
}
``` print

Table 1 (cont')

```
/*
 * trace back the best path, count matches
 */
static
getmat(lx, ly, firstgap, lastgap)                                           getmat
        int     lx, ly;                 /* "core" (minus endgaps) */
        int     firstgap, lastgap;      /* leading trailing overlap */
{
        int             nm, i0, i1, siz0, siz1;
        char            outx[32];
        double          pct;
        register        n0, n1;
        register char   *p0, *p1;

/* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;

nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

/* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
```

Table 1 (cont')

```
                fprintf(fx, "<gaps in first sequence: %d", gapx);                                              ...getmat
                if (gapx) {
                        (void) sprintf(outx, " (%d %s%s)",
                                ngapx, (dna)? "base":"residue", (ngapx == 1)? "":"s");
                        fprintf(fx,"%s", outx);

fprintf(fx, ", gaps in second sequence: %d", gapy);
                if (gapy) {
                        (void) sprintf(outx, " (%d %s%s)",
                                ngapy, (dna)? "base":"residue", (ngapy == 1)? "":"s");
                        fprintf(fx,"%s", outx);
                }
                if (dna)
                        fprintf(fx,
                        "\n<score: %d (match = %d, mismatch = %d, gap penalty = %d + %d per base)\n",
                                smax, DMAT, DMIS, DINS0, DINS1);
                else
                        fprintf(fx,
                        "\n<score: %d (Dayhoff PAM 250 matrix, gap penalty = %d + %d per residue)\n",
                                smax, PINS0, PINS1);
                if (endgaps)
                        fprintf(fx,
                        "<endgaps penalized. left endgap: %d %s%s, right endgap: %d %s%s\n",
                                firstgap, (dna)? "base" : "residue", (firstgap == 1)? "" : "s",
                                lastgap, (dna)? "base" : "residue", (lastgap == 1)? "" : "s");
                else
                        fprintf(fx, "<endgaps not penalized\n");
} static          nm;              /* matches in core -- for checking */
static          lmax;            /* lengths of stripped file names */
static          ij[2];           /* jmp index for a path */
static          nc[2];           /* number at start of current line */
static          ni[2];           /* current elem number -- for gapping */
static          siz[2];
static char     *ps[2];          /* ptr to current element */
static char     *po[2];          /* ptr to next output char slot */
static char     out[2][P_LINE];  /* output line */
static char     star[P_LINE];    /* set by stars() */

/*
* print alignment of described in struct path pp[]
*/
static
pr_align()                                                                                                    pr_align
{
        int             nn;      /* char count */
        int             more;
        register        i;

for (i = 0, lmax = 0; i < 2; i++) {
                nn = stripname(namex[i]);
                if (nn > lmax)
                        lmax = nn;

nc[i] = 1;
                ni[i] = 1;
                siz[i] = ij[i] = 0;
                ps[i] = seqx[i];
                po[i] = out[i];
        }
```

Table 1 (cont')

```
for (nn = nm = 0, more = 1; more; ) {                                                          ...pr_align
        for (i = more = 0; i < 2; i++) {
                /*
                 * do we have more of this sequence?
                 */
                if (!*ps[i])
                        continue;

more++;

if (pp[i].spc) {        /* leading space */
                        *po[i]++ = ' ';
                        pp[i].spc--;
                }
                else if (siz[i]) {      /* in a gap */
                        *po[i]++ = '-';
                        siz[i]--;
                }
                else {                  /* we're putting a seq element
                                         */
                        *po[i] = *ps[i];
                        if (islower(*ps[i]))
                                *ps[i] = toupper(*ps[i]);
                        po[i]++;
                        ps[i]++;

/*
                         * are we at next gap for this seq?
                         */
                        if (ni[i] == pp[i].x[ij[i]]) {
                                /*
                                 * we need to merge all gaps
                                 * at this location
                                 */
                                siz[i] = pp[i].n[ij[i]++];
                                while (ni[i] == pp[i].x[ij[i]])
                                        siz[i] += pp[i].n[ij[i]++];
                        }
                        ni[i]++;
                }
        }
        if (++nn == olen || !more && nn) {
                dumpblock();
                for (i = 0; i < 2; i++)
                        po[i] = out[i];
                nn = 0;
        }
    }
}
/*
 * dump a block of lines, including numbers, stars: pr_align()
 */
static
dumpblock()                                                                                    dumpblock
{
        register i;

for (i = 0; i < 2; i++)
                *po[i]-- = '\0';
```

Table 1 (cont')

...dumpblock

```
            (void) putc('\n', fx);
            for (i = 0; i < 2; i++) {
                    if (*out[i] && (*out[i] != ' ' || *(po[i]) != ' ')) {
                            if (i == 0)
                                    nums(i);
                            if (i == 0 && *out[1])
                                    stars();
                            putline(i);
                            if (i == 0 && *out[1])
                                    fprintf(fx, star);
                            if (i == 1)
                                    nums(i);
                    }
            }
}
/*
 * put out a number line: dumpblock()
 */
static
nums(ix)
        int      ix;       /* index in out[] holding seq line */
{
        char        nline[P_LINE];
        register    i, j;
        register char  *pn, *px, *py;

for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}
/*
 * put out a line (name, [num], seq, [num]): dumpblock()
 */
static
putline(ix)
        int      ix;
{
``` nums putline

Table 1 (cont')

...putline

```
        int             i;
        register char   *px;

for (px = namex[ix], i = 0; *px && *px != ':'; px++, i++)
                (void) putc(*px, fx);
        for (; i < lmax+P_SPC; i++)
                (void) putc(' ', fx);

/* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}
/*
 * put a line of stars (seqs always in out[0], out[1]): dumpblock()
 */
static
stars()
{
        int             i;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) { if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
``` stars

Table 1 (cont')

```
/*
 * strip path or prefix from pn, return len: pr_align()
 */
static
stripname(pn)
        char    *pn;    /* file name (may be path) */
{
        register char   *px, *py;

py = 0;
        for (px = pn; *px; px++)
                if (*px == '/')
                        py = px + 1;
        if (py)
                (void) strcpy(pn, py);
        return(strlen(pn));

}
``` stripname

Table 1 (cont')

```
/*
* cleanup() -- cleanup any tmp file
* getseq() -- read in seq, set dna, len, maxlen
* g_calloc() -- calloc() with error checkin
* readjmps() -- get the good jmps, from tmp file if necessary
* writejmps() -- write a filled array of jmps to a tmp file: nw()
*/
include "nw.h"
include <sys/file.h> char    *jname = "/tmp/homgXXXXXX";         /* tmp file for jmps */
FILE    *fj;

int     cleanup();                           /* cleanup tmp file */
long    lseek();

/*
* remove any tmp file if we blow
*/
cleanup(i)
        int     i;
{
        if (fj)
                (void) unlink(jname);
        exit(i);
}

/*
* read, return ptr to seq, set dna, len, maxlen
* skip lines starting with ';', '<', or '>'
* seq in upper or lower case
*/
char    *
getseq(file, len)
        char    *file;                       /* file name */
        int     *len;                        /* seq len */
{
        char            line[1024], *pseq;
        register char   *px, *py;
        int             natgc, tlen;
        FILE            *fp;

if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6, file);
                exit(1);
        }
        pseq[0] = pseq[1] = pseq[2] = pseq[3] = '\0';
``` cleanup getseq

Table 1 (cont')

...getseq

```
            py = pseq + 4;
            *len = tlen;
            rewind(fp);

while (fgets(line, 1024, fp)) {
                    if (*line == ';' || *line == '<' || *line == '>')
                            continue;
                    for (px = line; *px != '\n'; px++) {
                            if (isupper(*px))
                                    *py++ = *px;
                            else if (islower(*px))
                                    *py++ = toupper(*px);
                            if (index("ATGCU",*(py-1)))
                                    natgc++;
                    }
            }
            *py++ = '\0';
            *py = '\0';
            (void) fclose(fp);
            dna = natgc > (tlen/3);
            return(pseq+4);
    } char    *
    g_calloc(msg, nx, sz)                                                                           g_calloc
            char    *msg;           /* program, calling routine */
            int     nx, sz;         /* number and size of elements */
    {
            char            *px, *calloc();

if ((px = calloc((unsigned)nx, (unsigned)sz)) == 0) {
                    if (*msg) {
                            fprintf(stderr, "%s: g_calloc() failed %s (n=%d, sz=%d)\n", prog, msg, nx, sz);
                            exit(1);
                    }
            }
            return(px);
    }
    /*
    *   get final jmps from dx[] or tmp file, set pp[], reset dmax: main()
    */
    readjmps()                                                                                      readjmps
    {
            int             fd = -1;
            int             siz, i0, i1;
            register i, j, xx;

if (fj) {
                    (void) fclose(fj);
                    if ((fd = open(jname, O_RDONLY, 0)) < 0) {
                            fprintf(stderr, "%s: can't open() %s\n", prog, jname);
                            cleanup(1);
                    }
            }
            for (i = i0 = i1 = 0, dmax0 = dmax, xx = len0; ; i++) {
                    while (1) {
                            for (j = dx[dmax].ijmp; j >= 0 && dx[dmax].jp.x[j] >= xx; j--)
                                    ;
```

Table 1 (cont')

...readjmps

```
                    if (j < 0 && dx[dmax].offset && fj) {
                            (void) lseek(fd, dx[dmax].offset, 0);
                            (void) read(fd, (char *)&dx[dmax].jp, sizeof(struct jmp));
                            (void) read(fd, (char *)&dx[dmax].offset, sizeof(dx[dmax].offset));
                            dx[dmax].ijmp = MAXJMP-1;
                    }
                    else
                            break;
            }
            if (i >= JMPS) {
                    fprintf(stderr, "%s: too many gaps in alignment\n", prog);
                    cleanup(1);
            }
            if (j >= 0) {
                    siz = dx[dmax].jp.n[j];
                    xx = dx[dmax].jp.x[j];
                    dmax += siz;
                    if (siz < 0) {                      /* gap in second seq */
                            pp[1].n[i1] = -siz;
                            xx += siz;
                            /* id = xx - yy + len1 - 1
                             */
                            pp[1].x[i1] = xx - dmax + len1 - 1;
                            gapy++;
                            ngapy -= siz;
/* ignore MAXGAP when doing endgaps */
                            siz = (-siz < MAXGAP || endgaps)? -siz : MAXGAP;
                            i1++;
                    }
                    else if (siz > 0) {                 /* gap in first seq */
                            pp[0].n[i0] = siz;
                            pp[0].x[i0] = xx;
                            gapx++;
                            ngapx += siz;
/* ignore MAXGAP when doing endgaps */
                            siz = (siz < MAXGAP || endgaps)? siz : MAXGAP;
                            i0++;
                    }
            }
            else
                    break;
    }
    /* reverse the order of jmps
     */
    for (j = 0, i0--; j < i0; j++, i0--) {
            i = pp[0].n[j]; pp[0].n[j] = pp[0].n[i0]; pp[0].n[i0] = i;
            i = pp[0].x[j]; pp[0].x[j] = pp[0].x[i0]; pp[0].x[i0] = i;
    }
    for (j = 0, i1--; j < i1; j++, i1--) {
            i = pp[1].n[j]; pp[1].n[j] = pp[1].n[i1]; pp[1].n[i1] = i;
            i = pp[1].x[j]; pp[1].x[j] = pp[1].x[i1]; pp[1].x[i1] = i;
    }
    if (fd >= 0)
            (void) close(fd);
    if (fj) {
            (void) unlink(jname);
            fj = 0;
            offset = 0;
    }
}
```

Table 1 (cont')

```
/*
 * write a filled jmp struct offset of the prev one (if any): nw()
 */
writejmps(ix)                                                                    writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| PRO | XXXXXXXXXXXXXXX | (Length = 15 amino acids) |
|---|---|---|
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| PRO | XXXXXXXXXX | (Length = 10 amino acids) |
|---|---|---|
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| PRO-DNA | NNNNNNNNNNNNNN | (Length = 14 nucleotides) |
|---|---|---|
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| PRO-DNA | NNNNNNNNNNNN | (Length = 12 nucleotides) |
|---|---|---|
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-Length PRO Polypeptides

The present invention provides newly identified and isolated nucleotide sequences encoding polypeptides referred to in the present application as PRO polypeptides. In particular, cDNAs encoding various PRO polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO polypeptides and encoding nucleic acids described herein, Applicants have identified what is believed to be the reading frame best identifiable with the sequence information available at the time.

Full-length PRO211 and PRO217 Polypeptides

The present invention provides newly identified and isolated nucleotide sequences encoding polypeptides referred to in the present application as PRO211 and PRO217. In particular, Applicants have identified and isolated cDNA encoding PRO211 and PRO217 polypeptides, as disclosed in further detail in the Examples below. Using BLAST (FastA format) sequence alignment computer programs, Applicants found that cDNA sequences encoding full-length native sequence PRO211 and PRO217 have homologies to known proteins having EGF-like domains. Specifically, the cDNA sequence DNA32292-1131 (FIG. 1, SEQ ID NO:1) has certain identify and a Blast score of 209 with PAC6_RAT and certain identify and a Blast score of 206 with Fibulin-1, isoform c precursor. The cDNA sequence DNA33094-1131 (FIG. 3, SEQ ID NO:3) has 36% identity and a Blast score of 336 with eastern newt tenascin, and 37% identity and a Blast score of 331 with human tenascin-X precursor. Accordingly, it is presently believed that PRO211 and PRO217 polypeptides disclosed in the present application are newly identified members of the EGF-like family and possesses properties typical of the EGF-like protein family.

B. PRO Polypeptide Variants

In addition to the full-length native sequence PRO polypeptides described herein, it is contemplated that PRO variants can be prepared. PRO variants can be prepared by introducing appropriate nucleotide changes into the PRO DNA, and/or by synthesis of the desired PRO polypeptide. Those skilled in the art will appreciate that amino acid changes may alter post-translational processes of the PRO, such as changing the number or position of glycosylation sites or altering the membrane anchoring characteristics.

Variations in the native full-length sequence PRO or in various domains of the PRO described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO that results in a change in the amino acid sequence of the PRO as compared with the native sequence PRO. Optionally the variation is by substitution of at least one amino acid with any other amino acid in one or more of the domains of the PRO. Guidance in determining which amino acid residue may be inserted, substituted or deleted without adversely affecting the desired activity may be found by comparing the sequence of the PRO with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO polypeptide.

PRO fragments may be prepared by any of a number of conventional techniques. Desired peptide fragments may be chemically synthesized. An alternative approach involves generating PRO fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO polypeptide fragments share at least one biological and/or immunological activity with the native PRO polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the PRO variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

C. Modifications of PRO

Covalent modifications of PRO are included within the scope of this invention. One type of covalent modification includes reacting targeted amino acid residues of a PRO polypeptide with an organic derivatizing agent that is capable of reacting with selected side chains or the N- or C-terminal residues of the PRO. Derivatization with bifunctional agents is useful, for instance, for crosslinking PRO to a water-insoluble support matrix or surface for use in the method for purifying anti-PRO antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W. H. Freeman & Co., San Francisco, pp. 79-86 (1983)], acetylation of the N-terminal amine, and amidation of any C-terminal carboxyl group.

Another type of covalent modification of the PRO polypeptide included within the scope of this invention comprises altering the native glycosylation pattern of the polypeptide. "Altering the native glycosylation pattern" is intended for purposes herein to mean deleting one or more carbohydrate moieties found in native sequence PRO (either by removing the underlying glycosylation site or by deleting the glycosylation by chemical and/or enzymatic means), and/or adding one or more glycosylation sites that are not present in the native sequence PRO. In addition, the phrase includes qualitative changes in the glycosylation of the native proteins, involving a change in the nature and proportions of the various carbohydrate moieties present.

Addition of glycosylation sites to the PRO polypeptide may be accomplished by altering the amino acid sequence. The alteration may be made, for example, by the addition of, or substitution by, one or more serine or threonine residues to the native sequence PRO (for O-linked glycosylation sites). The PRO amino acid sequence may optionally be altered through changes at the DNA level, particularly by mutating the DNA encoding the PRO polypeptide at preselected bases such that codons are generated that will translate into the desired amino acids.

Another means of increasing the number of carbohydrate moieties on the PRO polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the PRO polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO comprises linking the PRO polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO of the present invention may also be modified in a way to form a chimeric molecule comprising PRO fused to another, heterologous polypeptide or amino acid sequence.

In one embodiment, such a chimeric molecule comprises a fusion of the PRO with a tag polypeptide which provides an epitope to which an anti-tag antibody can selectively bind. The epitope tag is generally placed at the amino- or carboxyl-terminus of the PRO. The presence of such epitope-tagged forms of the PRO can be detected using an antibody against the tag polypeptide. Also, provision of the epitope tag enables the PRO to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the PRO with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO

The description below relates primarily to production of PRO by culturing cells transformed or transfected with a vector containing PRO nucleic acid. It is, of course, contemplated that alternative methods, which are well known in the art, may be employed to prepare PRO. For instance, the PRO sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO may be chemically synthesized separately and combined using chemical or enzymatic methods to produce the full-length PRO.

1. Isolation of DNA Encoding PRO

DNA encoding PRO may be obtained from a cDNA library prepared from tissue believed to possess the PRO mRNA and to express it at a detectable level. Accordingly, human PRO DNA can be conveniently obtained from a cDNA library prepared from human tissue, such as described in the Examples. The PRO-encoding gene may also be obtained from a genomic library or by known synthetic procedures (e.g., automated nucleic acid synthesis).

Libraries can be screened with probes (such as antibodies to the PRO or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac) 169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 737 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus; yarrowia* (EP 402,226); *Pichia pastoris* (EP 183,070; Sreekrishna et al., *J. Basic Microbiol.*, 28:265-278 [1988]); *Candida; Trichoderma reesia* (EP 244, 234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated PRO are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CVI line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the C. albicans glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO-encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trp1 gene present in the yeast plasmid YRp7 [Stinchcomb et al.,. Nature, 282:39 (1979); Kingsman et al., Gene, 7:141 (1979); Tschemper et al., Gene, 10:157 (1980)]. The trp1 gene provides a selection marker for a mutant strain of yeast lacking the ability to grow in tryptophan, for example, ATCC No. 44076 or PEP4-1 [Jones, Genetics, 85:12 (1977)].

Expression and cloning vectors usually contain a promoter operably linked to the PRO-encoding nucleic acid sequence to direct mRNA synthesis. Promoters recognized by a variety of potential host cells are well known. Promoters suitable for use with prokaryotic hosts include the β-lactamase and lactose promoter systems [Chang et al., Nature, 275:615 (1978); Goeddel et al., Nature, 281:544 (1979)], alkaline phosphatase, a tryptophan (trp) promoter system [Goeddel, Nucleic Acids Res., 8:4057 (1980); EP 36,776], and hybrid promoters such as the tac promoter [deBoer et al., Proc. Natl. Acad. Sci. USA, 80:21-25 (1983)]. Promoters for use in bacterial systems also will contain a Shine-Dalgarno (S.D.) sequence operably linked to the DNA encoding PRO.

Examples of suitable promoting sequences for use with yeast hosts include the promoters for 3-phosphoglycerate kinase [Hitzeman et al., J. Biol. Chem., 255:2073 (1980)] or other glycolytic enzymes [Hess et al., J. Adv. Enzyme Reg., 7:149 (1968); Holland, Biochemistry, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO.

Still other methods, vectors, and host cells suitable for adaptation to the synthesis of PRO in recombinant vertebrate cell culture are described in Gething et al., Nature, 293:620-625 (1981); Mantei et al., Nature, 281:40-46(1979); EP 117, 060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, Proc. Natl. Acad. Sci. USA, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO polypeptide or against a synthetic peptide based on the DNA sequences provided herein or against exogenous sequence fused to PRO DNA and encoding a specific antibody epitope.

5. Purification of Polypeptide

Forms of PRO may be recovered from culture medium or from host cell lysates. If membrane-bound, it can be released from the membrane using a suitable detergent solution (e.g. Triton-X 100) or by enzymatic cleavage. Cells employed in expression of PRO can be disrupted by various physical or chemical means, such as freeze-thaw cycling, sonication, mechanical disruption, or cell lysing agents.

It may be desired to purify PRO from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular PRO produced.

E. Uses for PRO

Nucleotide sequences (or their complement) encoding PRO have various applications in the art of molecular biology, including uses as hybridization probes, in chromosome and gene mapping and in the generation of anti-sense RNA and DNA. PRO nucleic acid will also be useful for the preparation of PRO polypeptides by the recombinant techniques described herein.

The full-length native sequence PRO gene, or portions thereof, may be used as hybridization probes for a cDNA library to isolate the full-length PRO cDNA or to isolate still other cDNAs (for instance, those encoding naturally-occurring variants of PRO or PRO from other species) which have a desired sequence identity to the native PRO sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO. By way of example, a screening method will comprise isolating the coding region of the PRO gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO nucleic acids include antisense or sense oligonucleotides comprising a singestranded nucleic acid sequence (either RNA or DNA) capable of binding to target PRO mRNA (sense) or PRO DNA (antisense) sequences. Antisense or sense oligonucleotides, according to the present invention, comprise a fragment of the coding region of PRO DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO coding sequences.

Nucleotide sequences encoding a PRO can also be used to construct hybridization probes for mapping the gene which encodes that PRO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO encode a protein which binds to another protein (example, where the PRO is a receptor), the PRO can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO can be used to isolate correlative ligand(s). Screening assays can be designed to find lead compounds that mimic the biological activity of a native PRO or a receptor for PRO. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO can be used to clone genomic DNA encoding PRO in accordance with established techniques and the genomic sequences used to generate transgenic animals that contain cells which express DNA encoding PRO. Methods for generating transgenic animals, particularly animals such as mice or rats, have become conventional in the art and are described, for example, in U.S. Pat. Nos. 4,736,866 and 4,870,009. Typically, particular cells would be targeted for PRO transgene incorporation with tissue-specific enhancers. Transgenic animals that include a copy of a transgene encoding PRO introduced into the germ line of the animal at an embryonic stage can be used to examine the effect of increased expression of DNA encoding PRO. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO can be used to construct a PRO "knock out" animal which has a defective or altered gene encoding PRO as a result of homologous recombination between the endogenous gene encoding PRO and altered genomic DNA encoding PRO introduced into an embryonic stem cell of the animal. For example, cDNA encoding PRO can be used to clone genomic DNA encoding PRO in accordance with established techniques. A portion of the genomic DNA encoding PRO can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach,* E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the PRO polypeptide.

Nucleic acid encoding the PRO polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The PRO polypeptides described herein may also be employed as molecular weight markers for protein electrophoresis purposes and the isolated nucleic acid sequences may be used for recombinantly expressing those markers.

The nucleic acid molecules encoding the PRO polypeptides or fragments thereof described herein are useful for chromosome identification. In this regard, there exists an ongoing need to identify new chromosome markers, since relatively few chromosome marking reagents, based upon actual sequence data are presently available. Each PRO nucleic acid molecule of the present invention can be used as a chromosome marker.

The PRO polypeptides and nucleic acid molecules of the present invention may also be used for tissue typing, wherein the PRO polypeptides of the present invention may be differentially expressed in one tissue as compared to another. PRO nucleic acid molecules will find use for generating probes for PCR, Northern analysis, Southern analysis and Western analysis.

The PRO polypeptides described herein may also be employed as therapeutic agents. The PRO polypeptides of the present invention can be formulated according to known methods to prepare pharmaceutically useful compositions, whereby the PRO product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a PRO polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO polypeptide is desired in a formulation with release characteristics suitable for the treatment of any disease or disorder requiring administration of the PRO polypeptide, microencapsulation of the PRO polypeptide is contemplated. Microencapsulation of recombinant proteins for sustained release has been successfully performed with human growth hormone (rhGH), interferon-(rhIFN-), interleukin-2, and MN rgp120. Johnson et al., *Nat. Med.*, 2:795-799 (1996); Yasuda, *Biomed. Ther.*, 27:1221-1223 (1993); Hora et al., *Bio/Technology*, 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

This invention encompasses methods of screening compounds to identify those that mimic the PRO polypeptide (agonists) or prevent the effect of the PRO polypeptide (antagonists). Screening assays for antagonist drug candidates are designed to identify compounds that bind or complex with the PRO polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO polypeptide encoded by a nucleic acid identified herein under conditions and for a time sufficient to allow these two components to interact.

In binding assays, the interaction is binding and the complex formed can be isolated or detected in the reaction mixture. In a particular embodiment, the PRO polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO polypeptide and drying. Alternatively, an immobilized antibody, e.g., a monoclonal antibody, specific for the PRO polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA,* 88:9578-9582 (1991)) as disclosed by Chevray and Nathans, *Proc. Natl. Acad. Sci. USA,* 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for 1-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO polypeptide may be added to a cell along with the compound to be screened for a particular activity and the ability of the compound to inhibit the activity of interest in the presence of the PRO polypeptide indicates that the compound is an antagonist to the PRO polypeptide. Alternatively, antagonists may be detected by combining the PRO polypeptide and a potential antagonist with membrane-bound PRO polypeptide receptors or recombinant receptors under appropriate conditions for a competitive inhibition assay. The PRO polypeptide can be labeled, such as by radioactivity, such that the number of PRO polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.,* 1(2): Chapter 5 (1991). Preferably, expression cloning is employed wherein polyadenylated RNA is prepared from a cell responsive to the PRO polypeptide and a cDNA library created from this RNA is divided into pools and used to transfect COS cells or other cells that are not responsive to the PRO polypeptide. Transfected cells that are grown on glass slides are exposed to labeled PRO polypeptide. The PRO polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled PRO polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled PRO polypeptide in the presence of the candidate compound. The ability of the compound to enhance or block this interaction could then be measured.

More specific examples of potential antagonists include an oligonucleotide that binds to the fusions of immunoglobulin with PRO polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO polypeptide that recognizes the receptor but imparts no effect, thereby competitively inhibiting the action of the PRO polypeptide.

Another potential PRO polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.,* 6:3073 (1979); Cooney et al., *Science,* 241: 456 (1988); Dervan et al., *Science,* 251:1360 (1991)), thereby preventing transcription and the production of the PRO polypeptide. The antisense RNA oligonucleotide hybridizes to the mRNA in vivo and blocks translation of the mRNA molecule into the PRO polypeptide (antisense-Okano, Neurochem., 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO polypeptide, thereby blocking the normal biological activity of the PRO polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology,* 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

With regard to the PRO211 and PRO217 polypeptide, therapeutic indications include disorders associated with the preservation and maintenance of gastrointestinal mucosa and the repair of acute and chronic mucosal lesions (e.g., enterocolitis, Zollinger-Ellison syndrome, gastrointestinal ulceration and congenital microvillus atrophy), skin diseases associated with abnormal keratinocyte differentiation (e.g., psoriasis, epithelial cancers such as lung squamous cell carcinoma, epidermoid carcinoma of the vulva and gliomas.

Uses of the herein disclosed molecules may also be based upon the positive functional assay hits disclosed and described below.

F. Anti-PRO Antibodies

The present invention further provides anti-PRO antibodies. Exemplary antibodies include polyclonal, monoclonal, humanized, bispecific, and heteroconjugate antibodies.

1. Polyclonal Antibodies

The anti-PRO antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against PRO. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522-525 (1986); Riechmann et al., *Nature,* 332:323-329 (1988); and Presta, *Curr. Op. Struct. Biol.,* 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522-525 (1986); Riechmann et al., *Nature,* 332:323-327 (1988); Verhoeyen et al., *Science,* 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

4. Bispecific Antibodies

Bispecific antibodies are monoclonal, preferably human or humanized, antibodies that have binding specificities for at least two different antigens. In the present case, one of the binding specificities is for the PRO, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from E. coli and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies may bind to two different epitopes on a given PRO polypeptide herein. Alternatively, an anti-PRO polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD 16) so as to focus cellular defense mechanisms to the cell expressing the particular PRO polypeptide. Bispecific antibodies may also be used to localize cytotoxic agents to cells which express a particular PRO polypeptide. These antibodies possess a PRO-binding arm and an arm which binds a cytotoxic agent or a radionuclide chelator, such as EOTUBE, DPTA, DOTA, or TETA. Another bispecific antibody of interest binds the PRO polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.*, 176: 1191-1195 (1992) and Shopes, *J. Immunol.*, 148: 2918-2922 (1992). Homodimeric antibodies with enhanced anti-tumor activity may also be prepared using heterobifunctional crosslinkers as described in Wolff et al. *Cancer Research*, 53: 2560-2565 (1993). Alternatively, an antibody can be engineered that has dual Fc regions and may thereby have enhanced complement lysis and ADCC capabilities. See Stevenson et al., *Anti-Cancer Drug Design*, 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl. Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286-288 (1982) via a disulfide-interchange reaction. A chemotherapeutic agent (such as Doxorubicin) is optionally contained within the liposome. See Gabizon et al., *J. National Cancer Inst.*, 81(19):1484 (1989).

9. Pharmaceutical Compositions of Antibodies

Antibodies specifically binding a PRO polypeptide identified herein, as well as other molecules identified by the screening assays disclosed hereinbefore, can be administered for the treatment of various disorders in the form of pharmaceutical compositions.

If the PRO polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA* 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Anti-PRO Antibodies

The anti-PRO antibodies of the invention have various utilities. For example, anti-PRO antibodies may be used in diagnostic assays for PRO, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem., and Cytochem.*, 30:407 (1982).

Anti-PRO antibodies also are useful for the affinity purification of PRO from recombinant cell culture or natural sources. In this process, the antibodies against PRO are immobilized on a suitable support, such a Sephadex resin or filter paper, using methods well known in the art. The immobilized antibody then is contacted with a sample containing the PRO to be purified, and thereafter the support is washed with a suitable solvent that will remove substantially all the material in the sample except the PRO, which is bound to the immobilized antibody. Finally, the support is washed with another suitable solvent that will release the PRO from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Rockville, Md.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST2 (Altschul, and Gish, *Methods in Enzymology* 266: 460-80 (1996) as a comparison of the ECD protein sequences to a 6 frame translation of the EST sequences. Those comparisons with a Blast score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences. In addition, the consensus DNA sequences obtained were often (but not always) extended using repeated cycles of BLAST and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward (.f) and reverse (.r) PCR primers generally range from 20 to 30 nucleotides and are often designed to give a PCR product of about 100-1000 bp in length. The probe (.p) sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253: 1278-1280 (1991)) in the unique XhoI and NotI sites.

Example 2

Isolation of cDNA Clones Encoding PRO211 and PRO217

Consensus DNA sequences were assembled as described in Example 1 above and were designated as DNA28730 and DNA28760, respectively. Based on these consensus sequences, oligonucleotides were synthesized and used to identify by PCR a cDNA library that contained the sequences of interest and for use as probes to isolate a clone of the full-length coding sequence for the PRO211 and PRO217 polypeptides. The libraries used to isolate DNA32292-1131 and DNA33094-1131 were fetal lung libraries.

cDNA clones were sequenced in their entirety. The entire nucleotide sequences of PRO211 (DNA32292-1131) and PRO217 (UNQ191) are shown in FIG. 1 (SEQ ID NO: 1) and FIG. 3 (SEQ ID NO:3), respectively. The predicted polypeptides are 353 and 379 amino acid in length, respectively, with respective molecular weights of approximately 38,190 and 41,520 daltons.

The oligonucleotide sequences used in the above procedures were the following:

```
28730.p (OLI 516)                           (SEQ ID NO:5)
5'-AGGGAGCACGGACAGTGTGCAGATGTGGACGAGTGCTCACTAGCA-3'

28730.f (OLI 517)                           (SEQ ID NO:6)
5'-AGAGTGTATCTCTGGCTACGC-3'

28730.r (OLI 518)                           (SEQ ID NO:7)
5'-TAAGTCCGGCACATTACAGGTC-3'

28760.p (OLI 617)                           (SEQ ID NO:8)
5'-CCCACGATGTATGAATGGTGGACTTTGTGTGACTCCTGGTTTCTGCA
TC-3'

28760.f (OLI 618)                           (SEQ ID NO:9)
5'-AAAGACGCATCTGCGAGTGTCC-3'

28760.r (OLI 619)                           (SEQ ID NO:10)
5'-TGCTGATTTCACACTGCTCTCCC-3'
```

Example 3

Use of PRO Polypeptide-Encoding Nucleic Acid as Hybridization Probes

The following method describes use of a nucleotide sequence encoding a PRO polypeptide as a hybridization probe.

DNA comprising the coding sequence of of a PRO polypeptide of interest as disclosed herein may be employed as a probe or used as a basis from which to prepare probes to screen for homologous DNAs (such as those encoding naturally-occurring variants of the PRO polypeptide) in human tissue cDNA libraries or human tissue genomic libraries.

Hybridization and washing of filters containing either library DNAs is performed under the following high stringency conditions. Hybridization of radiolabeled PRO polypeptide-encoding nucleic acid-derived probe to the filters is performed in a solution of 50% formamide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO polypeptide can then be identified using standard techniques known in the art.

Example 4

Expression of PRO Polypeptides in *E. coli*

This example illustrates preparation of an unglycosylated form of a desired PRO polypeptide by recombinant expression in *E. coli*.

The DNA sequence encoding the desired PRO polypeptide is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the specific PRO polypeptide coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO polypeptide can then be purified using a metal chelating column under conditions that allow tight binding of the protein.

PRO187, PRO317, PRO301, PRO224 and PRO238 were successfully expressed in *E. coli* in a poly-His tagged form, using the following procedure. The DNA encoding PRO187, PRO317, PRO301, PRO224 or PRO238 was initially amplified using selected PCR primers. The primers contained restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences were then ligated into an expression vector, which was used to transform an *E. coli* host based on strain 52 (W3110 fuhA(tonA) lon galE rpoHts(htpRts) clpP(lacIq). Transformants were first grown in LB containing 50 mg/ml carbenicillin at 30° C. with shaking until an O.D.600 of 3-5 was reached. Cultures were then diluted 50-100 fold into CRAP media (prepared by mixing 3.57 g $(NH_4)_2SO_4$, 0.71 g sodium citrate $2H_2O$, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples were removed to verify expression by SDS-PAGE analysis, and the bulk culture is centrifuged to pellet the cells. Cell pellets were frozen until purification and refolding.

*E. coli* paste from 0.5 to 1 L fermentations (6-10 g pellets) was resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution was stirred overnight at 4° C. This step results in a denatured protein with all cysteine residues blocked by sulfitolization. The solution was centrifuged at 40,000 rpm in a Beckman Ultracentifuge for 30 min. The supernatant was diluted with 3-5 volumes of metal chelate column buffer (6 M guanidine, 20 mM Tris, pH 7.4) and filtered through 0.22 micron filters to clarify. Depending the clarified extract was loaded onto a 5 ml Qiagen Ni-NTA metal chelate column equilibrated in the metal chelate column buffer. The column was washed with additional buffer containing 50 mM imidazole (Calbiochem, Utrol grade), pH 7.4. The protein was eluted with buffer containing 250 mM imidazole. Fractions containing the desired protein were pooled and stored at 4° C. Protein concentration was estimated by its absorbance at 280 nm using the calculated extinction coefficient based on its amino acid sequence.

The proteins were refolded by diluting sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes were chosen so that the final protein concentration was between 50 to 100 micrograms/ml. The refolding solution was stirred gently at 4° C. for 12-36 hours. The refolding reaction was quenched by the addition of TFA to a final concentration of 0.4% (pH of approximately 3). Before further purification of the protein, the solution was filtered through a 0.22 micron filter and acetonitrile was added to 2-10% final concentration. The refolded protein was chromatographed on a Poros R1/H reversed phase column using a mobile buffer of 0.1% TFA with elution with a gradient of acetonitrile from 10 to 80%. Aliquots of fractions with A280 absorbance were analyzed on SDS polyacrylamide gels and fractions containing homogeneous refolded protein were pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO187, PRO317, PRO301, PRO224 and PRO238 proteins, respectively, were pooled and the acetonitrile removed using a gentle stream of nitrogen directed at the solution. Proteins were formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 5

Expression of PRO Polypeptides in Mammalian Cells

This example illustrates preparation of a glycosylated form of a desired PRO polypeptide by recombinant expression in mammalian cells.

The vector, pRK5 (see EP 307,247, published Mar. 15, 1989), is employed as the expression vector. Optionally, the PRO polypeptide-encoding DNA is ligated into pRK5 with selected restriction enzymes to allow insertion of the PRO polypeptide DNA using ligation methods such as described in Sambrook et al., supra. The resulting vector is called pRK5-PRO polypeptide.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO polypeptide DNA is mixed with about 1 μg DNA encoding the VA RNA gene [Thimmappaya et al., *Cell*, 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO polypeptide. The cultures containing transfected cells may undergo further incubation (in serum free medium) and the medium is tested in selected bioassays.

In an alternative technique, PRO polypeptide may be introduced into 293 cells transiently using the dextran sulfate method described by Somparyrac et al., *Proc. Natl. Acad. Sci.*, 12:7575 (1981). 293 cells are grown to maximal density in a spinner flask and 700 μg pRK5-PRO polypeptide DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed PRO polypeptide can then be concentrated and purified by any selected method, such as dialysis and/or column chromatography.

In another embodiment, PRO polypeptides can be expressed in CHO cells. The pRK5-PRO polypeptide can be transfected into CHO cells using known reagents such as CaPO$_4$ or DEAE-dextran. As described above, the cell cultures can be incubated, and the medium replaced with culture medium (alone) or medium containing a radiolabel such as $^{35}$S-methionine. After determining the presence of PRO polypeptide, the culture medium may be replaced with serum free medium. Preferably, the cultures are incubated for about 6 days, and then the conditioned medium is harvested. The medium containing the expressed PRO polypeptide can then be concentrated and purified by any selected method.

Epitope-tagged PRO polypeptide may also be expressed in host CHO cells. The PRO polypeptide may be subcloned out of the pRK5 vector. The subclone insert can undergo PCR to fuse in frame with a selected epitope tag such as a poly-his tag into a Baculovirus expression vector. The poly-his tagged PRO polypeptide insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO polypeptide can then be concentrated and purified by any selected method, such as by Ni$^{2+}$-chelate affinity chromatography.

PRO211, PRO217, PRO230, PRO219, PRO245, PRO221, PRO258, PRO301, PRO224, PRO222, PRO234, PRO229, PRO223, PRO328 and PRO332 were successfully expressed in CHO cells by both a transient and a stable expression procedure. In addition, PRO232, PRO265, PRO246, PRO228, PRO227, PRO220, PRO266, PRO269, PRO287, PRO214, PRO231, PRO233, PRO238, PRO244, PRO235, PRO236, PRO262, PRO239, PRO257, PRO260, PRO263, PRO270, PRO271, PRO272, PRO294, PRO295, PRO293, PRO247, PRO303 and PRO268 were successfully transiently expressed in CHO cells.

Stable expression in CHO cells was performed using the following procedure. The proteins were expressed as an IgG construct (immunoadhesin), in which the coding sequences for the soluble forms (e.g. extracellular domains) of the respective proteins were fused to an IgG1 constant region sequence containing the hinge, CH2 and CH2 domains and/or is a poly-His tagged form.

Following PCR amplification, the respective DNAs were subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24: 9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA were introduced into approximately 10 million CHO cells using commercially available transfection reagents SUPER-FECT® (Quiagen), DOSPER® or FUGENE® (Boehringer Mannheim). The cells were grown and described in Lucas et al., supra. Approximately 3×10$^{-7}$ cells are frozen in an ampule for further growth and production as described below.

The ampules containing the plasmid DNA were thawed by placement into water bath and mixed by vortexing. The contents were pipetted into a centrifuge tube containing 10 mLs of media and centrifuged at 1000 rpm for 5 minutes. The supernatant was aspirated and the cells were resuspended in 10 mL of selective media (0.2 μm filtered PS20 with 5% 0.2 μm diafiltered fetal bovine serum). The cells were then aliquoted into a 100 mL spinner containing 90 mL of selective media. After 1-2 days, the cells were transferred into a 250 mL spinner filled with 150 mL selective growth medium and incubated at 37° C. After another 2-3 days, a 250 mL, 500 mL and 2000 mL spinners were seeded with 3×10$^5$ cells/mL. The cell media was exchanged with fresh media by centrifugation and resuspension in production medium. Although any suitable CHO media may be employed, a production medium described in U.S. Pat. No. 5,122,469, issued Jun. 16, 1992 was actually used. 3L production spinner is seeded at 1.2×10$^6$ cells/mL. On day 0, the cell number pH were determined. On day 1, the spinner was sampled and sparging with filtered air was commenced. On day 2, the spinner was sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion). Throughout the production, pH was adjusted as necessary to keep at around 7.2. After 10 days, or until viability dropped below 70%, the cell culture was harvested by centrifugtion and filtering through a 0.22 μm filter. The filtrate was either stored at 4° C. or immediately loaded onto columns for purification.

For the poly-His tagged constructs, the proteins were purified using a Ni-NTA column (Qiagen). Before purification, imidazole was added to the conditioned media to a concentration of 5 mM. The conditioned media was pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column was washed with additional equilibration buffer and the protein eluted with equilibration buffer containing 0.25 M imidazole. The highly purified protein was subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc containing) constructs of were purified from the conditioned media as follows. The conditioned medium was pumped onto a 5 ml Protein A column (Pharmacia) which had been equilibrated in 20 mM Na phosphate buffer, pH 6.8. After loading, the column was washed extensively with equilibration buffer before elution with 100 mM citric acid, pH 3.5. The eluted protein was immediately neutralized by collecting 1 ml fractions into tubes containing 275 μL of 1 M Tris buffer, pH 9. The highly purified protein was subsequently desalted into storage buffer as described above for the poly-His tagged proteins. The homogeneity was assessed by SDS polyacrylamide gels and by N-terminal amino acid sequencing by Edman degradation.

PRO211, PRO217 were also successfully transiently expressed in COS cells.

Example 6

Expression of PRO Polypeptides in Yeast

The following method describes recombinant expression of a desired PRO polypeptide in yeast.

First, yeast expression vectors are constructed for intracellular production or secretion of PRO polypeptides from the ADH2/GAPDH promoter. DNA encoding a desired PRO polypeptide, a selected signal peptide and the promoter is inserted into suitable restriction enzyme sites in the selected plasmid to direct intracellular expression of the PRO polypeptide. For secretion, DNA encoding the PRO polypeptide can be cloned into the selected plasmid, together with DNA encoding the ADH2/GAPDH promoter, the yeast alpha-factor secretory signal/leader sequence, and linker sequences (if needed) for expression of the PRO polypeptide.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO polypeptide can subsequently be isolated and purified by removing the yeast cells from the fermentation medium by centrifugation and then concentrating the medium using selected cartridge filters. The concentrate containing the PRO polypeptide may further be purified using selected column chromatography resins.

Example 7

Expression of PRO Polypeptides in Baculovirus-Infected Insect Cells

The following method describes recombinant expression of PRO polypeptides in Baculovirus-infected insect cells.

The desired PRO polypeptide is fused upstream of an epitope tag contained with a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the PRO polypeptide or the desired portion of the PRO polypeptide (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BACULOGOLD™ virus DNA (Pharmingen) into *Spodoptera frugiperda* ("Sf9") cells (ATCC CRL 1711) using LIPOFECTIN®(commercially available from GIBCO-BRL). After 4-5 days of incubation at 28° C., the released viruses are harvested and used for further amplifications. Viral infection and protein expression is performed as described by O'Reilley et al., Baculovirus expression vectors: A Laboratory Manual, Oxford: Oxford University Press (1994).

Expressed poly-his tagged PRO polypeptide can then be purified, for example, by $Ni^{2+}$-chelate affinity chromatography as follows. Extracts are prepared from recombinant virus-infected Sf9 cells as described by Rupert et al., Nature, 362:175-179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged PRO polypeptide are pooled and dialyzed against loading buffer.

Alternatively, purification of the IgG tagged (or Fc tagged) PRO polypeptide can be performed using known chromatography techniques, including for instance, Protein A or protein G column chromatography.

PRO211, PRO217 were successfully expressed in baculovirus infected Sf9 or high5 insect cells. While the expression was actually performed in a 0.5-2 L scale, it can be readily scaled up for larger (e.g. 8 L) preparations. The proteins were expressed as an IgG construct (immunoadhesin), in which the protein extracellular region was fused to an IgG1 constant region sequence containing the hinge, CH2 and CH3 domains and/or in poly-His tagged forms.

Following PCR amplification, the respective coding sequences were subcloned into a baculovirus expression vector (pb.PH.IgG for IgG fusions and pb.PH.His.c for poly-His tagged proteins), and the vector and BACULOGOLD® baculovirus DNA (Pharmingen) were co-transfected into 105 *Spodoptera frugiperda* ("Sf9") cells (ATCC CRL 1711), using LIPOFECTIN® (Gibco BRL). pb.PH.IgG and pb.PH.His are modifications of the commercially available baculovirus expression vector pVL1393 (Pharmingen), with modified polylinker regions to include the His or Fc tag sequences. The cells were grown in Hink's TNM-FH medium supplemented with 10% FBS (Hyclone). Cells were incubated for 5 days at 28° C. The supernatant was harvested and subsequently used for the first viral amplification by infecting Sf9 cells in Hink's TNM-FH medium supplemented with 10% FBS at an approximate multiplicity of infection (MOI) of 10. Cells were incubated for 3 days at 28° C. The supernatant was harvested and the expression of the constructs in the baculovirus expression vector was determined by batch binding of 1 ml of supernatant to 25 mL of Ni-NTA beads (QIAGEN) for histidine tagged proteins or Protein-A SEPHAROSE™ CL-4B beads (Pharmacia) for IgG tagged proteins followed by SDS-PAGE analysis comparing to a known concentration of protein standard by Coomassie blue staining.

The first viral amplification supernatant was used to infect a spinner culture (500 ml) of Sf9 cells grown in ESF-921 medium (Expression Systems LLC) at an approximate MOI of 0.1. Cells were incubated for 3 days at 28° C. The supernatant was harvested and filtered. Batch binding and SDS-PAGE analysis was repeated, as necessary, until expression of the spinner culture was confirmed.

The conditioned medium from the transfected cells (0.5 to 3 L) was harvested by centrifugation to remove the cells and filtered through 0.22 micron filters. For the poly-His tagged constructs, the protein construct were purified using a Ni-NTA column (Qiagen). Before purification, imidazole was added to the conditioned media to a concentration of 5 mM. The conditioned media were pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column was washed with additional equilibration buffer and the protein eluted with equilibration buffer containing 0.25 M imidazole. The highly purified protein was subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc containing) constructs of proteins were purified from the conditioned media as follows. The conditioned media were pumped onto a 5 ml Protein A column (Pharmacia) which had been equilibrated in 20 mM Na phosphate buffer, pH 6.8. After loading, the column was washed extensively with equilibration buffer before elution with 100 mM citric acid, pH 3.5. The eluted protein was immediately neutralized by collecting 1 ml fractions into tubes containing 275 mL of 1 M Tris buffer, pH 9. The highly purified protein was subsequently desalted into storage buffer as described above for the poly-His tagged proteins. The homogeneity of the proteins was verified by SDS polyacrylamide gel (PEG) electrophoresis and N-terminal amino acid sequencing by Edman degradation.

Example 8

Preparation of Antibodies that Bind to PRO Polypeptides

This example illustrates preparation of monoclonal antibodies which can specifically bind to a PRO polypeptide.

Techniques for producing the monoclonal antibodies are known in the art and are described, for instance, in Goding, supra. Immunogens that may be employed include purified PRO polypeptide, fusion proteins containing the PRO polypeptide, and cells expressing recombinant PRO polypeptide on the cell surface. Selection of the immunogen can be made by the skilled artisan without undue experimentation.

Mice, such as Balb/c, are immunized with the PRO polypeptide immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO polypeptide antibodies.

After a suitable antibody titer has been detected, the animals "positive" for antibodies can be injected with a final intravenous injection of PRO polypeptide. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against the PRO polypeptide. Determination of "positive" hybridoma cells secreting the desired monoclonal antibodies against the PRO polypeptide is within the skill in the art.

The positive hybridoma cells can be injected intraperitoneally into syngeneic Balb/c mice to produce ascites containing the anti-PRO polypeptide monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 9

Chimeric PRO Polypeptides

PRO polypeptides may be expressed as chimeric proteins with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS™ extension/affinity purification system (Immunex Corp., Seattle Wash.). The inclusion of a cleavable linker sequence such as Factor XA or enterokinase (Invitrogen, San Diego Calif.) between the purification domain and the PRO polypeptide sequence may be useful to facilitate expression of DNA encoding the PRO polypeptide.

Example 10

Purification of PRO Polypeptides Using Specific Antibodies

Native or recombinant PRO polypeptides may be purified by a variety of standard techniques in the art of protein purification. For example, pro-PRO polypeptide, mature PRO polypeptide, or pre-PRO polypeptide is purified by immunoaffinity chromatography using antibodies specific for the PRO polypeptide of interest. In general, an immunoaffinity column is constructed by covalently coupling the anti-PRO polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO polypeptide by preparing a fraction from cells containing PRO polypeptide in a soluble form. This preparation is derived by solubilization of the whole cell or of a subcellular fraction obtained via differential centrifugation by the addition of detergent or by other methods well known in the art. Alternatively, soluble PRO polypeptide containing a signal sequence may be secreted in useful quantity into the medium in which the cells are grown.

A soluble PRO polypeptide-containing preparation is passed over the immunoaffinity column, and the column is washed under conditions that allow the preferential absorbance of PRO polypeptide (e.g., high ionic strength buffers in the presence of detergent). Then, the column is eluted under conditions that disrupt antibody/PRO polypeptide binding (e.g., a low pH buffer such as approximately pH 2-3, or a high concentration of a chaotrope such as urea or thiocyanate ion), and PRO polypeptide is collected.

Example 11

Drug Screening

This invention is particularly useful for screening compounds by using PRO polypeptides or binding fragment thereof in any of a variety of drug screening techniques. The PRO polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO polypeptide or fragment. Drugs are screened against such transformed cells in competitive binding assays. Such cells, either in viable or fixed form, can be used for standard binding assays. One may measure, for example, the formation of complexes between PRO polypeptide or a fragment and the agent being tested. Alternatively, one can examine the diminution in complex formation between the PRO polypeptide and its target cell or target receptors caused by the agent being tested.

Thus, the present invention provides methods of screening for drugs or any other agents which can affect a PRO polypeptide-associated disease or disorder. These methods comprise contacting such an agent with an PRO polypeptide or fragment thereof and assaying (I) for the presence of a complex between the agent and the PRO polypeptide or fragment, or (ii) for the presence of a complex between the PRO polypeptide or fragment and the cell, by methods well known in the art. In such competitive binding assays, the PRO polypeptide or fragment is typically labeled. After suitable incubation, free PRO polypeptide or fragment is separated from that present in bound form, and the amount of free or uncomplexed label is a measure of the ability of the particular agent to bind to PRO polypeptide or to interfere with the PRO polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO polypeptide, the peptide test compounds are reacted with PRO polypeptide and washed. Bound PRO polypeptide is detected by methods well known in the art. Purified PRO polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO polypeptide specifically compete with a test compound for binding to PRO polypeptide or fragments thereof. In this manner, the antibodies can be used to detect the presence of any peptide which shares one or more antigenic determinants with PRO polypeptide.

Example 12

Rational Drug Design

The goal of rational drug design is to produce structural analogs of biologically active polypeptide of interest (i.e., a PRO polypeptide) or of small molecules with which they interact, e.g., agonists, antagonists, or inhibitors. Any of these examples can be used to fashion drugs which are more active or stable forms of the PRO polypeptide or which enhance or interfere with the function of the PRO polypeptide in vivo (c.f., Hodgson, *Bio/Technology*, 9: 19-21 (1991)).

In one approach, the three-dimensional structure of the PRO polypeptide, or of an PRO polypeptide-inhibitor complex, is determined by x-ray crystallography, by computer modeling or, most typically, by a combination of the two approaches. Both the shape and charges of the PRO polypeptide must be ascertained to elucidate the structure and to determine active site(s) of the molecule. Less often, useful information regarding the structure of the PRO polypeptide may be gained by modeling based on the structure of homologous proteins. In both cases, relevant structural information is used to design analogous PRO polypeptide-like molecules or to identify efficient inhibitors. Useful examples of rational drug design may include molecules which have improved activity or stability as shown by Braxton and Wells, *Biochemistry*, 31:7796-7801 (1992) or which act as inhibitors, agonists, or antagonists of native peptides as shown by Athauda et al., *J. Biochem.*, 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO polypeptide may be made available to perform such analytical studies as X-ray crystallography. In addition, knowledge of the PRO polypeptide amino acid sequence provided herein will provide guidance to those employing computer modeling techniques in place of or in addition to x-ray crystallography.

Example 13

Ability of PRO Polypeptides to Inhibit Vascular Endothelial Growth Factor (VEGF) Stimulated Proliferation of Endothelial Cell Growth (Assay 9)

The ability of various PRO polypeptides to inhibit VEGF stimulated proliferation of endothelial cells was tested. Polypeptides testing positive in this assay are useful for inhibiting endothelial cell growth in mammals where such an effect would be beneficial, e.g., for inhibiting tumor growth.

Specifically, bovine adrenal cortical capillary endothelial cells (ACE) (from primary culture, maximum of 12-14 passages) were plated in 96-well plates at 500 cells/well per 100 microliter. Assay media included low glucose DMEM, 10% calf serum, 2 mM glutamine, and 1× penicillin/streptomycin/fungizone. Control wells included the following: (1) no ACE cells added; (2) ACE cells alone; (3) ACE cells plus 5 ng/ml FGF; (4) ACE cells plus 3 ng/ml VEGF; (5) ACE cells plus 3 ng/ml VEGF plus 1 ng/ml TGF-beta; and (6) ACE cells plus 3 ng/ml VEGF plus 5 ng/ml LIF. The test samples, poly-his tagged PRO polypeptides (in 100 microliter volumes), were then added to the wells (at dilutions of 1%, 0.1% and 0.01%, respectively). The cell cultures were incubated for 6-7 days at 37° C./5% $CO_2$. After the incubation, the media in the wells was aspirated, and the cells were washed 1× with PBS. An acid phosphatase reaction mixture (100 microliter; 0.1M sodium acetate, pH 5.5, 0.1% Triton X-100, 10 mM p-nitrophenyl phosphate) was then added to each well. After a 2 hour incubation at 37° C., the reaction was stopped by addition of 10 microliters 1N NaOH. Optical density (OD) was measured on a microplate reader at 405 nm.

The activity of PRO polypeptides was calculated as the percent inhibition of VEGF (3 ng/ml) stimulated proliferation (as determined by measuring acid phosphatase activity at OD 405 nm) relative to the cells without stimulation. TGF-beta was employed as an activity reference at 1 ng/ml, since TGF-beta blocks 70-90% of VEGF-stimulated ACE cell proliferation. The results are indicative of the utility of the PRO polypeptides in cancer therapy and specifically in inhibiting tumor angiogenesis. Numerical values (relative inhibition) are determined by calculating the percent inhibition of VEGF stimulated proliferation by the PRO polypeptides relative to cells without stimulation and then dividing that percentage into the percent inhibition obtained by TGF-β at 1 ng/ml which is known to block 70-90% of VEGF stimulated cell proliferation. The results are considered positive if the PRO polypeptide exhibits 30% or greater inhibition of VEGF stimulation of endothelial cell growth (relative inhibition 30% or greater).

The following polypeptides tested positive in this assay: PRO211, PRO217.

Example 14

Induction of Endothelial Cell Apoptosis (Assay 73)

The ability of PRO polypeptides to induce apoptosis in endothelial cells was tested in human venous umbilical vein endothelial cells (HUVEC, Cell Systems). A positive test in the assay is indicative of the usefulness of the polypeptide in therapeutically treating tumors as well as vascular disorders where inducing apoptosis of endothelial cells would be beneficial.

The cells were plated on 96-well microtiter plates (Amersham Life Science, cytostar-T scintillating microplate, RPNQ160, sterile, tissue-culture treated, individually wrapped), in 10% serum (CSG-medium, Cell Systems), at a density of $2 \times 10^4$ cells per well in a total volume of 100 μl. On day 2, test samples containing the PRO polypeptide were added in triplicate at dilutions of 1%, 0.33% and 0.11%. Wells without cells were used as a blank and wells with cells only were used as a negative control. As a positive control 1:3 serial dilutions of 50 μl of a 3× stock of staurosporine were used. The ability of the PRO polypeptide to induce apoptosis was determined by processing of the 96 well plates for detection of Annexin V, a member of the calcium and phospholipid binding proteins, to detect apoptosis.

0.2 ml Annexin V—Biotin stock solution (100 μg/ml) was diluted in 4.6 ml $2 \times Ca^{2+}$ binding buffer and 2.5% BSA (1:25 dilution). 50 μl of the diluted Annexin V—Biotin solution was added to each well (except controls) to a final concentration of 1.0 μg/ml. The samples were incubated for 10-15 minutes with Annexin-Biotin prior to direct addition of $^{35}$S-Streptavidin. $^{35}$S-Streptavidin was diluted in $2 \times Ca^{2+}$ Binding buffer, 2.5% BSA and was added to all wells at a final concentration of $3 \times 10^4$ cpm/well. The plates were then sealed, centrifuged at 1000 rpm for 15 minutes and placed on orbital shaker for 2 hours. The analysis was performed on a 1450 Microbeta Trilux (Wallac). Percent above background represents the percentage amount of counts per minute above the negative controls. Percents greater than or equal to 30% above background are considered positive.

The following PRO polypeptides tested positive in this assay: PRO228, PRO217 and PRO301.

Example 15

PDB12 Cell Inhibition (Assay 40)

This example demonstrates that various PRO polypeptides have efficacy in inhibiting protein production by PDB 12 pancreatic ductal cells and are, therefore, useful in the therapeutic treatment of disorders which involve protein secretion by the pancreas, including diabetes, and the like.

PDB12 pancreatic ductal cells are plated on fibronectin coated 96 well plates at $1.5 \times 10^3$ cells per well in 100 μL/180 μL of growth media. 100 μL of growth media with the PRO polypeptide test sample or negative control lacking the PRO polypeptide is then added to well, for a final volume of 200 μL. Controls contain growth medium containing a protein shown to be inactive in this assay. Cells are incubated for 4 days at 37° C. 20 μL of ALAMAR BLUE™ Dye (AB) is then added to each well and the flourescent reading is measured at 4 hours post addition of AB, on a microtiter plate reader at 530 nm excitation and 590 nm emission. The standard employed is cells without Bovine Pituitary Extract (BPE) and with various concentrations of BPE. Buffer or CM controls from unknowns are run 2 times on each 96 well plate.

These assays allow one to calculate a percent decrease in protein production by comparing the ALAMAR BLUE™ Dye calculated protein concentration produced by the PRO polypeptide-treated cells with the ALAMAR BLUE™ Dye calculated protein concentration produced by the negative control cells. A percent decrease in protein production of greater than or equal to 25% as compared to the negative control cells is considered positive.

The following polypeptides tested positive in this assay: PRO211, PRO287, PRO301 and PRO293.

Example 16

Stimulatory Activity in Mixed Lymphocyte Reaction (MLR) Assay (Assay 24)

This example shows that certain polypeptides of the invention are active as a stimulator of the proliferation of stimulated T-lymphocytes. Compounds which stimulate proliferation of lymphocytes are useful therapeutically where enhancement of an immune response is beneficial. A therapeutic agent may take the form of antagonists of the polypeptide of the invention, for example, murine-human chimeric, humanized or human antibodies against the polypeptide.

The basic protocol for this assay is described in Current Protocols in Immunology, unit 3.12; edited by J E Coligan, A M Kruisbeek, D H Marglies, E M Shevach, W Strober, National Institutes of Health, Published by John Wiley & Sons, Inc.

More specifically, in one assay variant, peripheral blood mononuclear cells (PBMC) are isolated from mammalian individuals, for example a human volunteer, by leukopheresis (one donor will supply stimulator PBMCs, the other donor will supply responder PBMCs). If desired, the cells are frozen in fetal bovine serum and DMSO after isolation. Frozen cells may be thawed overnight in assay media (37° C., 5% $CO_2$) and then washed and resuspended to $3 \times 10^6$ cells/ml of assay media (RPMI; 10% fetal bovine serum, 1% penicillin/streptomycin, 1% glutamine, 1% HEPES, 1% non-essential amino acids, 1% pyruvate). The stimulator PBMCs are prepared by irradiating the cells (about 3000 Rads).

The assay is prepared by plating in triplicate wells a mixture of:
- 100:1 of test sample diluted to 1% or to 0.1%,
- 50:1 of irradiated stimulator cells, and
- 50:1 of responder PBMC cells.

100 microliters of cell culture media or 100 microliter of CD4-IgG is used as the control. The wells are then incubated at 37° C., 5% $CO_2$ for 4 days. On day 5, each well is pulsed with tritiated thymidine (1.0 mC/well; Amersham). After 6 hours the cells are washed 3 times and then the uptake of the label is evaluated.

In another variant of this assay, PBMCs are isolated from the spleens of Balb/c mice and C57B6 mice. The cells are teased from freshly harvested spleens in assay media (RPMI; 10% fetal bovine serum, 1% penicillin/streptomycin, 1% glutamine, 1% HEPES, 1% non-essential amino acids, 1% pyruvate) and the PBMCs are isolated by overlaying these cells over Lympholyte M (Organon Teknika), centrifuging at 2000 rpm for 20 minutes, collecting and washing the mononuclear cell layer in assay media and resuspending the cells to $1 \times 10^7$ cells/ml of assay media. The assay is then conducted as described above.

Positive increases over control are considered positive with increases of greater than or equal to 180% being preferred. However, any value greater than control indicates a stimulatory effect for the test protein.

The following PRO polypeptides tested positive in this assay: PRO245, PRO269, PRO217, PRO301, PRO266, PRO335, PRO331, PRO533 and PRO326.

Example 17

Ability of PRO Polypeptides to Stimulate the Release of Proteoglycans from Cartilage (Assay 97)

The ability of various PRO polypeptides to stimulate the release of proteoglycans from cartilage tissue was tested as follows.

The metacrphophalangeal joint of 4-6 month old pigs was aseptically dissected, and articular cartilage was removed by free hand slicing being careful to avoid the underlying bone. The cartilage was minced and cultured in bulk for 24 hours in a humidified atmosphere of 95% air, 5% $CO_2$ in serum free (SF) media (DME/F12 1:1) woth 0.1% BSA and 100 U/ml penicillin and 100 µg/ml streptomycin. After washing three times, approximately 100 mg of articular cartilage was aliquoted into micronics tubes and incubated for an additional 24 hours in the above SF media. PRO polypeptides were then added at 1% either alone or in combination with 18 ng/ml interleukin-1α, a known stimulator of proteoglycan release from cartilage tissue. The supernatant was then harvested and assayed for the amount of proteoglycans using the 1,9-dimethyl-methylene blue (DMB) colorimetric assay (Farndale and Buttle, *Biochem. Biophys. Acta* 883:173-177 (1985)). A positive result in this assay indicates that the test polypeptide will find use, for example, in the treatment of sports-related joint problems, articular cartilage defects, osteoarthritis or rheumatoid arthritis.

When various PRO polypeptides were tested in the above assay, the polypeptides demonstrated a marked ability to stimulate release of proteoglycans from cartilage tissue both basally and after stimulation with interleukin-1α and at 24 and 72 hours after treatment, thereby indicating that these PRO polypeptides are useful for stimulating proteoglycan release from cartilage tissue. As such, these PRO polypeptides are useful for the treatment of sports-related joint problems, articular cartilage defects, osteoarthritis or rheumatoid arthritis. The polypeptides testing positive in this assay are: PRO211.

Example 18

Skin Vascular Permeability Assay (Assay 64)

This assay shows that certain polypeptides of the invention stimulate an immune response and induce inflammation by inducing mononuclear cell, eosinophil and PMN infiltration at the site of injection of the animal. Compounds which stimulate an immune response are useful therapeutically where stimulation of an immune response is beneficial. This skin vascular permeability assay is conducted as follows. Hairless guinea pigs weighing 350 grams or more are anesthetized with ketamine (75-80 mg/Kg) and 5 mg/Kg xylazine intramuscularly (IM). A sample of purified polypeptide of the invention or a conditioned media test sample is injected intradermally onto the backs of the test animals with 100 µl per injection site. It is possible to have about 10-30, preferably about 16-24, injection sites per animal. One µl of Evans blue dye (1% in physiologic buffered saline) is injected intracardially. Blemishes at the injection sites are then measured (mm diameter) at 1 hr and 6 hr post injection. Animals were sacrificed at 6 hrs after injection. Each skin injection site is biopsied and fixed in formalin. The skins are then prepared for histopathologic evaluation. Each site is evaluated for inflammatory cell infiltration into the skin. Sites with visible inflammatory cell inflammation are scored as positive. Inflammatory cells may be neutrophilic, eosinophilic, monocytic or lymphocytic. At least a minimal perivascular infiltrate at the injection site is scored as positive, no infiltrate at the site of injection is scored as negative.

The following polypeptides tested positive in this assay: PRO245, PRO217, PRO326, PRO266, PRO272, PRO301, PRO331 and PRO335.

Example 19

Detection of Polypeptides That Affect Glucose and/or FFA Uptake in Skeletal Muscle (Assay 106)

This assay is designed to determine whether PRO polypeptides show the ability to affect glucose or FFA uptake by skeletal muscle cells. PRO polypeptides testing positive in this assay would be expected to be useful for the therapeutic treatment of disorders where either the stimulation or inhibition of glucose uptake by skeletal muscle would be beneficial including, for example, diabetes or hyper- or hypo-insulinemia.

In a 96 well format, PRO polypeptides to be assayed are added to primary rat differentiated skeletal muscle, and allowed to incubate overnight. Then fresh media with the PRO polypeptide and +/− insulin are added to the wells. The sample media is then monitored to determine glucose and FFA uptake by the skeletal muscle cells. The insulin will stimulate glucose and FFA uptake by the skeletal muscle, and insulin in media without the PRO polypeptide is used as a positive control, and a limit for scoring. As the PRO polypeptide being tested may either stimulate or inhibit glucose and FFA uptake, results are scored as positive in the assay if greater than 1.5 times or less than 0.5 times the insulin control.

The following PRO polypeptides tested positive as either stimulators or inhibitors of glucose and/or FFA uptake in this assay: PRO187, PRO211.

Example 20

In Vitro Antitumor Assay (Assay 161)

The antiproliferative activity of various PRO polypeptides was determined in the investigational, disease-oriented in vitro anti-cancer drug discovery assay of the National Cancer Institute (NCI), using a sulforhodamine B (SRB) dye binding assay essentially as described by Skehan et al., *J. Natl. Cancer Inst.* 82:1107-1112 (1990). The 60 tumor cell lines employed in this study ("the NCI panel"), as well as conditions for their maintenance and culture in vitro have been described by Monks et al., *J. Natl. Cancer Inst.* 83:757-766 (1991). The purpose of this screen is to initially evaluate the cytotoxic and/or cytostatic activity of the test compounds against different types of tumors (Monks et al., supra; Boyd, *Cancer: Princ. Pract. Oncol. Update* 3(10):1-12 [1989]).

Cells from approximately 60 human tumor cell lines were harvested with trypsin/EDTA (Gibco), washed once, resuspended in IMEM and their viability was determined. The cell suspensions were added by pipet (100 µL volume) into separate 96-well microtiter plates. The cell density for the 6-day incubation was less than for the 2-day incubation to prevent overgrowth. Inoculates were allowed a preincubation period of 24 hours at 37° C. for stabilization. Dilutions at twice the intended test concentration were added at time zero in 100 µL aliquots to the microtiter plate wells (1:2 dilution). Test compounds were evaluated at five half-log dilutions (1000 to 100,000-fold). Incubations took place for two days and six days in a 5% $CO_2$ atmosphere and 100% humidity.

After incubation, the medium was removed and the cells were fixed in 0.1 ml of 10% trichloroacetic acid at 40° C. The plates were rinsed five times with deionized water, dried, stained for 30 minutes with 0.1 ml of 0.4% sulforhodamine B dye (Sigma) dissolved in 1% acetic acid, rinsed four times with 1% acetic acid to remove unbound dye, dried, and the stain was extracted for five minutes with 0.1 ml of 10 mM Tris base [tris(hydroxymethyl)aminomethane], pH 10.5. The absorbance (OD) of sulforhodamine B at 492 nm was measured using a computer-interfaced, 96-well microtiter plate reader.

A test sample is considered positive if it shows at least 50% growth inhibitory effect at one or more concentrations. PRO polypeptides testing positive in this assay are shown in Table 7, where the abbreviations are as follows:
  NSCL=non-small cell lung carcinoma
  CNS=central nervous system

TABLE 7

| Test compound | Tumor Cell Line Type | Cell Line Designation |
|---|---|---|
| PRO211 | NSCL | HOP62 |
| PRO211 | Leukemia | RPMI-8226 |
| PRO211 | Leukemia | HL-60 (TB) |
| PRO211 | NSCL | NCI-H522 |
| PRO211 | CNS | SF-539 |
| PRO211 | Melanoma | LOX IMVI |
| PRO211 | Breast | MDA-MB-435 |
| PRO211 | Leukemia | MOLT-4 |
| PRO211 | CNS | U251 |
| PRO211 | Breast | MCF7 |
| PRO211 | Leukemia | HT-60 (TB) |
| PRO211 | Leukemia | MOLT-4 |
| PRO211 | NSCL | EKVX |
| PRO211 | NSCL | NCI-H23 |
| PRO211 | NSCL | NCI-H322M |
| PRO211 | NSCL | NCI-H460 |
| PRO211 | Colon | HCT-116 |
| PRO211 | Colon | HT29 |
| PRO211 | CNS | SF-268 |
| PRO211 | CNS | SF-295 |
| PRO211 | CNS | SNB-19 |
| PRO211 | CNS | U251 |
| PRO211 | Melanoma | LOX IMVI |
| PRO211 | Melanoma | SK-MEL-5 |
| PRO211 | Melanoma | UACC-257 |
| PRO211 | Melanoma | UACC-62 |
| PRO211 | Ovarian | OVCAR-8 |
| PRO211 | Renal | RXF 393 |
| PRO211 | Breast | MCF7 |
| PRO211 | Breast | NCI/ADR-REHS 578T |
| PRO211 | Breast | T-47D |
| PRO211 | Leukemia | HL-60 (TB) |
| PRO211 | Leukemia | SR |
| PRO211 | NSCL | NCI-H23 |
| PRO211 | Colon | HCT-116 |
| PRO211 | Melanoma | LOX-IMVI |
| PRO211 | Melanoma | SK-MEL-5 |
| PRO211 | Breast | T-47D |
| PRO228 | Leukemia | MOLT-4 |
| PRO228 | NSCL | EKVX |
| PRO228 | Colon | KM12 |
| PRO228 | Melanoma | UACC-62 |
| PRO228 | Ovarian | OVCAR-3 |
| PRO228 | Renal | TK10 |
| PRO228 | Renal | SN12C |
| PRO228 | Breast | MCF7 |
| PRO228 | Leukemia | CCRF-CEM |
| PRO228 | Leukemia | HL-60 (TB) |
| PRO228 | Colon | COLO 205 |
| PRO228 | Colon | HCT-15 |
| PRO228 | Colon | KM12 |
| PRO228 | CNS | SF-268 |
| PRO228 | CNS | SNB-75 |
| PRO228 | Melanoma | LOX-IMVI |
| PRO228 | Melanoma | SK-MEL2 |
| PRO228 | Melanoma | UACC-257 |
| PRO228 | Ovarian | IGROV1 |
| PRO228 | Ovarian | OVCAR-4 |
| PRO228 | Ovarian | OVCAR-5 |
| PRO228 | Ovarian | OVCAR-8 |
| PRO228 | Renal | 786-0 |
| PRO228 | Renal | CAKI-1 |
| PRO228 | Renal | RXF 393 |
| PRO228 | Renal | TK-10 |
| PRO228 | Renal | UO-31 |
| PRO228 | Prostate | PC-3 |
| PRO228 | Prostate | DU-145 |
| PRO228 | Breast | MCF7 |
| PRO228 | Breast | NCI/ADR-REHS 578T |
| PRO228 | Breast | MDA-MB-435MDA-N |
| PRO228 | Breast | T-47D |
| PRO219 | Leukemia | SR |
| PRO219 | NSCL | NCI-H5222 |
| PRO219 | Breast | MCF7 |
| PRO219 | Leukemia | K-562; RPMI-8226 |
| PRO219 | NSCL | HOP-62; NCI-H322M |
| PRO219 | NSCL | NCI-H460 |
| PRO219 | Colon | HT29; KM12; HCT-116 |
| PRO219 | CNS | SF-539; U251 |
| PRO219 | Prostate | DU-145 |
| PRO219 | Breast | MDA-N |
| PRO219 | Ovarian | IGROV1 |
| PRO219 | NSCL | NCI-H226 |
| PRO219 | Leukemia | MOLT-4 |
| PRO219 | NSCL | A549/ATCC; EKVX; NCI-H23 |
| PRO219 | Colon | HCC-2998 |
| PRO219 | CNS | SF-295; SNB-19 |
| PRO219 | Melanoma | SK-MEL-2; SK-MEL-5 |
| PRO219 | Melanoma | UACC-257; UACC-62 |
| PRO219 | Ovarian | OCAR-4; SK-OV-3 |
| PRO219 | Renal | 786-0; ACHN; CAKI-1; SN12C |
| PRO219 | Renal | TK-10; UO-31 |
| PRO219 | Breast | NCI/ADR-RES; BT-549; T-47D |
| PRO219 | Breast | MDA-MB-435 |
| PRO221 | Leukemia | CCRF-CEM |

TABLE 7-continued

| Test compound | Tumor Cell Line Type | Cell Line Designation |
|---|---|---|
| PRO221 | Leukemia | MOLT-4 |
| PRO221 | NSCL | HOP-62 |
| PRO221 | Breast | MDA-N |
| PRO221 | Leukemia | RPMI-8226; SR |
| PRO221 | NSCL | NCI-H460 |
| PRO221 | Colon | HCC-2998 |
| PRO221 | Ovarian | IGROV1 |
| PRO221 | Renal | TK-10 |
| PRO221 | Breast | MCF7 |
| PRO221 | Leukemia | K-562 |
| PRO221 | Breast | MDA-MB-435 |
| PRO224 | Ovarian | OVCAR-4 |
| PRO224 | Renal | RXF 393 |
| PRO224 | Prostate | DU-145 |
| PRO224 | NSCL | HOP-62; NCI-H322M |
| PRO224 | Melanoma | LOX IMVI |
| PRO224 | Ovarian | OVCAR-8 |
| PRO224 | Leukemia | SR |
| PRO224 | NSCL | NCI-H460 |
| PRO224 | CNS | SF-295 |
| PRO224 | Leukemia | RPMI-8226 |
| PRO224 | Breast | BT-549 |
| PRO224 | Leukemia | CCRF-CEM; LH-60 (TB) |
| PRO224 | Colon | HCT-116 |
| PRO224 | Breast | MDA-MB-435 |
| PRO224 | Leukemia | HL-60 (TB) |
| PRO224 | Colon | HCC-2998 |
| PRO224 | Prostate | PC-3 |
| PRO224 | CNS | U251 |
| PRO224 | Colon | HCT-15 |
| PRO224 | CNS | SF-539 |
| PRO224 | Renal | ACHN |
| PRO328 | Leukemia | RPMI-8226 |
| PRO328 | NSCL | A549/ATCC; EKVX; HOP-62 |
| PRO328 | NSCL | NCI-H23; NCI-H322M |
| PRO328 | Colon | HCT-15; KM12 |
| PRO328 | CNS | SF-295; SF-539; SNB-19; U251 |
| PRO328 | Melanoma | M14; UACC-257; UCAA-62 |
| PRO328 | Renal | 786-0; ACHN |
| PRO328 | Breast | MCF7 |
| PRO328 | Leukemia | SR |
| PRO328 | Colon | NCI-H23 |
| PRO328 | Melanoma | SK-MEL-5 |
| PRO328 | Prostate | DU-145 |
| PRO328 | Melanoma | LOX IMVI |
| PRO328 | Breast | MDA-MB-435 |
| PRO328 | Ovarian | OVCAR-3 |
| PRO328 | Breast | T-47D |
| PRO301 | NSCL | NCI-H322M |
| PRO301 | Leukemia | MOLT-4; SR |
| PRO301 | NSCL | A549/ATCC; EKVX; |
| PRO301 | NSCL | NCI-H23; NCI-460; NCI-H226 |
| PRO301 | Colon | COLO 205; HCC-2998; |
| PRO301 | Colon | HCT-15; KM12; HT29; |
| PRO301 | Colon | HCT-116 |
| PRO301 | CNS | SF-268; SF-295; SNB-19 |
| PRO301 | Melanoma | MALME-3M; SK-MEL-2; |
| PRO301 | Melanoma | SK-MEL-5; UACC-257 |
| PRO301 | Melanoma | UACC-62 |
| PRO301 | Ovarian | IGROV1; OVCAR-4 |
| PRO301 | Ovarian | OVCAR-5 |
| PRO301 | Ovarian | OVCAR-8; SK0OV-3 |
| PRO301 | Renal | ACHN; CAKI-1; TK-10; UO-31 |
| PRO301 | Prostate | PC-3; DU-145 |
| PRO301 | Breast | NCI/ADR-RES; HS 578T |
| PRO301 | Breast | MDA-MB-435; MDA-N; T-47D |
| PRO301 | Melanoma | M14 |
| PRO301 | Leukemia | CCRF-CEM; HL-60(TB); K-562 |
| PRO301 | Leukemia | RPMI-8226 |
| PRO301 | Melanoma | LOX IMVI |
| PRO301 | Renal | 786-0; SN12C |
| PRO301 | Breast | MCF7; MDA-MB-231/ATCC |
| PRO301 | Breast | BT-549 |
| PRO301 | NSCL | HOP-62 |
| PRO301 | CNS | SF-539 |
| PRO301 | Ovarian | OVCAR-3 |
| PRO326 | NSCL | NCI-H322M |
| PRO326 | CNS | SF295 |
| PRO326 | CNS | ST539 |
| PRO326 | CNS | U251 |

The results of these assays demonstrate that the positive testing PRO polypeptides are useful for inhibiting neoplastic growth in a number of different tumor cell types and may be used therapeutically therefor. Antibodies against these PRO polypeptides are useful for affinity purification of these useful polypeptides. Nucleic acids encoding these PRO polypeptides are useful for the recombinant preparation of these polypeptides.

Example 21

Gene Amplification

This example shows that certain PRO polypeptide-encoding genes are amplified in the genome of certain human lung, colon and/or breast cancers and/or cell lines. Amplification is associated with overexpression of the gene product, indicating that the polypeptides are useful targets for therapeutic intervention in certain cancers such as colon, lung, breast and other cancers and diagnostic determination of the presence of those cancers. Therapeutic agents may take the form of antagonists of the PRO polypeptide, for example, murine-human chimeric, humanized or human antibodies against a PRO polypeptide.

The starting material for the screen was genomic DNA isolated from a variety cancers. The DNA is quantitated precisely, e.g., fluorometrically. As a negative control, DNA was isolated from the cells of ten normal healthy individuals which was pooled and used as assay controls for the gene copy in healthy individuals (not shown). The 5' nuclease assay (for example, TAQMAN™) and real-time quantitative PCR (for example, ABI PRIZM 7700 SEQUENCE DETECTION SYSTEM™ (Perkin Elmer, Applied Biosystems Division, Foster City, Calif.)), were used to find genes potentially amplified in certain cancers. The results were used to determine whether the DNA encoding the PRO polypeptide is over-represented in any of the primary lung or colon cancers or cancer cell lines or breast cancer cell lines that were screened. The primary lung cancers were obtained from individuals with tumors of the type and stage as indicated in Table 8. An explanation of the abbreviations used for the designation of the primary tumors listed in Table 8 and the primary tumors and cell lines referred to throughout this example are given below.

The results of the TAQMAN™ are reported in delta (Δ) Ct units. One unit corresponds to 1 PCR cycle or approximately a 2-fold amplification relative to normal, two units corresponds to 4-fold, 3 units to 8-fold amplification and so on. Quantitation was obtained using primers and a TAQMAN™ fluorescent probe derived from the PRO polypeptide-encoding gene. Regions of the PRO polypeptide-encoding gene which are most likely to contain unique nucleic acid sequences and which are least likely to have spliced out introns are preferred for the primer and probe derivation, e.g., 3'-untranslated regions. The sequences for the primers and probes (forward, reverse and probe) used for the PRO polypeptide gene amplification analysis were as follows:

```
PRO211 (DNA32292-1131):

32292.3utr-5:
5'-CAGAAGGATGTCCCGTGGAA-3'        (SEQ ID NO:11)

32292.3utr-3:
5'-GCCGCTGTCCACTGCAG-3'           (SEQ ID NO:12)

32292.3utr-probe.rc:
5'-GACGGCATCCTCAGGGCCACA-3'       (SEQ ID NO:13)
```

The 5' nuclease assay reaction is a fluorescent PCR-based technique which makes use of the 5' exonuclease activity of Taq DNA polymerase enzyme to monitor amplification in real time. Two oligonucleotide primers (forward [.f] and reverse [.r]) are used to generate an amplicon typical of a PCR reaction. A third oligonucleotide, or probe (.p), is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the ABI PRISM 7700™ SEQUENCE DETECTION™. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5' Nuclease assay data are initially expressed as Ct, or the threshold cycle. This is defined as the cycle at which the reporter signal accumulates above the background level of fluorescence. The ΔCt values are used as quantitative measurement of the relative number of starting copies of a particular target sequence in a nucleic acid sample when comparing cancer DNA results to normal human DNA results.

Table 8 describes the stage, T stage and N stage of various primary tumors which were used to screen the PRO polypeptide compounds of the invention.

TABLE 8

Primary Lung and Colon Tumor Profiles

| Primary Tumor Stage | Stage | Other Stage | Dukes Stage | T Stage | N Stage |
|---|---|---|---|---|---|
| Human lung tumor AdenoCa (SRCC724) [LT1] | IIA | | | T1 | N1 |
| Human lung tumor SqCCa (SRCC725) [LT1a] | IIB | | | T3 | N0 |
| Human lung tumor AdenoCa (SRCC726) [LT2] | IB | | | T2 | N0 |
| Human lung tumor AdenoCa (SRCC727) [LT3] | IIIA | | | T1 | N2 |
| Human lung tumor AdenoCa (SRCC728) [LT4] | IB | | | T2 | N0 |
| Human lung tumor SqCCa (SRCC729) [LT6] | IB | | | T2 | N0 |
| Human lung tumor Aden/SqCCa (SRCC730) [LT7] | IA | | | T1 | N0 |
| Human lung tumor AdenoCa (SRCC731) [LT9] | IB | | | T2 | N0 |
| Human lung tumor SqCCa (SRCC732) [LT10] | IIB | | | T2 | N1 |
| Human lung tumor SqCCa (SRCC733) [LT11] | IIA | | | T1 | N1 |
| Human lung tumor AdenoCa (SRCC734) [LT12] | IV | | | T2 | N0 |
| Human lung tumor AdenoSqCCa (SRCC735) [LT13] | IB | | | T2 | N0 |
| Human lung tumor SqCCa (SRCC736) [LT15] | IB | | | T2 | N0 |
| Human lung tumor SqCCa (SRCC737) [LT16] | IB | | | T2 | N0 |
| Human lung tumor SqCCa (SRCC738) [LT17] | IIB | | | T2 | N1 |
| Human lung tumor SqCCa (SRCC739) [LT18] | IB | | | T2 | N0 |
| Human lung tumor SqCCa (SRCC740) [LT19] | IB | | | T2 | N0 |
| Human lung tumor LCCa (SRCC741) [LT21] | IIB | | | T3 | N1 |
| Human lung AdenoCa (SRCC811) [LT22] | 1A | | | T1 | N0 |
| Human colon AdenoCa (SRCC742) [CT2] | | M1 | D | pT4 | N0 |
| Human colon AdenoCa (SRCC743) [CT3] | | | B | pT3 | N0 |
| Human colon AdenoCa (SRCC744) [CT8] | | | B | T3 | N0 |
| Human colon AdenoCa (SRCC745) [CT10] | | | A | pT2 | N0 |
| Human colon AdenoCa (SRCC746) [CT12] | | MO, R1 | B | T3 | N0 |
| Human colon AdenoCa (SRCC747) [CT14] | | pMO, RO | B | pT3 | pN0 |
| Human colon AdenoCa (SRCC748) [CT15] | | M1, R2 | D | T4 | N2 |
| Human colon AdenoCa (SRCC749) [CT16] | | pMO | B | pT3 | pN0 |
| Human colon AdenoCa (SRCC750) [CT17] | | | C1 | pT3 | pN1 |
| Human colon AdenoCa (SRCC751) [CT1] | | MO, R1 | B | pT3 | N0 |
| Human colon AdenoCa (SRCC752) [CT4] | | | B | pT3 | M0 |
| Human colon AdenoCa (SRCC753) [CT5] | | G2 | C1 | pT3 | pN0 |
| Human colon AdenoCa (SRCC754) [CT6] | | pMO, RO | B | pT3 | pN0 |
| Human colon AdenoCa (SRCC755) [CT7] | | G1 | A | pT2 | pN0 |
| Human colon AdenoCa (SRCC756) [CT9] | | G3 | D | pT4 | pN2 |
| Human colon AdenoCa (SRCC757) [CT11] | | | B | T3 | N0 |
| Human colon AdenoCa (SRCC758) [CT18] | | MO, RO | B | pT3 | pN0 |

DNA Preparation:

DNA was prepared from cultured cell lines, primary tumors, normal human blood. The isolation was performed using purification kit, buffer set and protease and all from Quiagen, according to the manufacturer's instructions and the description below.

Cell Culture Lysis:

Cells were washed and trypsinized at a concentration of $7.5 \times 10^8$ per tip and pelleted by centrifuging at 1000 rpm for 5 minutes at 4° C., followed by washing again with ½ volume of PBS recentrifugation. The pellets were washed a third time, the suspended cells collected and washed 2× with PBS. The cells were then suspended into 10 ml PBS. Buffer C1 was equilibrated at 4° C. Qiagen protease #19155 was diluted into 6.25 ml cold ddH$_2$0 to a final concentration of 20 mg/ml and equilibrated at 4° C. 10 ml of G2 Buffer was prepared by diluting Qiagen RNAse A stock (100 mg/ml) to a final concentration of 200 µg/ml.

Buffer C1 (10 ml, 4° C.) and ddH2O (40 ml, 4° C.) were then added to the 10 ml of cell suspension, mixed by inverting and incubated on ice for 10 minutes. The cell nuclei were pelleted by centrifuging in a Beckman swinging bucket rotor at 2500 rpm at 4° C. for 15 minutes. The supernatant was discarded and the nuclei were suspended with a vortex into 2 ml Buffer C1 (at 4° C.) and 6 ml ddH$_2$O, followed by a second 4° C. centrifugation at 2500 rpm for 15 minutes. The nuclei were then resuspended into the residual buffer using 200 µl per tip. G2 buffer (10 ml) was added to the suspended nuclei while gentle vortexing was applied. Upon completion of buffer addition, vigorous vortexing was applied for 30 seconds. Quiagen protease (200 µl, prepared as indicated above) was added and incubated at 50° C. for 60 minutes. The incubation and centrifugation was repeated until the lysates were clear (e.g., incubating additional 30-60 minutes, pelleting at 3000×g for 10 min., 4° C.).

Solid Human Tumor Sample Preparation and Lysis:

Tumor samples were weighed and placed into 50 ml conical tubes and held on ice. Processing was limited to no more than 250 mg tissue per preparation (1 tip/preparation). The protease solution was freshly prepared by diluting into 6.25 ml cold ddH$_2$O to a final concentration of 20 mg/ml and stored at 4° C. G2 buffer (20 ml) was prepared by diluting DNAse A to a final concentration of 200 mg/ml (from 100 mg/ml stock). The tumor tissue was homogenated in 19 ml G2 buffer for 60 seconds using the large tip of the polytron in a laminar-flow TC hood in order to avoid inhalation of aerosols, and held at room temperature. Between samples, the polytron was cleaned by spinning at 2×30 seconds each in 2 L ddH$_2$0, followed by G2 buffer (50 ml). If tissue was still present on the generator tip, the apparatus was disassembled and cleaned.

Quiagen protease (prepared as indicated above, 1.0 ml) was added, followed by vortexing and incubation at 50° C. for 3 hours. The incubation and centrifugation was repeated until the lysates were clear (e.g., incubating additional 30-60 minutes, pelleting at 3000×g for 10 min., 4° C.).

Human Blood Preparation and Lysis:

Blood was drawn from healthy volunteers using standard infectious agent protocols and citrated into 10 ml samples per tip. Quiagen protease was freshly prepared by dilution into 6.25 ml cold ddH$_2$O to a final concentration of 20 mg/ml and stored at 4° C. G2 buffer was prepared by diluting RNAse A to a final concentration of 200 µg/ml from 100 mg/ml stock. The blood (10 ml) was placed into a 50 ml conical tube and 10 ml C1 buffer and 30 ml ddH$_2$O (both previously equilibrated to 4° C.) were added, and the components mixed by inverting and held on ice for 10 minutes. The nuclei were pelleted with a Beckman swinging bucket rotor at 2500 rpm, 4° C. for 15 minutes and the supernatant discarded. With a vortex, the nuclei were suspended into 2 ml C1 buffer (4° C.) and 6 ml ddH$_2$O (4° C.). Vortexing was repeated until the pellet was white. The nuclei were then suspended into the residual buffer using a 200 µl tip. G2 buffer (10 ml) were added to the suspended nuclei while gently vortexing, followed by vigorous vortexing for 30 seconds. Quiagen protease was added (200 µl) and incubated at 50° C. for 60 minutes. The incubation and centrifugation was repeated until the lysates were clear (e.g., incubating additional 30-60 minutes, pelleting at 3000×g for 10 min., 4° C.).

Purification of Cleared Lysates:

(1) Isolation of Genomic DNA:

Genomic DNA was equilibrated (1 sample per maxi tip preparation) with 10 ml QBT buffer. QF elution buffer was equilibrated at 50° C. The samples were vortexed for 30 seconds, then loaded onto equilibrated tips and drained by gravity. The tips were washed with 2×15 ml QC buffer. The DNA was eluted into 30 ml silanized, autoclaved 30 ml Corex tubes with 15 ml QF buffer (50° C.). Isopropanol (10.5 ml) was added to each sample, the tubes covered with parafin and mixed by repeated inversion until the DNA precipitated. Samples were pelleted by centrifugation in the SS-34 rotor at 15,000 rpm for 10 minutes at 4° C. The pellet location was marked, the supernatant discarded, and 10 ml 70% ethanol (4° C.) was added. Samples were pelleted again by centrifugation on the SS-34 rotor at 10,000 rpm for 10 minutes at 4° C. The pellet location was marked and the supernatant discarded. The tubes were then placed on their side in a drying rack and dried 10 minutes at 37° C., taking care not to overdry the samples.

After drying, the pellets were dissolved into 1.0 ml TE (pH 8.5) and placed at 50° C. for 1-2 hours. Samples were held overnight at 4° C. as dissolution continued. The DNA solution was then transferred to 1.5 ml tubes with a 26 gauge needle on a tuberculin syringe. The transfer was repeated 5× in order to shear the DNA. Samples were then placed at 50° C. for 1-2 hours.

(2) Quantitation of Genomic DNA and Preparation for Gene Amplification Assay:

The DNA levels in each tube were quantified by standard $A_{260}$, $A_{280}$ spectrophotometry on a 1:20 dilution (5 µl DNA+ 95 µl ddH$_2$O) using the 0.1 ml quartz cuvetts in the Beckman DU640 spectrophotometer. $A_{260}/A_{280}$ ratios were in the range of 1.8-1.9. Each DNA samples was then diluted further to approximately 200 ng/ml in TE (pH 8.5). If the original material was highly concentrated (about 700 ng/µl), the material was placed at 50° C. for several hours until resuspended.

Fluorometric DNA quantitation was then performed on the diluted material (20-600 ng/ml) using the manufacturer's guidelines as modified below. This was accomplished by allowing a Hoeffer DyNA Quant 200 fluorometer to warm-up for about 15 minutes. The Hoechst dye working solution (#H33258, 10 µl, prepared within 12 hours of use) was diluted into 100 ml 1×TNE buffer. A 2 ml cuvette was filled with the fluorometer solution, placed into the machine, and the machine was zeroed. pGEM 3Zf(+) (2 µl, lot #360851026) was added to 2 ml of fluorometer solution and calibrated at 200 units. An additional 2 µl of pGEM 3Zf(+) DNA was then tested and the reading confirmed at 400+/−10 units. Each sample was then read at least in triplicate. When 3 samples were found to be within 10% of each other, their average was taken and this value was used as the quantification value.

The fluorometricly determined concentration was then used to dilute each sample to 10 ng/µl in ddH$_2$O. This was done simultaneously on all template samples for a single TAQMAN™ plate assay, and with enough material to run 500-1000 assays. The samples were tested in triplicate with TAQMAN™ primers and probe both B-actin and GAPDH on a single plate with normal human DNA and no-template controls. The diluted samples were used provided that the CT value of normal human DNA subtracted from test DNA was +/−1 Ct. The diluted, lot-qualified genomic DNA was stored in 1.0 ml aliquots at −80° C. Aliquots which were subsequently to be used in the gene amplification assay were stored at 4° C. Each 1 ml aliquot is enough for 8-9 plates or 64 tests.

Gene Amplification Assay:

The PRO polypeptide compounds of the invention were screened in the following primary tumors and the resulting ΔCt values greater than or equal to 1.0 are reported in Table 9 below.

TABLE 9

ΔCt values in lung and colon primary tumors and cell line models

| Primary Tumors or Cell lines | PRO187 | PRO533 | PRO214 | PRO343 | PRO211 | PRO230 | PRO246 | PRO317 | PRO232 | PRO269 | PRO304 | PRO-339 |
|---|---|---|---|---|---|---|---|---|---|---|---|---|
| LT7 |  |  |  |  |  |  |  | 1.52 |  | 1.04 |  | 1.08 |
| LT13 | 2.74 |  | 1.85 | 2.71 | 1.88 | 3.42 | 1.63 | 1.90 |  | 1.27 | 1.29 | 1.04 |
|  | 2.98 |  | 1.83 | 2.23 | 2.26 | 3.22 | 1.68 | 2.24 |  |  |  |  |
|  | 2.44 |  |  |  |  | 2.84 |  | 2.93 |  |  |  |  |
|  |  |  |  |  |  | 2.15 |  |  |  |  |  |  |
|  |  |  |  |  |  | 2.75 |  |  |  |  |  |  |
|  |  |  |  |  |  | 2.53 |  |  |  |  |  |  |
|  |  |  |  |  |  | 1.82 |  |  |  |  |  |  |
| LT3 |  |  | 1.57 |  | 1.97 |  | 1.06 | 1.86 |  |  |  | 1.17 |
| LT4 |  |  |  |  | 1.17 |  |  | 1.18 |  |  |  |  |
| LT9 |  |  |  |  | 1.42 |  |  | 1.04 |  | 1.80 |  | 1.03 |
| LT12 | 2.70 |  | 1.38 | 2.23 | 1.51 | 2.86 | 1.54 | 2.54 | 2.40 | 1.14 | 1.15 | 1.26 |
|  | 2.90 |  | 1.49 | 1.50 | 1.27 | 2.96 | 2.47 | 1.74 |  |  |  |  |
|  | 2.27 |  |  |  |  | 2.92 |  |  |  |  |  |  |
|  |  |  |  |  |  | 1.25 |  |  |  |  |  |  |
|  |  |  |  |  |  | 2.68 |  |  |  |  |  |  |
|  |  |  |  |  |  | 2.28 |  |  |  |  |  |  |
|  |  |  |  |  |  | 1.34 |  |  |  |  |  |  |
| LT30 | 1.67 |  |  |  |  | 2.13 |  |  |  |  |  |  |
|  |  |  |  |  |  | 1.36 |  |  |  |  |  |  |
| LT21 |  |  |  |  | 1.26 | 1.09 | 1.50 |  |  |  |  |  |
| LT1-a |  | 1.02 |  |  | 1.18 |  |  | 1.29 |  |  |  |  |
| LT6 |  |  |  |  |  |  |  | 1.93 |  |  |  |  |
| LT10 |  |  |  |  | 1.96 |  | 1.07 | 2.57 |  |  |  |  |
| LT11 |  | 1.09 | 1.67 | 1.00 | 2.05 | 1.32 | 3.43 | 2.20 |  | 1.14 | 1.51 | 1.39 |
|  |  |  | 1.80 |  | 1.89 | 1.14 | 1.41 | 2.33 |  |  |  |  |
|  |  |  |  |  |  | 1.54 |  | 1.02 |  |  |  |  |
| LT15 | 3.75 |  | 1.77 | 3.62 | 2.44 | 4.32 | 2.11 | 2.06 | 1.86 | 1.36 | 1.34 |  |
|  | 3.92 |  | 1.58 | 1.30 | 2.16 | 4.47 | 1.56 | 2.76 |  |  |  |  |
|  | 3.49 |  |  |  |  | 3.64 |  | 1.63 |  |  |  |  |
|  |  |  |  |  |  | 2.94 |  |  |  |  |  |  |
|  |  |  |  |  |  | 3.56 |  |  |  |  |  |  |
|  |  |  |  |  |  | 3.32 |  |  |  |  |  |  |
|  |  |  |  |  |  | 2.68 |  |  |  |  |  |  |
| LT16 | 2.10 | 1.66 |  | 1.70 | 1.25 | 1.15 |  | 1.55 |  |  | 1.00 |  |
|  |  |  |  |  |  | 2.04 |  | 1.08 |  |  |  |  |
|  |  |  |  |  |  | 1.83 |  | 1.33 |  |  |  |  |
| LT17 |  | 1.32 | 1.93 | 1.15 | 1.85 | 1.26 | 2.68 | 2.29 | 1.35 | 1.42 | 1.68 | 1.63 |
|  |  |  | 1.87 |  | 2.30 | 1.39 | 1.69 | 2.03 |  |  |  |  |
|  |  |  |  |  |  | 1.30 |  | 1.10 |  |  |  |  |
|  |  |  |  |  |  | 1.33 |  |  |  |  |  |  |
|  |  |  |  |  |  | 1.30 |  |  |  |  |  |  |
| LT18 |  |  |  |  | 1.17 |  |  |  | 1.04 |  |  |  |
| LT19 | 4.05 | 1.67 | 2.09 | 3.82 | 2.42 | 4.05 | 1.91 | 2.51 | 1.21 | 1.60 | 1.15 |  |
|  | 3.99 |  | 1.98 |  | 2.55 | 4.92 | 1.68 | 2.03 |  |  |  |  |
|  |  |  |  |  |  | 4.93 | 1.16 |  |  |  |  |  |
|  |  |  |  |  |  | 3.78 |  |  |  |  |  |  |
|  |  |  |  |  |  | 4.76 |  |  |  |  |  |  |
| HF-000840 |  |  |  |  |  | 1.58 |  |  |  |  |  |  |
| Calu-1 |  |  |  |  |  | 1.08 |  |  |  |  |  |  |
| SW900 |  |  |  |  | 1.86 |  |  |  |  |  |  |  |
| CT2 | 3.56 |  | 2.49 | 1.95 | 1.42 |  |  | 2.75 |  |  |  |  |
|  |  |  |  | 3.49 |  |  |  | 2.36 |  |  |  |  |
| CT3 |  |  | 2.06 | 1.15 |  | 1.34 |  |  |  |  |  |  |
| CT8 | 1.01 |  | 1.48 | 1.29 |  |  |  |  |  |  |  |  |
|  |  |  |  | 1.58 |  |  |  |  |  |  |  |  |
| CT10 | 1.81 |  | 1.84 | 1.88 |  | 1.00 |  | 1.88 |  |  |  |  |
|  |  |  |  | 1.49 |  |  |  | 1.55 |  |  |  |  |
| CT12 |  |  | 1.81 | 1.74 |  | 1.13 |  |  |  |  |  |  |

TABLE 9-continued

ΔCt values in lung and colon primary tumors and cell line models

| Primary Tumors or Cell lines | PRO187 | PRO533 | PRO214 | PRO343 | PRO211 | PRO230 | PRO246 | PRO317 | PRO232 | PRO269 | PRO304 | PRO339 |
|---|---|---|---|---|---|---|---|---|---|---|---|---|
| CT14 | 1.82 |  | 2.48 | 2.33 |  |  |  | 1.36 |  |  |  |  |
|  |  |  |  | 1.72 |  |  |  | 1.24 |  |  |  |  |
| CT15 |  |  | 1.63 | 2.06 |  |  |  | 1.33 |  |  |  |  |
|  |  |  |  | 1.41 |  |  |  | 1.04 |  |  |  |  |
| CT16 |  |  | 1.95 | 1.78 |  | 1.40 |  |  |  |  |  |  |
| CT17 |  |  | 2.04 | 2.40 |  | 1.74 |  |  |  |  |  |  |
| CT1 | 1.24 |  | 1.22 |  | 1.27 | 1.25 |  |  | 2.41 |  |  |  |
|  | 1.34 |  | 1.46 |  | 1.14 |  |  |  |  |  |  |  |
| CT4 |  |  | 1.36 | 1.77 | 1.33 | 1.32 | 1.10 | 1.17 | 2.05 |  |  |  |
|  |  |  | 1.42 |  | 1.02 |  |  |  |  |  |  |  |
| CT5 | 2.96 |  | 1.56 | 2.68 | 1.76 | 2.27 | 1.33 |  | 1.59 |  |  |  |
|  | 2.99 |  | 2.76 |  | 1.64 |  | 2.39 |  |  |  |  |  |
| CT6 | 1.10 |  | 1.33 |  | 1.01 |  |  |  |  |  |  |  |
|  |  |  |  |  | 1.14 |  |  |  |  |  |  |  |
| CT7 | 1.40 |  |  | 1.66 |  | 1.39 |  |  | 1.00 |  |  |  |
| CT9 | 1.39 |  | 1.16 |  |  |  | 1.09 | 1.24 | 1.13 |  |  |  |
| CT11 | 2.22 |  | 2.05 | 1.55 | 2.01 | 1.75 | 1.48 |  | 1.92 |  |  |  |
|  | 2.26 |  | 1.85 |  | 1.83 |  | 1.12 |  |  |  |  |  |
| HF000539 |  |  |  |  |  | 1.57 |  |  |  |  |  |  |
| SW620 |  |  |  |  |  | 1.14 |  |  |  |  |  |  |
| HF000611 |  |  |  |  |  | 4.64 |  |  |  |  |  |  |
| HF000733 |  |  |  |  |  | 1.93 |  |  |  |  |  |  |
|  |  |  |  |  |  | 2.33 |  |  |  |  |  |  |
| HF000716 |  |  |  |  |  | 1.68 |  |  |  |  |  |  |
|  |  |  |  |  |  | 2.82 |  |  |  |  |  |  |
| CT18 |  |  |  |  |  |  |  |  | 1.29 |  |  |  |

SUMMARY

Because amplification of the various DNA's as described above occurs in various tumors, it is likely associated with tumor formation and/or growth. As a result, antagonists (e.g., antibodies) directed against these polypeptides would be expected to be useful in cancer therapy.

Example 22

Tissue Expression Distribution

Oligonucleotide probes were constructed from some of the PRO polypeptide-encoding nucleotide sequences shown in the accompanying figures for use in quantitative PCR amplification reactions. The oligonucleotide probes were chosen so as to give an approximately 200-600 base pair amplified fragment from the 3' end of its associated template in a standard PCR reaction. The oligonucleotide probes were employed in standard quantitative PCR amplification reactions with cDNA libraries isolated from different human adult and/or fetal tissue sources and analyzed by agarose gel electrophoresis so as to obtain a quantitative determination of the level of expression of the PRO polypeptide-encoding nucleic acid in the various tissues tested. Knowledge of the expression pattern or the differential expression of the PRO polypeptide-encoding nucleic acid in various different human tissue types provides a diagnostic marker useful for tissue typing, with or without other tissue-specific markers, for determining the primary tissue source of a metastatic tumor, and the like. These assays provided the following results.

| DNA Molecule | Tissues With Significant Expression | Tissues Lacking Significant Expression |
|---|---|---|
| DNA34436-1238 | lung, placenta, brain | testis |
| DNA35557-1137 | lung, kidney, brain | placenta |
| DNA35599-1168 | kidney, brain | liver, placenta |
| DNA35668-1171 | liver, lung, kidney | placenta, brain |
| DNA36992-1168 | liver, lung, kidney, brain | placenta |
| DNA39423-1182 | kidney, brain | liver |
| DNA40603-1232 | liver | brain, kidney, lung |
| DNA40604-1187 | liver | brain, kidney, lung |
| DNA41379-1236 | lung, brain | liver |
| DNA33206-1165 | heart, spleen, dendrocytes | substantia nigra, hippocampus, cartilage, prostate, HUVEC |
| DNA34431-1177 | spleen, HUVEC, cartilage, heart, uterus | brain, colon tumor, prostate, THP-1 macrophages |
| DNA41225-1217 | HUVEC, uterus, colon tumor, cartilage, prostate | spleen, brain, heart, IM-9 lymphoblasts |

Example 23

In Situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, *Cell Vision* 1:169-176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A [$^{33}$-P] UTP-labeled antisense riboprobe was generated from a PCR product and hybridized at 55° C. overnight. The slides were dipped in Kodak NTB2 nuclear track emulsion and exposed for 4 weeks.

$^{33}$P-Riboprobe Synthesis 6.0 µl (125 mCi) of $^{33}$P-UTP (Amersham BF 1002, SA<2000 Ci/mmol) were speed vac dried. To each tube containing dried $^{33}$P-UTP, the following ingredients were added:
  2.0 µl 5× transcription buffer
  1.0 µl DTT (100 mM)
  2.0 µl NTP mix (2.5 mM: 10µ; each of 10 mM GTP, CTP & ATP+10 µl H$_2$O)
  1.0 µl UTP (50 µM)
  1.0 µl Rnasin
  1.0 µl DNA template (1 µg)
  1.0 µl H$_2$O
  1.0 µl RNA polymerase (for PCR products T3=AS, T7=S, usually)

The tubes were incubated at 37□C for one hour. 1.0 µl RQ1 DNase were added, followed by incubation at 37° C. for 15 minutes. 90 µl TE (10 mM Tris pH 7.6/1 mM EDTA pH 8.0) were added, and the mixture was pipetted onto DE81 paper. The remaining solution was loaded in a Microcon-50 ultra-filtration unit, and spun using program 10 (6 minutes). The filtration unit was inverted over a second tube and spun using program 2 (3 minutes). After the final recovery spin, 100 µl TE were added. 1 µl of the final product was pipetted on DE81 paper and counted in 6 ml of Biofluor II.

The probe was run on a TBE/urea gel. 1-3 µl of the probe or 5 µl of RNA Mrk III were added to 3 µl of loading buffer. After heating on a 95° C. heat block for three minutes, the gel was immediately placed on ice. The wells of gel were flushed, the sample loaded, and run at 180-250 volts for 45 minutes. The gel was wrapped in saran wrap and exposed to XAR film with an intensifying screen in −70° C. freezer one hour to overnight.

$^{33}$P-Hybridization

A. Pretreatment of Frozen Sections

The slides were removed from the freezer, placed on aluminium trays and thawed at room temperature for 5 minutes. The trays were placed in 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+ 975 ml SQ H$_2$O). After deproteination in 0.5 µg/ml proteinase K for 10 minutes at 37° C. (12.5 µl of 10 mg/ml stock in 250 ml prewarmed RNase-free RNAse buffer), the sections were washed in 0.5×SSC for 10 minutes at room temperature. The sections were dehydrated in 70%, 95%, 100% ethanol, 2 minutes each.

B. Pretreatment of Paraffin-embedded Sections

The slides were deparaffinized, placed in SQ H$_2$O, and rinsed twice in 2×SSC at room temperature, for 5 minutes each time. The sections were deproteinated in 20 µg/ml proteinase K (500 µl of 10 mg/ml in 250 ml RNase-free RNase buffer; 37° C., 15 minutes) human embryo, or 8× proteinase K (100 µl in 250 ml Rnase buffer, 37° C., 30 minutes)— formalin tissues. Subsequent rinsing in 0.5×SSC and dehydration were performed as described above.

C. Prehybridization

The slides were laid out in a plastic box lined with Box buffer (4×SSC, 50% formamide)-saturated filter paper. The tissue was covered with 50 µl of hybridization buffer (3.75 g Dextran Sulfate+6 ml SQ H$_2$O), vortexed and heated in the microwave for 2 minutes with the cap loosened. After cooling on ice, 18.75 ml formamide, 3.75 ml 20×SSC and 9 ml SQ H$_2$O were added, the tissue was vortexed well, and incubated at 42° C. for 1-4 hours.

D. Hybridization 1.0×10 cpm probe and 1.0 µl tRNA (50 mg/ml stock) per slide were heated at 95° C. for 3 minutes. The slides were cooled on ice, and 48 µl hybridization buffer were added per slide. After vortexing, 50 µl $^{33}$P mix were added to 50 µl prehybridization on slide. The slides were incubated overnight at 55° C.

E. Washes

Washing was done 2×10 minutes with 2×SSC, EDTA at room temperature (400 ml 20×SSC+16 ml 0.25M EDTA, V$_f$=4 L), followed by RNaseA treatment at 37° C. for 30 minutes (500 µl of 10 mg/ml in 250 ml Rnase buffer=20 µg/ml), The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, V$_f$=4 L).

F. Oligonucleotides

In situ analysis was performed on a variety of DNA sequences disclosed herein. The oligonucleotides employed for these analyses are as follows.

(1) DNA33094-1131 (PRO217)

```
                                            (SEQ ID NO:14)
p1 5'-GGATTCTAATACGACTCACTATAGGGCTCAGAAAAGCGCAACAG
AGAA-3'

(SEQ ID NO:15)
p2 5'-CTATGAAATTAACCCTCACTAAAGGGATGTCTTCCATGCCAACC
TTC-3'
```

G. Results

In situ analysis was performed on a variety of DNA sequences disclosed herein. The results from these analyses are as follows.

(1) DNA33094-1131 (PRO217)

Highly distinctive expression pattern, that does not indicate an obvious biological function. In the human embryo it was expressed in outer smooth muscle layer of the GI tract, respiratiry cartilage, branching respiratory epithelium, osteoblasts, tendons, gonad, in the optic nerve head and developing dermis. In the adult expression was observed in the epidermal pegs of the chimp tongue, the basal epithelial/myoepithelial cells of the prostate and urinary bladder. Also expressed in the alveolar lining cells of the adult lung, mesenchymal cells juxtaposed to erectile tissue in the penis and the cerebral cortex (probably glial cells). In the kidney, expression was only seen in disease, in cells surrounding thyroidized renal tubules.

Human fetal tissues examined (E12-E16 weeks) include: Placenta, umbilical cord, liver, kidney, adrenals, thyroid, lungs, heart, great vessels, oesophagus, stomach, small intestine, spleen, thymus, pancreas, brain, eye, spinal cord, body wall, pelvis and lower limb.

Adult human tissues examined: Kidney (normal and end-stage), adrenal, myocardium, aorta, spleen, lymph node, gall bladder, pancreas, lung, skin, eye (inc. retina), prostate, bladder, liver (normal, cirrhotic, acute failure).

Non-human Primate Tissues Examined:
 (a) Chimp Tissues: Salivary gland, stomach, thyroid, parathyroid, skin, thymus, ovary, lymph node.
 (b) Rhesus Monkey Tissues: Cerebral cortex, hippocampus, cerebellum, penis.

Example 24

Identification of Receptor/Ligand Interactions

In this assay, various PRO polypeptides are tested for ability to bind to a panel of potential receptor molecules for the purpose of identifying receptor/ligand interactions. The identification of a ligand for a known receptor, a receptor for a known ligand or a novel receptor/ligand pair is useful for a variety of indications including, for example, targeting bioactive molecules (linked to the ligand or receptor) to a cell known to express the receptor or ligand, use of the receptor or ligand as a reagent to detect the presence of the ligand or receptor in a composition suspected of containing the same, wherein the composition may comprise cells suspected of expressing the ligand or receptor, modulating the growth of or another biological or immunological activity of a cell known to express or respond to the receptor or ligand, modulating the immune response of cells or toward cells that express the receptor or ligand, allowing the preparaion of agonists, antagonists and/or antibodies directed against the receptor or ligand which will modulate the growth of or a biological or immunological activity of a cell expressing the receptor or ligand, and various other indications which will be readily apparent to the ordinarily skilled artisan.

The assay is performed as follows. A PRO polypeptide of the present invention suspected of being a ligand for a receptor is expressed as a fusion protein containing the Fc domain of human IgG (an immunoadhesin). Receptor-ligand binding is detected by allowing interaction of the immunoadhesin polypeptide with cells (e.g. Cos cells) expressing candidate PRO polypeptide receptors and visualization of bound immunoadhesin with fluorescent reagents directed toward the Fc fusion domain and examination by microscope. Cells expressing candidate receptors are produced by transient transfection, in parallel, of defined subsets of a library of cDNA expression vectors encoding PRO polypeptides that may function as receptor molecules. Cells are then incubated for 1 hour in the presence of the PRO polypeptide immunoadhesin being tested for possible receptor binding. The cells are then washed and fixed with paraformaldehyde. The cells are then incubated with fluorescent conjugated antibody directed against the Fc portion of the PRO polypeptide immunoadhesin (e.g. FITC conjugated goat anti-human-Fc antibody). The cells are then washed again and examined by microscope. A positive interaction is judged by the presence of fluorescent labeling of cells transfected with cDNA encoding a particular PRO polypeptide receptor or pool of receptors and an absence of similar fluorescent labeling of similarly prepared cells that have been transfected with other cDNA or pools of cDNA. If a defined pool of cDNA expression vectors is judged to be positive for interaction with a PRO polypeptide immunoadhesin, the individual cDNA species that comprise the pool are tested individually (the pool is "broken down") to determine the specific cDNA that encodes a receptor able to interact with the PRO polypeptide immunoadhesin.

In another embodiment of this assay, an epitope-tagged potential ligand PRO polypeptide (e.g. 8 histidine "His" tag) is allowed to interact with a panel of potential receptor PRO polypeptide molecules that have been expressed as fusions with the Fc domain of human IgG (immunoadhesins). Following a 1 hour co-incubation with the epitope tagged PRO polypeptide, the candidate receptors are each immunoprecipitated with protein A beads and the beads are washed. Potential ligand interaction is determined by western blot analysis of the immunoprecipitated complexes with antibody directed towards the epitope tag. An interaction is judged to occur if a band of the anticipated molecular weight of the epitope tagged protein is observed in the western blot analysis with a candidate receptor, but is not observed to occur with the other members of the panel of potential receptors.

Using these assays, the following receptor/ligand interactions have been herein identified: PRO245 binds to PRO1868.

DEPOSIT OF MATERIAL

The following materials have been deposited with the American Type Culture Collection, 10801 University Boulevard, Manassas, Va. USA (ATCC):

| Material | ATCC Dep. No. | Deposit Date |
|---|---|---|
| DNA32292-1131 | ATCC 209258 | Sep. 16, 1997 |
| DNA33094-1131 | ATCC 209256 | Sep. 16, 1997 |

These deposit were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures that all restrictions imposed by the depositor on the availability to the public of the deposited material will be irrevocably removed upon the granting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. The isolated polypeptide having at least 95% amino acid sequence identity to:
   (a) the amino acid sequence of the polypeptide of SEQ ID NO:2;
   (b) the amino acid sequence of the polypeptide of SEQ ID NO:2, lacking its associated signal peptide; or
   (c) the amino acid sequence of the polypeptide encoded by the full-length coding sequence of the cDNA deposited under ATCC accession number 209258;
   wherein said polypeptide inhibits VEGF stimulated proliferation of endothelial cells.

2. The isolated polypeptide of claim 1 having at least 99% amino acid sequence identity to:
   (a) the amino acid sequence of the polypeptide of SEQ ID NO:2;
   (b) the amino acid sequence of the polypeptide of SEQ ID NO:2, lacking its associated signal peptide; or
   (c) the amino acid sequence of the polypeptide encoded by the full-length coding sequence of the cDNA deposited under ATCC accession number 209258;
   wherein said polypeptide inhibits VEGF stimulated proliferation of endothelial cells.

3. A chimeric polypeptide comprising a polypeptide according to claim 1 fused to a heterologous polypeptide.

4. The chimeric polypeptide of claim 3, wherein said heterologous polypeptide is an epitope tag or an Fc region of an immunoglobulin.

* * * * *